United States Patent [19]
Yamauchi et al.

[11] Patent Number: 5,609,749
[45] Date of Patent: Mar. 11, 1997

[54] ELECTROCHEMICAL ASSAY METHOD WITH NOVEL P-PHENYLENEDIAMINE COMPOUND

[75] Inventors: Tadakazu Yamauchi; Hideyuki Terasawa, both of Saitama, Japan

[73] Assignee: Mochida Pharmaceutical Co., Ltd., Tokyo, Japan

[21] Appl. No.: 366,040

[22] Filed: Dec. 29, 1994

[30] Foreign Application Priority Data

Dec. 29, 1993 [JP] Japan .................................. 5-353377

[51] Int. Cl.$^6$ .................................................. G01N 27/327
[52] U.S. Cl. ........................ 205/777.5; 204/403; 204/418; 435/817; 436/806
[58] Field of Search .......................... 204/403, 418; 205/777.5; 435/817; 436/806

[56] References Cited

U.S. PATENT DOCUMENTS

| | | | |
|---|---|---|---|
| 5,286,362 | 2/1994 | Hoenes et al. | 204/403 |
| 5,371,131 | 12/1994 | Gierenz et al. | 524/394 |

FOREIGN PATENT DOCUMENTS

| | | |
|---|---|---|
| 0441222 | 8/1991 | European Pat. Off. . |
| 0504663 | 9/1992 | European Pat. Off. . |
| 0525723 | 2/1993 | European Pat. Off. . |
| WO/07263 | 4/1992 | WIPO . |

OTHER PUBLICATIONS

Chemical Abstracts, vol. 96, No. 18, Abstract No. 152685x, p. 677 (1982) mouth unavailable.
Chemical Abstracts, vol. 83, No. 17, Abstract No. 148369m, p. 50 (1975) month unavailable.
Coury, Jr. et al, Anal. Chem., 65, pp. 242–246 (1993) month unavailable.
Willems et al, Photographic Science and Engineering, vol. 6, No. 1, pp. 39–48 (1962) month unavailable.

(List continued on next page.)

*Primary Examiner*—T. Tung
*Attorney, Agent, or Firm*—Birch, Stewart, Kolasch & Birch, LLP

[57] ABSTRACT

An enzyme electrode, specific binding or the like electrochemical assay method capable of performing always stably high detection sensitivity (responsibility) and reappearance even in the case of blood, urine and the like samples that contain interfering substances and also of applying suitably to disposable use, and a novel p-phenylenediamine compound which is used in the assay method. Particularly, an electrochemical assay method in which a substance in a liquid sample is assayed using at least one oxidoreductase, wherein an oxidoreductase, an electron mediator and an electrode which performs electron transfer with the mediator are arranged in the assay system, and a compound of the following formula [I] or a salt thereof is used as the mediator which is highly soluble in water, dried (by freeze-, vacuum- or air-drying) easily and stable under dry condition, shows a high electron transfer rate with enzymes and is almost free from the influence of interfering substances in blood, urine and the like samples:

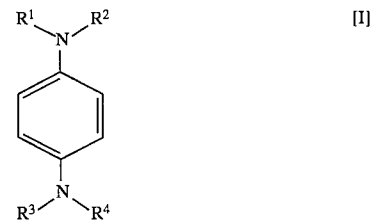

wherein $R^1$ to $R^4$ may be the same or different from one another and each means a hydrogen, a straight- or branched-chain alkyl group having 1 to 4 carbon atoms, optionally having a substituent, providing that at least one of $R^1$ to $R^4$ has one or more groups selected from hydroxyl, mercapto, carboxyl, phosphonooxy and sulfo.

13 Claims, 47 Drawing Sheets

OTHER PUBLICATIONS

Chopoorian et al, Nature, vol. 204, pp. 180–181 (Oct. 10, 1964).

Uhlig et al, Z. Chem., vol. 4, No. 11, pp. 436 (1964) month unavailable.

Uhlig et al, Z. Chrm., vol. 4, No. 12, pp. 463–465 (1964) month unavailable.

Rios et al, An. Quin., Ser. B, vol. 59, No. 7–8, pp. 501–506 (1963) month unavailable.

Rios et al, An Quin., Ser. B., vol. 61, No. 5, pp. 717–722 (1965) month unavailable.

Rios et al, An. Quin., Ser. B., vol. 61, No. 5, pp. 723–728 (1965) month unavailable.

Rios et al, An. Quin., Ser. B., vol. 59, No. 7–8, pp. 493–500 (1963) month unavailable.

Mederos et al, An. Quin., Ser. B., vol. 82, No. 2, pp. 133–139 (1986) month unavailable.

Research Disclosure, vol. 212, pp. 428–432 (Dec. 1981).

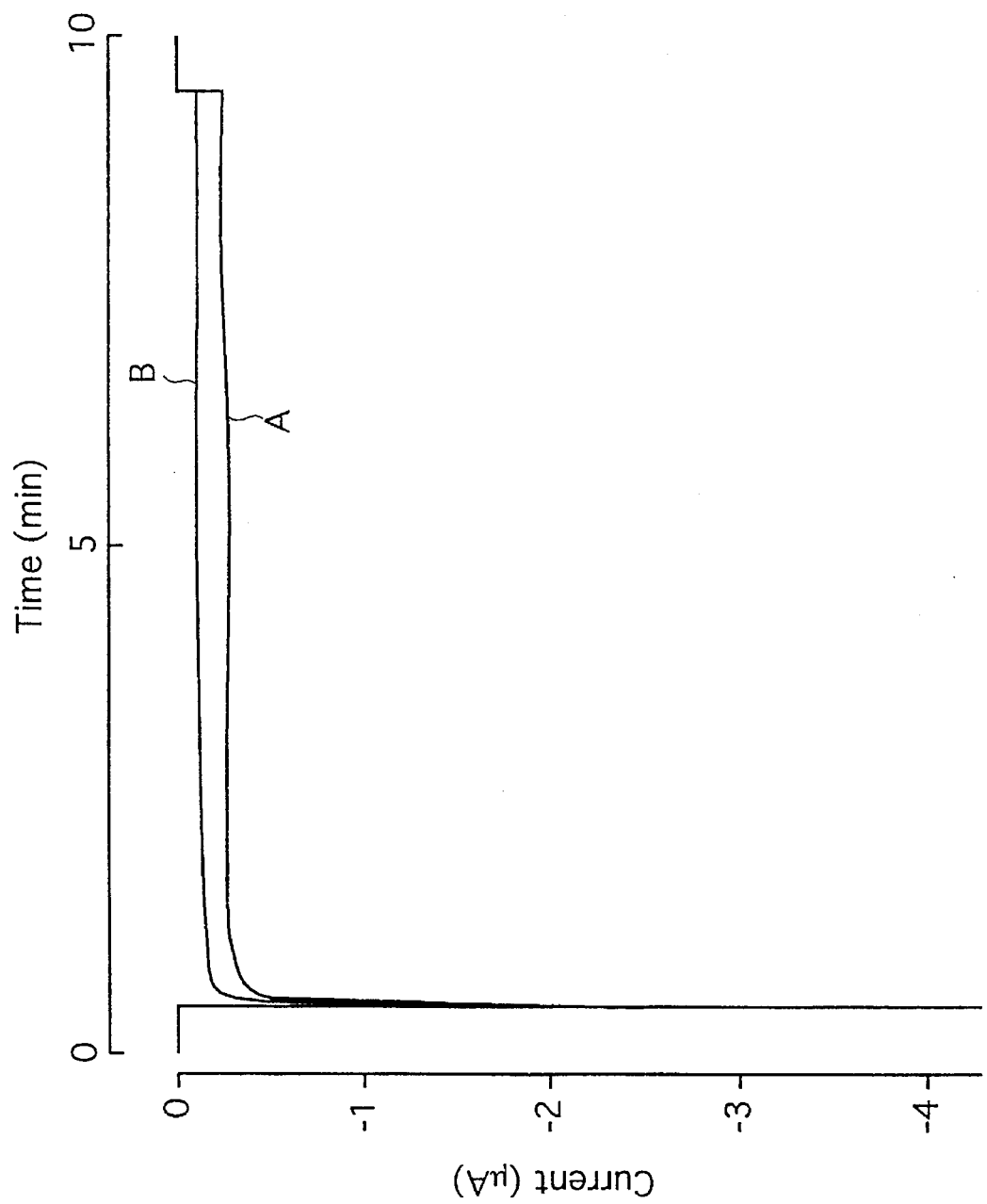

ELECTROCHEMICAL ASSAY METHOD WITH NOVEL P-PHENYLENEDIAMINE COMPOUND

FIELD OF THE INVENTION

This invention relates to an electrochemical assay method in which an electron mediator or electron transfer mediator is used and to a novel p-phenylenediamine compound.

More particularly, it relates to an electrochemical assay method in which a substance to be assayed or an analyte in a liquid sample is measured making use of a system comprising at least one oxidation-reduction enzyme, an electrode and a specified electron mediator, such as an enzyme electrode assay, a specific binding assay or the like method, and to a novel p-phenylenediamine compound which is applicable to the electrochemical assay method.

BACKGROUND OF THE INVENTION

In an enzyme electrode assay method, a chemical substance of interest is selectively measured making use of the molecule-recognizing capacity of respective enzyme, generally using an apparatus comprising an enzyme-immobilized membrane and an electrode. In the field of biochemical assay methods, simple and quick measuring methods have been developed making use of enzyme sensors and the like and have already been disclosed for example in JP-B 02-59424 (the term "JP-B as used herein means an "examined Japanese patent publication), JP-A 60-17346 (the term "JP-A" as used herein means an "unexamined published Japanese patent application) and JP-A 60-17347.

There are a number of known specific binding assay methods such as an immunoassay in which an antigen-antibody reaction is employed, a receptor assay in which a receptor is used and a nucleic acid probe assay in which hybridization of complementary nucleic acid sequences is employed. Because of the high specificity, these assay methods are used frequently in various fields including clinical chemistry and the like.

On the other hand, many attempts have been made to apply electrochemical sensors to the specific binding assay method. For example, JP-A 58-58467 discloses a specific binding reaction on the surface of an electrode to which an enzyme (catalase)-labeled antibody preparation is applied, JP-A 2-179461 discloses a competitive specific binding reaction on the surface of an electrode to which an enzyme (glucose oxidase)-labeled substance is applied and JP-A 60-17360 discloses a specific binding reaction which is effected by the use of an oxidation-reduction enzyme (glucose oxidase or the like) and an electron mediator (a ferrocene derivative or the like).

Similar techniques have also been disclosed for example in JP-A 3-25360, JP-A 60-127450, JP-A 60-242361, JP-A 63-139248, JP-W 61-500706 (the term "JP-W" as used herein means an "unexamined published Japanese translation of PCT international patent application"), U.S. Pat. Nos. 4,963,245, 5,066,372, *Anal. Chem.*, vol. 56, pp. 2355–2360 (1984) and *Clin. Chem.*, vol. 31, pp. 1449–1452 (1985).

Of these enzyme electrode methods and specific binding assay methods, an amperometric enzyme electrode method, an electrochemical sensor-aided specific binding assay method or the like generally uses a low molecular weight compound, so-called electron mediator, which mediates between a biological oxidation-reduction reaction such as of an enzyme and an electrode reaction. In other words, the electron mediator is a compound which mediates electron transfer between an enzyme reaction and an electrode reaction in an assay system that comprises at least one oxidation-reduction enzyme and an electrode capable of transferring electrons in the system.

Such an electron mediator is "reduced/oxidized" by the enzyme reaction and "oxidized/reduced" by the electrode reaction. By circulating between these two reactions, it mediates transfer of electrons from the enzyme reaction to the electrode reaction or from the electrode reaction to the enzyme reaction.

Because of this, such an electron mediator is required to be a compound having certain characteristics such as (1) it is efficiently oxidized or reduced by the enzyme reaction, (2) it is oxidized or reduced by the electrode reaction and then returned to a state which can be used by the enzyme reaction, and (3) it is stable when oxidized or reduced by the enzyme or electrode reaction.

In addition, the electron mediator which mediates electron transfer between the enzyme reactions and electrode reactions should be oxidized or reduced at an electric potential within a measurable range of the working electrode. The measurable range of electrode varies depending on the types of the electrode and solution conditions. In the case of a carbon electrode, it may be generally from $-1.2$ V to $+1.0$ V (vs. SCE).

There are a large number of such electron mediators known in the art including organic metal compounds such as ferrocene derivatives and the like (British Patent 8132034), inorganic compounds such as potassium ferri(or ferro)cyanide and the like and organic compounds such as p-phenylenediamine (PPD) derivatives and the like.

For example, it is known that a p-phenylenediamine (PPD) derivative, N,N,N',N'-tetramethyl-p-phenylenediamine (TMPD), mediates electron transfer between an electrode and sulfite oxidase which catalyzes oxidation of sulfite ions into sulfate ions (*Anal. Chem.*, vol. 65, pp. 242–246, 1993). Also, WO 92/07263 discloses a benzene derivative having amino group, an alkylamino group, a dialkylamino group, a morpholinyl group or a piperidyl group at the 1,4-position, as an electron mediator whose reduced type is slightly soluble in water.

On the other hand, N,N,N',N'-tetrakis-(2'-hydroxyethyl)-p-phenylenediamine (THEPD) and N,N,N',N'-tetrakiscarboxymethyl-p-phenylenediamine (TCPD) as other PPD derivatives have been used as photo-sensitive materials and chelating agents (*Photographic Science and Engineering*, vol. 6, no. 1, p. 39, 1962; *Nature*, vol. 204, p. 180, 1964; *Z. Chem.*, vol. 4, no. 11, p. 436, 1964; *Z. Chem.*, vol. 4, no. 12, p. 463, 1964; *An. Quin. Ser. B*, vol. 59, no. 7–8, p. 501, 1963; *An. Quin. Ser. B*, vol. 61, no. 5, p. 717, 1965; *An. Quin. Ser. B*, vol. 61, no. 5, p. 723, 1965; *An. Quin. Ser. B*, vol. 59, no. 7–8, p. 493, 1963; *An. Quin. Ser. B*, vol. 82, no. 2, p. 133, 1986; *Research Disclosure*, vol. 212, p. 428, 1981). Also, it is known that THEPD can be used as a coloring reagent of a peroxidase reaction, because its reaction in the presence of peroxidase, a naphthol derivative and hydrogen peroxide results in the formation of a color substance due to binding of its free radical to the naphthol derivative (EP 0504663). It has not been known however that THEPD and TCPD can function as electron mediators which have the above mentioned features.

In this connection, since principal use of the prior art electron mediators in electron mediator-aided assay methods is enzyme electrodes, preferred electron mediators are those which are insoluble or slightly soluble in water as described in the aforementioned WO 92/07263. That is, in order to obtain a stable electrochemical signal through mediation of electron transfer between an electrode and an oxidation-reduction enzyme immobilized or insolubilized on the electrode, it is necessary to prevent effusion of the electron mediator into blulk solution of test sample, by allowing the mediator to exist close to the electrode.

Also, when the electron mediator is a compound which is apt to undergo influence of interfering substances contained in test samples, such as ascorbic acid, uric acid, hemoglobin, oxygen and the like, it is necessary to avoid its contact with the interfering substances by converting the electron mediator into a water-insoluble form and including it inside the electrode. However, since the electron mediator is included in the electrode, this method has disadvantages in that the field of reaction is limited, only an enzyme capable of contacting efficiently with the electron mediator included inside the electrode can participate in the reaction and the signal strength generally becomes weak.

Recently, disposable type enzyme electrode chips in which a water soluble electron mediator such as potassium ferricyanide or the like is used have been developed (cf. JP-A 1-156658). Since such a water soluble electron mediator can mediate transfer of electrons between an electrode and an enzyme located at a certain distant from the electrode, effective number of enzyme molecules increases and improvement of characteristics of the enzyme electrode becomes possible.

In the case of such disposable type enzyme electrode chips, it is desirable to incorporate necessary components for the function of the electrode into the chips in advance so that the measurement can be made by simply adding a test sample to the assay system. Because of this, it is desirable that such an electron mediator has a high solubility in water, can be dried easily and is stable under dry state. Water soluble electron mediators of metal complexes such as a ferrocene derivative, potassium ferricyanide, an osmium complex and the like can satisfy these conditions to some degree. However, being small in their transfer rate of electrons to or from the enzyme, it is necessary to use the electron mediators in a large quantity. In addition, since these water soluble electron mediators are reacted in test sample solutions, they are apt to undergo influence of interfering substances contained in test samples, such as ascorbic acid, uric acid, hemoglobin, oxygen and the like. Because of this, a compound which undergoes smaller influence of such interfering substances is expected to be developed.

In addition to the above, a specific binding assay method, especially, Mediator Diffusion-Controlled Immunoassay (being abbreviated MEDIA assay method hereinafter) has recently been developed in which, an oxidation-reduction enzyme is used as a labeling substance, and the labeling substances are developed in a matrix with a liquid sample to form distributions having the different distances from each labeling substance to the electrode through a specific binding reaction of an analyte in the liquid sample with a specific binding substance. The signal substances or electron mediators therefrom diffuse to the electrode and the diffusions are rate-determining step in this assay method. The currents of the signal substances or electron mediators are measured at the electrode to determine concentration of the analyte in the liquid sample. The distance distribution can be detected by the current, and the current is corresponding to the concentration of the analyte in the sample (cf. JP-A 5-264552 (EP 0 525 723 A2)). Such a type of assay method also requires development of an electron mediator which can mediate stable transfer of electrons between the enzyme and the electrode in liquid samples such as blood, urine and the like that contain interfering substances.

Thus, the present invention contemplates overcoming the aforementioned problems involved in the prior art, thereby providing an electrochemical assay method in which a water soluble electron mediator is used, such as an enzyme electrode method or a specific binding assay method, for example MEDIA method, which has excellent detection sensitivity (responsibility), can perform the measurement stably with high reproducibility even in the case of blood, urine and the like samples that contain interfering substances and can be applied suitably to dry chemistry use, as well as a novel p-phenylenediamine compound which is used as an electron mediator in the assay method.

In an assay method in which an electron mediator is used, more particularly an assay method in which a substance to be assayed in a liquid sample is quantitatively determined using an electrode and at least one oxidation-reduction enzyme, the following oxidation-reduction enzymes are used as typical examples.

(1) Oxidases

These enzymes contain a flavin coenzyme, a metal atom, a heme or the like and use oxygen as the electron acceptor in the living body.

Examples: glucose oxidase, amino-acid oxidase, lactate oxidase, urate oxidase, xanthine oxidase, ascorbate oxidase and the like.

(2) Hydroperoxidases

In the living body, they use hydrogen peroxide as the acceptor.

Examples: peroxidase, catalase and the like.

(3) Dehydrogenases

In the living body, they use AND (H) and NADP (H) as the acceptor (or donor).

Examples: alcohol dehydrogenase, lactate dehydrogenase and the like.

Of these oxidation-reduction enzymes, glucose oxidase (GOD) is used in enzyme electrodes for the measurement of blood glucose level and horseradish peroxidase (HRPO) is used as a label enzyme in specific binding assays such as DNA hybridization, immunoassay and the like. According to experiments conducted by the present inventors, both of glucose oxidase and horseradish peroxidase showed superior current response in a buffer when hydroquinone (HQ)/benzoquinone (BQ) was used as the electron mediator, in comparison with the use of conventional electron mediators such as ferrocene derivatives, inorganic ions, metal complexes and the like. However, these electron mediators were not able to show stable and reproducible response in the presence of blood, urine and the like because of the interfering substances contained therein.

Similar interference in the presence of blood, urine and the like was found also in the case of p-phenylenediamine (PPD)-derived electron mediators such as PPD, TMPD, N,N,N',N'-tetraethyl-p-phenylenediamine (TEPD) and the like which show excellent current response in a buffer solution.

In addition, the present inventors have attempted to prepare a dry chemistry type chips by impregnating a piece of cellulose filter paper or glass filter paper with a solution of HQ, PPD, TMPD or TEPD and drying the resulting piece on an electrode (by freeze-drying, vacuum drying, air-drying or the like) or arranging it on an electrode after drying so that the impregnated electron mediator can dissolve in a liquid sample at the time of measurement. This chips, however, showed a low current response and extremely poor characteristics.

Results of detailed studies conducted by the present inventors have indicated the following problems as the principal cause of such phenomena:

(1) low water solubility of oxidized or reduced type of the compound to be used as the electron mediator, (2) poor stability after drying of the compound to be used as the electron mediator because of its high vapor pressure, and (3) poor stability in biological sample such as blood or urine of oxidized type (or radical state) or reduced type of the compound to be used as the electron mediator.

SUMMARY OF THE INVENTION

With the aim of overcoming the aforementioned problems involved in the prior art, the inventors of the present invention have conducted intensive studies and found as the result that an assay system consisting of an oxidation-reduction enzyme, an electron mediator which transfers electrons generated by the oxidation-reduction enzyme and an electrode capable of performing electron transfer between the enzyme and the electron mediator can be used suitably for the measurement of various biological components when a compound represented by the following formula [I], formula [II] or a salt thereof as the electron mediator.

In other words, the present inventors have found as the result of the intensive studies that the compound of formula [I], formula [II] or a salt thereof shows excellent characteristics in electrochemical assays such as an enzyme electrode method, a specific binding assay method, for example MEDIA method, and the like: for example, it functions as an excellent electron mediator and is highly soluble in water; it can be dried (by freeze-drying, vacuum drying, air-drying or the like) easily and is stable under dry state; it shows a large electron transfer rate with enzymes; and it functions as an electron mediator which hardly undergoes influence of interfering substances contained in test samples such as blood, urine and the like. The present invention has been accomplished on the basis of these findings.

Thus, according to the present invention, there is provided an electrochemical assay method which comprises measuring a substance to be assayed in liquid samples making use of at least one oxidation-reduction enzyme, wherein an oxidation-reduction enzyme, an electron mediator and an electrode capable of performing electron transfer with the electron mediator are arranged in the assay system, and a compound represented by the following formula [I], formula [II] or a salt thereof is used as the electron mediator:

formula [I]

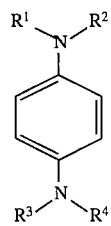

[I]

wherein $R^1$, $R^2$, $R^3$ and $R^4$ may be the same or different from one another and each represents a straight- or branched-chain alkyl group having 1 to 4 carbon atoms, which may have a substituent group, with the proviso that at least one of $R^1$, $R^2$, $R^3$ and $R^4$ has at least one group selected from the class consisting of hydroxyl, mercapto, carboxyl, phosphonooxy and sulfo.

Wherein, at least one selected from the group consisting of $R^1$, $R^2$, $R^3$ and $R^4$ preferably has hydroxyl group or carboxyl group.

Especially, the compound represented by the formula [I] is at least one compound selected from the group consisting of;

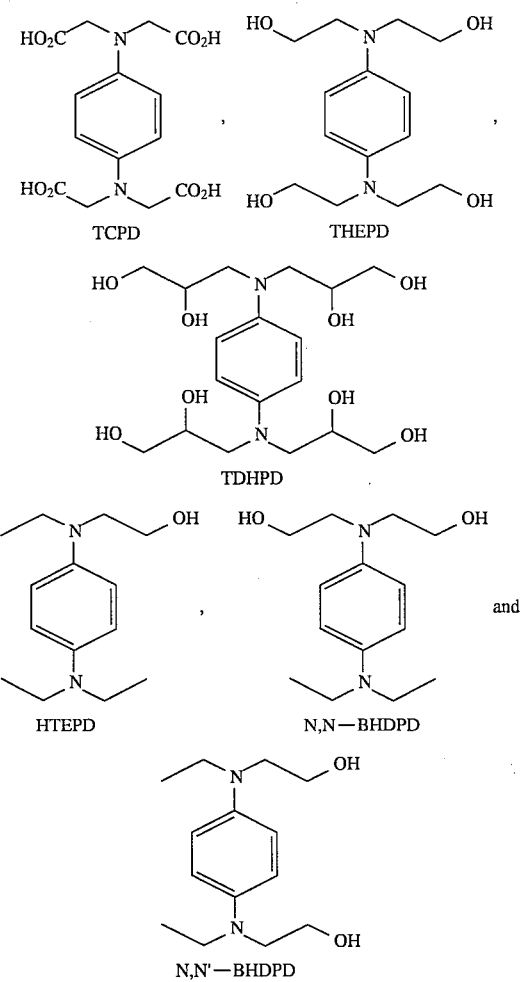

TCPD, THEPD, TDHPD, HTEPD, N,N—BHDPD, N,N'—BHDPD and formula [II]

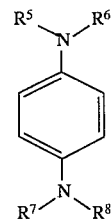

[II]

wherein $R^5$, $R^6$, $R^7$ and $R^8$ may be the same or different from one another and each represents a hydrogen, a straight- or branched-chain alkyl group having 1 to 4 carbon atoms, which may have a substituent group, with the proviso that at least one of $R^5$, $R^6$, $R^7$ and $R^8$ is alkyl group which has at least one group selected from the class consisting of hydroxyl, mercapto, carboxyl, phosphonooxy and sulfo, and at least one of $R^5$, $R^6$, $R^7$ and $R^8$ is hydrogen.

Wherein, said at least one selected from the group consisting of $R^5$, $R^6$, $R^7$ and $R^8$ preferably has hydroxyl group.

Especially, the compound represented by the formula [II] is at least one compound selected from the group consisting of;

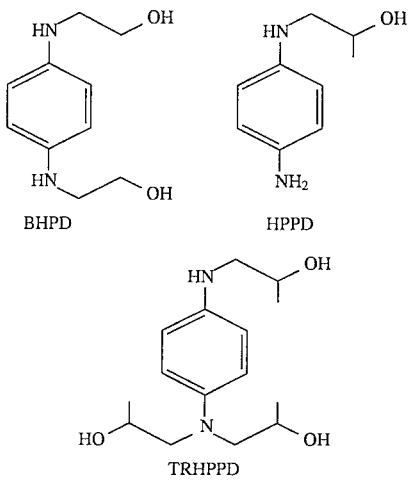

BHPD    HPPD

TRHPPD

Preferably, the substance to be assayed is a substrate of the oxidation-reduction enzyme, and a modulation of enzyme reaction generated in response to the amount of the substrate is detected as a modulation of electrochemical signals on the electrode.

It is preferable to measure the substance to be assayed by means of a specific binding assay making use of the oxidation-reduction enzyme as a label and at least one binding substance specific for the substance to be assayed.

Also, it is preferable to measure the substance to be assayed by a MIDIA method effecting the electrochemical assay method by using a device comprising a matrix as an area where a liquid sample presumably containing the substance to be assayed is developed, a sample-introducing means from which a sample is introduced into the matrix and an electrode adjacent to the matrix, introducing a sample into the sample-introducing means to allow a substance to be assayed in the sample to react in the matrix with a first specific binding substance and a second specific binding substance which is labeled with an oxidation-reduction enzyme capable of forming an electron transfer species that generates a signal at the electrode portion, or introducing a sample into the matrix after allowing the substance to be assayed in the sample to react in an outside area of the matrix with a first specific binding substance and a second specific binding substance which is labeled with an oxidation-reduction enzyme capable of forming an electron transfer species that generates a signal at the electrode portion, thereby effecting changes in the distribution of at least one molecular species among a complex of the oxidation-reduction enzyme-labeled second specific binding substance and the substance to be assayed, a complex of the oxidation-reduction enzyme-labeled second specific binding substance, the substance to be assayed and the first specific binding substance and a free form of the oxidation-reduction enzyme-labeled second specific binding substance, and detecting changes in the distribution in response to the amount of the substance to be assayed in the sample as a signal modulation at the electrode, which is limited by the mass transfer of the electron transfer species generated by the oxidation-reduction enzyme.

It is preferable also to measure the substance to be assayed by another MIDIA method effecting the electrochemical assay method by using an apparatus comprising a matrix as an area where a liquid sample presumably containing the substance to be assayed is developed, a sample-introducing means from which a sample is introduced into the matrix and an electrode adjacent to the matrix in which either one of a specific binding substance specific for the substance to be assayed and a substance which competes with the substance to be assayed for the specific binding substance is labeled with the oxidation-reduction enzyme capable of forming an electron transfer species that generates a signal at the electrode portion, introducing a sample into the sample-introducing means to allow the substance to be assayed in the sample to react in the matrix in a competitive manner with the specific binding substance or the substance which competes with the substance to be assayed for the specific binding substance, or introducing a sample into the matrix after allowing the substance to be assayed in the sample to react in an outside area of the matrix in a competitive manner with the specific binding substance or the substance which competes with the substance to be assayed for the specific binding substance, thereby effecting changes in the distribution of at least one oxidation-reduction enzyme-labeled molecular species among a complex of the specific binding substance and the substance to be assayed, a complex of the specific binding substance and the substance which competes with the substance to be assayed for the specific binding substance, a free form of the specific binding substance and a free form of the substance which competes with the substance to be assayed for the specific binding substance, and detecting changes in the distribution in response to the amount of the substance to be assayed in the sample as a signal modulation at the electrode, which is limited by the mass transfer of the electron transfer species generated by the oxidation-reduction enzyme.

Other objects and advantages of the present invention will be made apparent as the description progresses.

BRIEF DESCRIPTION OF THE DRAWINGS

FIG. 48 is a graph showing another example of the electron transfer activity of p-phenylenediamine derivative having tri-substituted amino groups obtained from the reaction of p-phenylenediamine with propyleneoxide.

Figure 1:
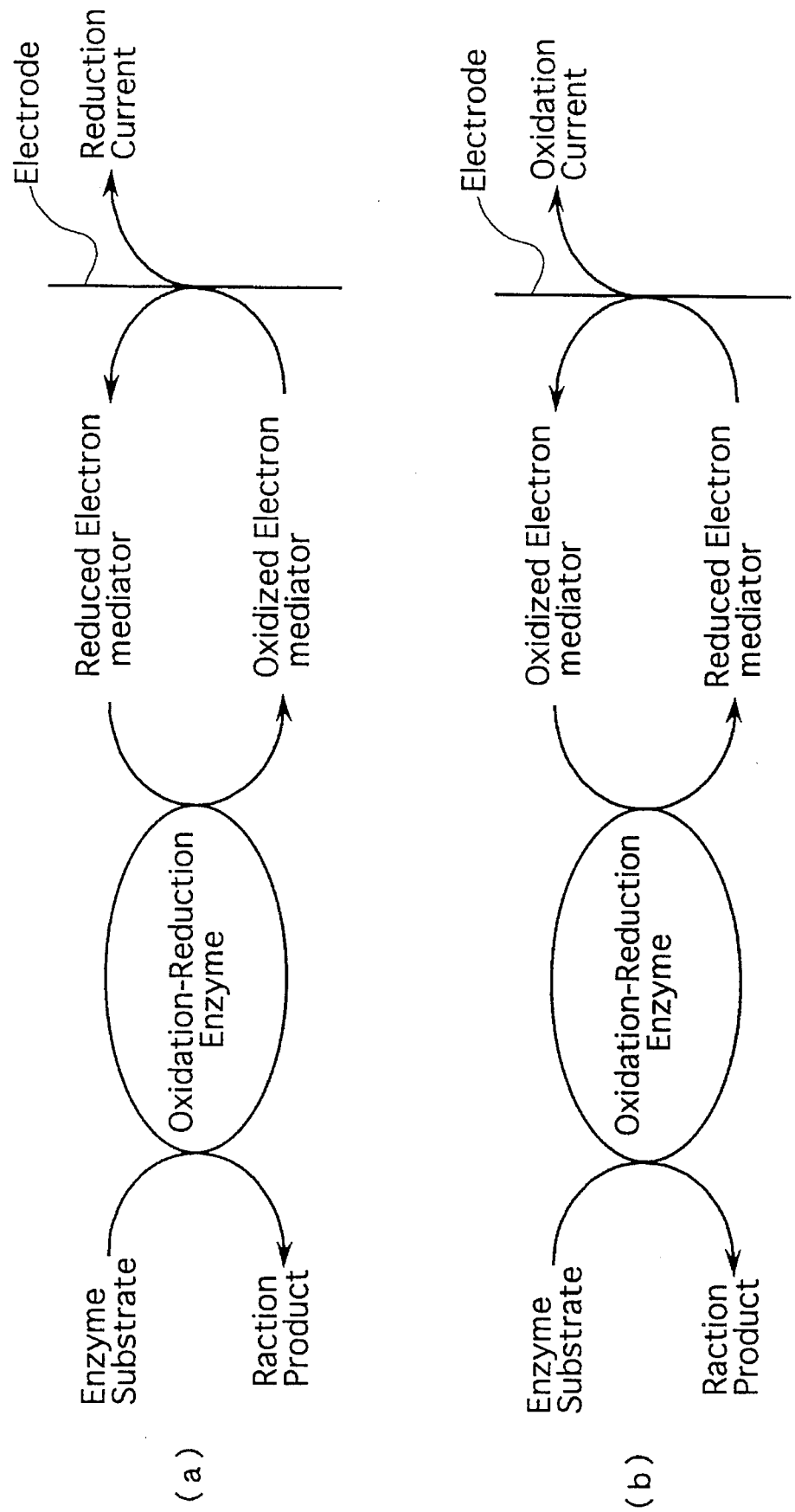
FIG. 1(a) and (b) are conceptual drawings respectively showing actions of the electron mediator.

In these figures, parts of the assay device are indicated by characters as follows: 10, an upper cover; 10a, a sample-introducing hole; 12, a filter; 14, a label-impregnated member; 16, an electron mediator-impregnated member; 16a and 24a, sealing means; 18, a communication means; 20, an electrode portion; 22, a matrix; 24, a absorption means; 26, a lower support; 28, a support; 30, a through hole; 32, a reference electrode; 34, a working electrode; 36, an insulating means; and 38, a sample-introducing means.

DETAILED DESCRIPTION OF THE INVENTION

The electrochemical assay method of the present invention and the novel p-phenylenediamine compound which can be used in the assay method are described in the following in detail.

As described in the foregoing, the electrochemical assay method (to be referred to as "assay method" hereinafter) of the present invention contains in its assay system at least one oxidation-reduction enzyme, an electron mediator and an electrode capable of performing electron transfer with the electron mediator, and uses a compound represented by the following formula [I] or [II] or a salt thereof as the electron mediator:

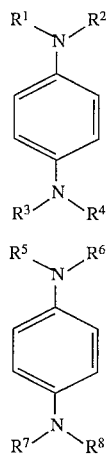

wherein each of $R^1$, $R^2$, $R^3$ and $R^4$ independently represents a straight- or branched-chain alkyl group having 1 to 4 carbon atoms, which may have a substituent group, with the proviso that at least one of $R^1$, $R^2$, $R^3$ and $R^4$ has at least one group selected from the class consisting of hydroxyl, mercapto, carboxyl, phosphonooxy and sulfo, wherein $R^5$, $R^6$, $R^7$ and $R^8$ may be the same or different from one another and each represents hydrogen, a straight- or branched-chain alkyl group having 1 to 4 carbon atoms, which may have a substituent group, with the proviso that at least one of $R^5$, $R^6$, $R^7$ and $R^8$ is alkyl group which has at least one group selected from the class consisting of hydroxyl, mercapto, carboxyl, phosphonooxy and sulfo, and at least one of $R^5$, $R^6$, $R^7$ and $R^8$ is hydrogen As a result of intensive studies, the present inventors have found for the first time that the compound represented by the above formula [I] or [II] functions excellently as an electron mediator in the electrochemical assay. It was found also that, when at least one of $R^1$ to $R^8$ of the compound of formula [I] or [II] has at least one group selected from the class consisting of hydroxyl, mercapto, carboxyl, phosphonooxy and sulfo, the resulting compound shows a low vapor pressure and becomes highly soluble in water so that it can be dried (by freeze-drying, vacuum drying, air-drying or the like) easily, becomes stable under dry condition and dissolves quickly in a liquid sample added to show excellent response. In other words, this compound was found to have excellent characteristics required for electron mediators: for example, it can be applied suitably to dry chemistry use by impregnating porous materials such as various types of filter paper and the like with the compound and drying the resulting material; it can reduce interference caused by interfering substances contained in test samples such as blood, urine and the like; and it shows excellent electric current response because of small disturbance in its electron reaction with enzymes.

In consequence, according to the assay method of the present invention in which the compound of the aforementioned formula [I] or [II] is used as the electron mediator, its detection sensitivity (responsibility) is excellent, it can be applied suitable to disposable use and stable measurement can be made constantly with good reproducibility even in the case of blood, urine and the like samples which contain interfering substances.

With regard to $R^1$, $R^2$, $R^3$ and $R^4$ of the compound of formula [I], all known groups which satisfy the aforementioned requirements can be used, their illustrative examples including methyl, ethyl, propyl, hydroxymethyl, 1-hydroxyethyl, 2-hydroxyethyl, 1,2-dihydroxyethyl, 1-hydroxypropyl, 2-hydroxypropyl, 3-hydroxypropyl, 2-(1-hydroxy)propyl, 2,3-dihydroxypropyl, 2-(1,3-dihydroxy)propyl, 3-hydroxy-2-methylpropyl, mercaptomethyl, carboxymethyl, phosphonooxymethyl, sulfomethyl and the like groups, of which hydroxymethyl, 1-hydroxyethyl, 2-hydroxyethyl, 1-hydroxypropyl, 2-hydroxypropyl, 3-hydroxypropyl, 2-(1-hydroxy)propyl, 2,3-dihydroxypropyl, carboxymethyl and the like groups are particularly preferred.

In this instance, the groups $R^1$, $R^2$, $R^3$ and $R^4$ may be the same or different from one another.

With regard to $R^5$, $R^6$, $R^7$ and $R^8$ of the compound of formula [II], all known groups which satisfy the aforementioned requirements can be used, their illustrative examples including hydrogen, methyl, ethyl, propyl, hydroxymethyl, 1-hydroxyethyl, 2-hydroxyethyl, 1,2-dihydroxyethyl, 1-hydroxypropyl, 2-hydroxypropyl, 3-hydroxypropyl, 2-(1-hydroxy)propyl, 2,3-dihydroxypropyl, 2-(1,3-dihydroxy)propyl, 3-hydroxy-2-methylpropyl, mercaptomethyl, carboxymethyl, phosphonooxymethyl, sulfomethyl and the like groups, of which hydroxymethyl, 1-hydroxyethyl, 2-hydroxyethyl, 1-hydroxypropyl, 2-hydroxypropyl, 3-hydroxypropyl, 2-(1-hydroxy)propyl, 2,3-dihydroxypropyl, carboxymethyl and the like groups are particularly preferred.

In this instance, the groups $R^5$, $R^6$, $R^7$ and $R^8$ may be the same or different from one another, but at least one of them is alkyl group and at least one of them is hydrogen.

The following compounds are illustrative examples of the compound of formula [I] or [II] to be used in the assay method of the present invention.

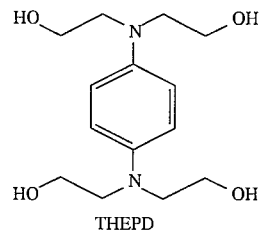
THEPD

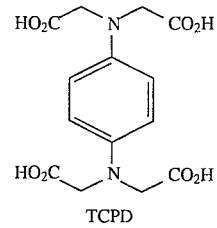
TCPD

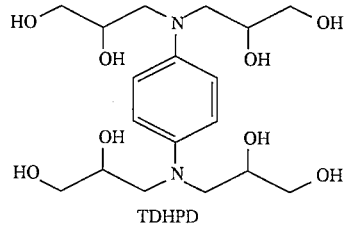
TDHPD

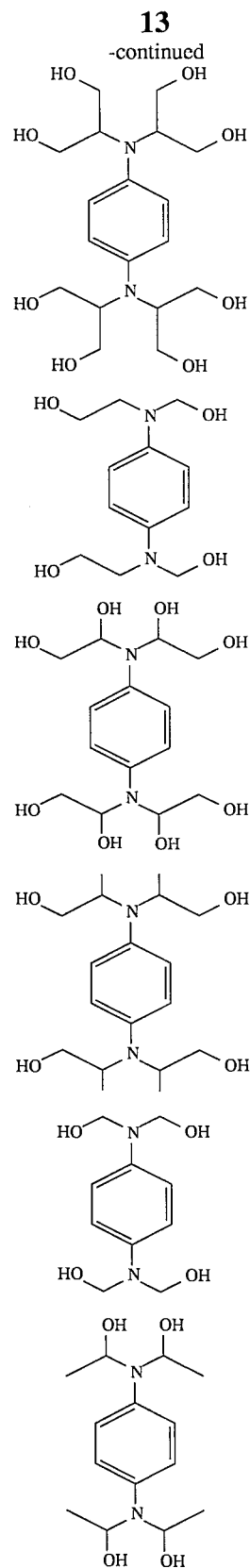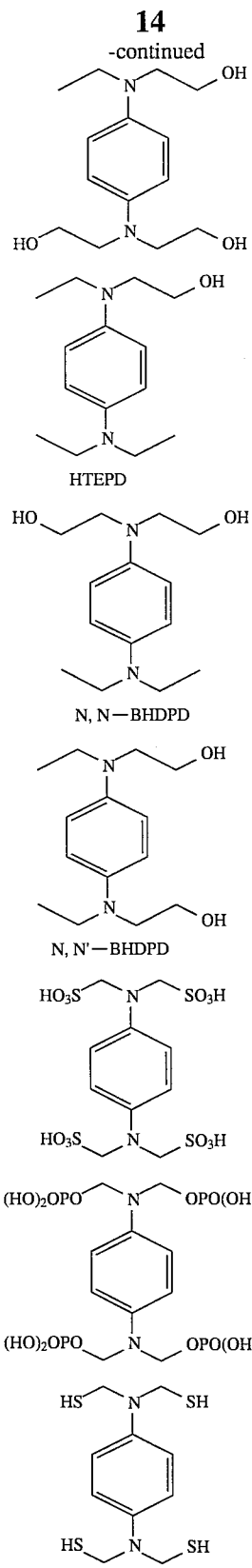

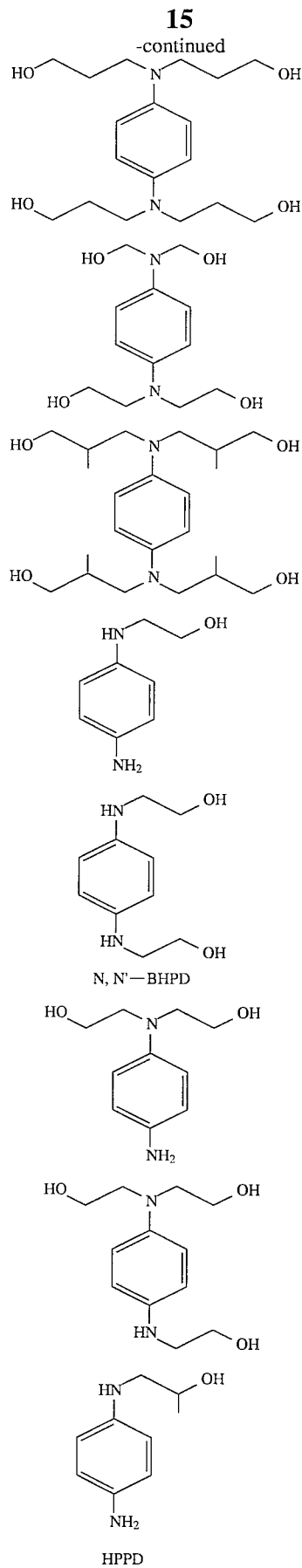
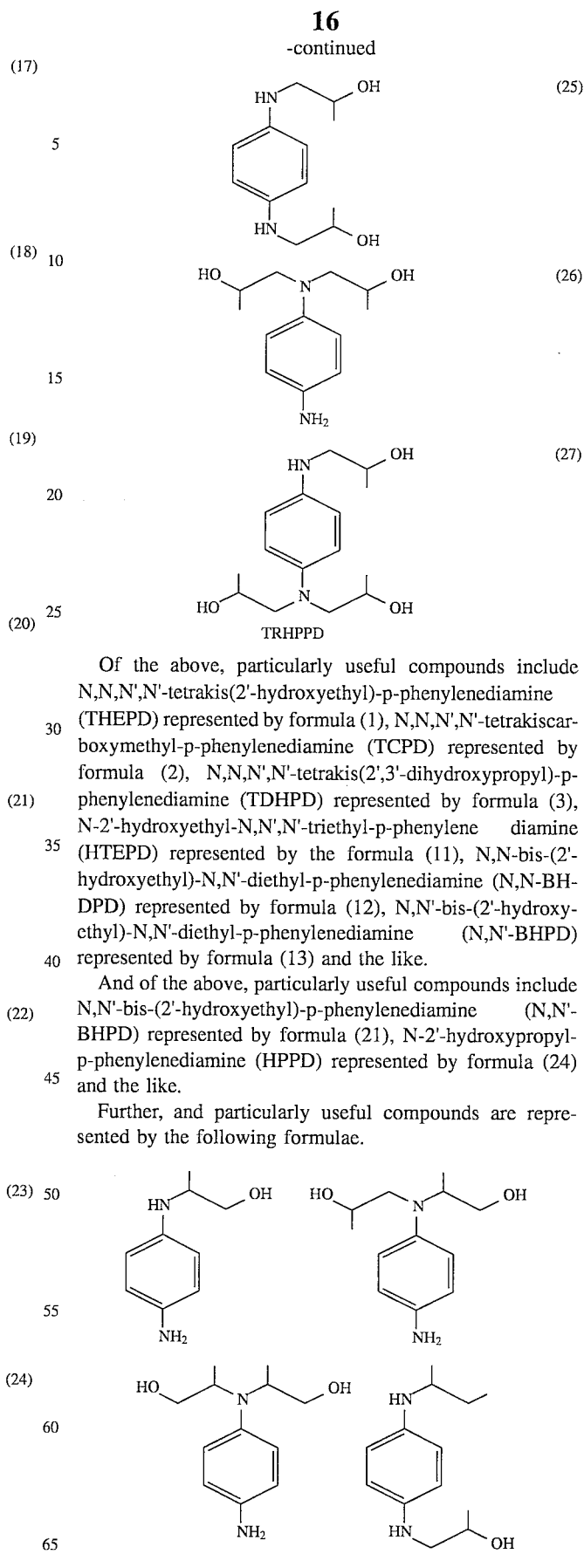

Of the above, particularly useful compounds include N,N,N',N'-tetrakis(2'-hydroxyethyl)-p-phenylenediamine (THEPD) represented by formula (1), N,N,N',N'-tetrakiscarboxymethyl-p-phenylenediamine (TCPD) represented by formula (2), N,N,N',N'-tetrakis(2',3'-dihydroxypropyl)-p-phenylenediamine (TDHPD) represented by formula (3), N-2'-hydroxyethyl-N,N',N'-triethyl-p-phenylene diamine (HTEPD) represented by the formula (11), N,N-bis-(2'-hydroxyethyl)-N,N'-diethyl-p-phenylenediamine (N,N-BHDPD) represented by formula (12), N,N'-bis-(2'-hydroxyethyl)-N,N'-diethyl-p-phenylenediamine (N,N'-BHPD) represented by formula (13) and the like.

And of the above, particularly useful compounds include N,N'-bis-(2'-hydroxyethyl)-p-phenylenediamine (N,N'-BHPD) represented by formula (21), N-2'-hydroxypropyl-p-phenylenediamine (HPPD) represented by formula (24) and the like.

Further, and particularly useful compounds are represented by the following formulae.

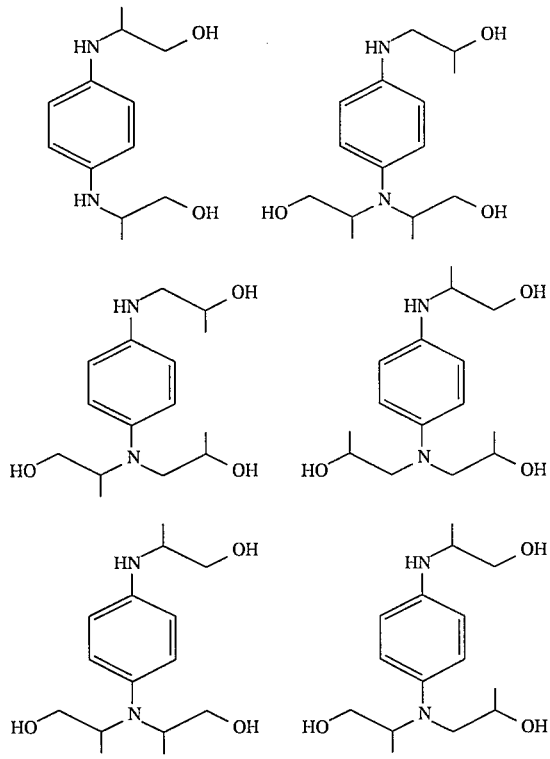

These electron mediators represented by the formula [I] or [II] can be synthesized in accordance with various known methods. For example, a compound of interest may be obtained by dissolving p-phenylenediamine and a halide of a compound which corresponds to $R^1$, $R^2$, $R^3$, $R^4$, $R^5$, $R^6$, $R^7$ and $R^8$ in an alcohol or the like solvent, heating the solution under reflux to effect the reaction, and then separating and purifying the thus obtained compound by filtration, column chromatography and the like means. Also, a compound having a hydroxyl group at the 2-position carbon atom of $R^1$ to $R^8$ may be synthesized by dissolving p-phenylenediamine and an ethylene oxide derivative in a solvent, heating the solution under reflux to effect the reaction, and then separating and purifying the thus obtained compound of interest by filtration, column chromatography and the like means.

In the assay method of the present invention, salts of the electron mediator of formula [I] or [II] may also be used suitably. Illustrative examples of such salts include hydrochloride, nitrate, sulfate, perchlorate, p-toluenesulfonate and the like. Also, when the electron mediator of formula [I] or [II] contains one or more groups selected from the class consisting of carboxyl group, phosphonooxy group and sulfo group, its sodium salt, potassium salt and the like may be used suitably. Especially, THEPD hydrochloride, TCPD hydrochloride, TDHPD hydrochloride and the like may be used most suitably.

The electron mediator represented by the formula [I] or [II] is oxidized or reduced by an oxidation-reduction enzyme or an electrode and converted into an electron transfer species of oxidized or reduced state. When an electron transfer species of oxidized state is formed by the oxidation-reduction reaction of the oxidation-reduction enzyme, the thus formed electron transfer species of oxidized state is returned to its reduced state by an electrode reaction while the reduction current is detected as a signal at the electrode (cf. FIG. 1(a)). On the other hand, when an electron transfer species of reduced state is formed by the oxidation-reduction reaction of the oxidation-reduction enzyme, the thus formed electron transfer species of reduced state is returned to its oxidized state by an electrode reaction while the oxidation current is detected as a signal at the electrode (cf. FIG. 1(b)). In other words, similar effect can be obtained by the assay method of the present invention when the reaction is started from the electron transfer species of either oxidized or reduced state as shown in FIGS. 1(a) and (b). In consequence, the electron mediator of formula [I] or [II] includes an electron transfer species which is an oxidized state of the mediator and another electron transfer species which is a reduced state of the mediator.

According to the assay method of the present invention, amount of the electron mediator of formula [I] or [II] to be used is not particularly limited and can be decided depending on the type, quantity and the like of the used electrode, oxidation-reduction enzyme and substance to be assayed.

Also, according to the assay method of the present invention, the electron mediator of formula [I] or [II] can be used under various conditions. For example, the mediator may be used by a method in which it is directly dissolved in or mixed with the assay system, a method in which it is dried or freeze-dried and then dissolved at the time of measurement, a method in which it is contained in an electrode paste or a method in which it is dissolved in a buffer or the like, soaked into a filter paper which is subsequently dried and then dissolved again in a sample solution or the like at the time of measurement. In each of these cases, excellent electrochemical assay can be realized because of the excellent water solubility, drying capacity, drying stability and electric current responsibility of the electron mediator, as well as the low influence of interfering substances in test samples.

In the assay method of the present invention, an electrochemical measurement is carried out making use of at least one oxidation-reduction enzyme. The oxidation-reduction enzyme to be used in the present invention is not particularly limited and various oxidation-reduction enzymes can be selected and used depending on the type of substance to be assayed and other conditions. Illustrative examples of such enzymes include glucose oxidase, peroxidase such as horseradish peroxidase, galactose oxidase, amino-acid oxidase, AND(P) oxidase, lactate oxidase, pyruvate oxidase, alcohol oxidase, urate oxidase, cholesterol oxidase, choline oxidase, xanthine oxidase, nucleoside oxidase, ascorbate oxidase, diaphorase and the like. Of these, glucose oxidase for use in the measurement of blood glucose level and horseradish peroxidase as a label enzyme for use in specific binding assays are used most preferably. Amount of the oxidation-reduction enzyme to be used is not particularly limited and can be decided at will depending on the type, quantity and the like of the used electrode, electron mediator and substance to be assayed.

Various electrodes commonly used in electrochemical assays such as enzyme electrode methods, specific binding assay methods and the like can be used in the assay method of the present invention. Illustrative examples of such electrodes include carbon electrodes such as glassy carbon electrode, pyrolytic graphite electrode, carbon paste electrode, carbon fiber electrode and the like, conductive transparent electrodes such as platinum electrode, gold electrode, ITO electrode and the like, oxide electrodes such as of $TiO_2$ and the like, and modified electrodes which are modified with functional compounds. In the assay method of the present invention, an electrode produced by printing a pattern on a substrate by screen printing or the like using a conductive carbon ink is used most preferably in view of its broad applicability.

Shape of the electrode (plane electrode, porous electrode or the like) and its size are not particularly limited and can be decided depending for example on the type and quantity of each substance to be assayed, quantity and characteristics (viscosity and the like for instance) of each test sample and purpose and conditions of the assay.

The assay method of the present invention which is carried out using a system consisting of such oxidation-reduction enzyme, electron mediator and electrode can basically be applied suitably to various known electrochemical assays such as enzyme electrode methods, specific binding assay methods and the like. For example, it can be applied to amperometric type enzyme sensors, immunosensors, nucleic acid sensors and the like. More particularly, it can be applied to the measurement of for example: blood glucose, cholesterol, uric acid, lactic acid and the like making use of enzyme sensors; various hormones such as human chorionic gonadotropin (hCG), luteinizing hormone (LH), human placental lactogen (hPL), estrogen and the like making use of specific binding assay methods; various virus-related antigens and antibodies such as HBs antibody, HBs antigen, HBc antibody, HBe antigen, HCV antibody, HIV antibody and the like; specific IgE antibodies for various allergens; tumor markers of AFP, CEA and the like; various blood proteins and drugs such as $\beta_2$m, CRP and the like and metabolic products thereof; and virus- and tumor-related polynucleotide sequences.

According to the assay method of the present invention, various known electrochemical assays such as enzyme electrode methods, specific binding assay methods and the like can be carried out in the same manner as the conventional assay methods. Making use of the excellent water solubility, property, stability in the dry state and the like of the electron mediator of the formula [I] or [II], the assay method of the present invention can be applied most suitably to a dry chemistry type assay device in which a piece of cellulose filter paper, glass filter paper or the like is impregnated with a solution of the electron mediator and then dried to prepare an assay piece, and the thus impregnated electron mediator is dissolved by a liquid sample at the time of measurement thereby allowing the mediator to diffuse and migrate in a matrix so that it functions as a substance which transfers electrons to be used as a signal.

Figure 2:
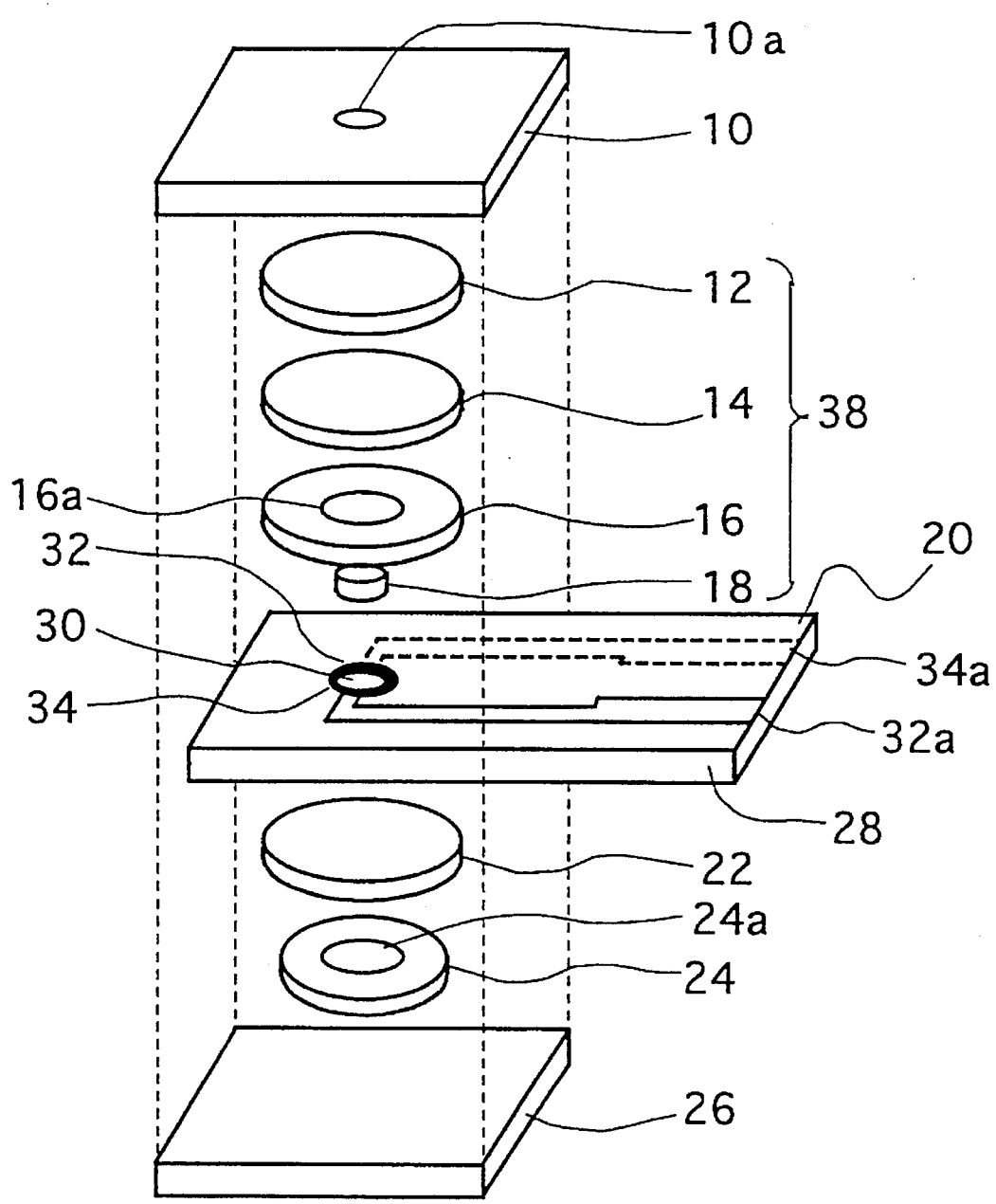
FIG. 2 is a general exploded perspective illustration showing an example of the (specific binding) assay device for use in the practice of the electrochemical assay method of the present invention.

FIG. 2 shows a dry chemistry type specific binding assay device for use in the practice of the assay method of the present invention, for example MEDIA method. In this connection, the device-constructing members and assay methods making use of the device are described in detail in EP 0 525 0 723 A2 (U.S. Ser. No. 243,095) which therefore is incorporated herein by reference.

Figure 3:
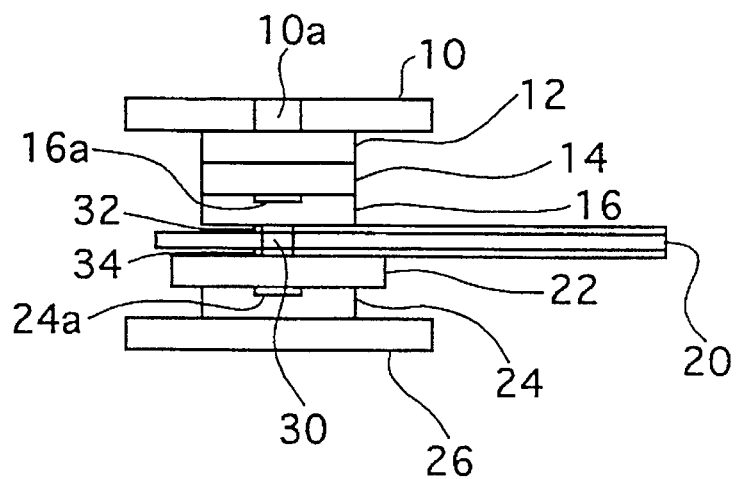
FIG. 3 is a conceptional drawing showing a section of the assemble of the (specific binding) assay device shown in FIG. 2.

The assay device shown in FIG. 2 is composed of, counting from its upper part, an upper cover 10, a filter 12, a labeled antibody-impregnated member 14, an electron mediator-impregnated member 16, a communication means 18, an electrode portion 20, a matrix 22, an absorption means 24 and a lower support 26, and these parts are placed one upon another in the order to constitute a combination shown in FIG. 3. A sample-introducing means 38 is constructed by the filter 12, the labeled antibody-impregnated member 14, the electron mediator-impregnated member 16 and the communication means 18. In this connection, assay devices for use in the assay method of the present invention are not limited to those which contain all of these parts, and the constructions disclosed in the aforementioned EP 0 525 723 A2 (U.S. Ser. No. 243,095) can also be used, which therefore are incorporated herein by reference.

The upper cover 10 is formed from various synthetic resins such as acrylics, polyvinyl chloride, polystyrene, ABS resin, epoxy resin and the like, as well as glass fibers, and its central portion has a sample-introducing hole 10a from which a sample is injected.

The filter 12, generally formed from woven or non-woven fabric, is used for removing unnecessary solid materials (interfering substances) contained in samples and simultaneously effecting uniform introduction of the sample.

The labeled antibody-impregnated member 14 is prepared by impregnating a piece of glass fiber filter paper, cellulose fiber filter paper, non-woven fabric or the like with a solution of an oxidation-reduction enzyme-labeled antibody which is one of the composing elements of the present invention, and drying the impregnated piece. That is, when a sample is passed through the labeled antibody-impregnated member 14, the oxidation-reduction enzyme-labeled antibody is eluted from the member and mixed with a substance to be assayed, or the reaction starts.

The electron mediator-impregnated member 16 is prepared by impregnating a piece of glass fiber filter paper, cellulose fiber filter paper, non-woven fabric or the like with a solution of an electron mediator which is a characteristic element of the present invention, and drying the impregnated piece. That is, when a sample is passed through the electron mediator-impregnated member 16, the electron mediator is eluted from the member and mixed with the sample. As described in the foregoing, since the compound of formula [I] or [II] is used as the electron mediator in the assay method of the present invention, the electron mediator has excellent property and stability in the dry state and is eluted and mixed quickly.

As a preferred mode of the illustrated assay device, a sealing means 16a through which water cannot be passed is formed on the upper central portion of the electron mediator-impregnated member 16. By the arrangement of this sealing means 16a, more accurate assay can be carried out, because the vertical flow of the sample until the labeled antibody-impregnated member 14 can be changed to horizontal direction which renders possible prolongation of time of the sample flow to ensure sufficient time for the reaction and improvement of the reaction efficiency by the mixing effect. Materials and methods for the formation of the sealing means 16a are not particularly limited, and it can be formed by adhering a piece of a water-impermeable material such as vinyl chloride, cellulose acetate or the like to the central portion of the electron mediator-impregnated member 16 via an adhesive agent such as an acrylic adhesive agent or the like.

In the illustrated assay device, the labeled antibody-impregnated member 14 which contains an oxidation-reduction enzyme-labeled antibody and the electron mediator-impregnated member 16 that contains an electron mediator are separately formed, but the assay device to be used in the present invention may also comprises, in stead of these members, a reagent-impregnated member which contains both of the oxidation-reduction enzyme-labeled antibody and electron mediator. In addition, though the electron mediator is contained in the electron mediator-impregnated member 16 in the illustrated assay device, proper results of measurement can also be obtained when it is contained in the matrix 22 or absorption means 24 because of the excellent property in the dry state and water solubility of the electron mediator represented by the formula [I] or [II].

The communication means 18 is formed from glass fiber filter paper, cellulose fiber filter paper or the like and used to introduce a sample and the like passed through the electron mediator-impregnated member 16 into the matrix 22 via a predetermined area of the electrode portion 20. The communication means 18 is arranged by inserting it into a through hole 30 of the electrode portion 20.

Figure 4:
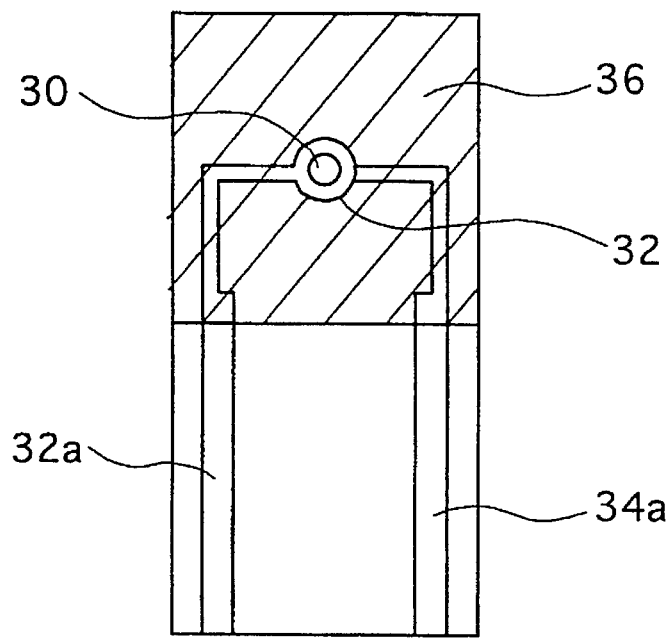
FIG. 4 is an illustration showing a general top plan view of the electrode portion of the (specific binding) assay device shown in FIG. 2.

The electrode portion 20 contains a working electrode which is one of the composing elements of the present invention. In the electrode portion 20 of the illustrated assay device shown in FIGS. 2 and 4, the circular through hole 30 is formed on an insulating support 28, a reference electrode (counter electrode) 32 and its terminal 32a are formed on the peripheral of the through hole 30 on the upper surface of the support 28, and a working electrode (detection electrode) 34 and its terminal 34a are formed on the peripheral of the through hole 30 on the lower surface of the support 28. At the time of measurement, the terminals of both electrodes are connected to an external measuring equipment. In addition, as shown in FIG. 4 with a shaded portion, an insulating layer 36 is formed on both upper and lower surfaces of the support 28 of the electrode portion 20, where the electron mediator-impregnated member 16 and the matrix 22, excluding the reference electrode 34 and working electrode 36, are contacted with the surfaces.

The working electrode 34 to be used as a detection electrode can be formed from the aforementioned various materials. The reference electrode 32 is a silver/silver chloride electrode or the like. The support 28 is formed from various known insulating materials such as PET (polyethylene terephthalate), polyvinyl chloride, polyimide, polyester and the like. The insulating layer 36 is formed from various known insulating ink materials such as of acrylic resin, polyester and the like.

In this instance, the working electrode 34, reference electrode 32 and insulating layer 36 in the illustrated assay device may be formed by known film forming techniques which include for example thick film forming techniques such as screen process printing, docter knife and the like and thin film forming techniques such as sputtering, CVD and the like.

The matrix 22 is an area for use in the distribution of an enzyme-labeled body formed by specific binding of a substance to be assayed in a liquid sample and the oxidation-reduction enzyme-labeled antibody, and a distance distribution of the labeled body from the working electrode 34 is measured as an electric current value via the aforementioned electron mediator. The matrix 22 is prepared for example by a method in which an antibody, antigen, nucleic acid or the like to be used in the specific binding reaction is insolubilized and dried on a porous membrane or the like. When a sample flows into the matrix 22, specific binding reaction between the insolubilized antibody and the substance to be assayed occurs, distribution of the enzyme-labeled body changes and an electron transfer species formed by the enzyme reaction diffuses and migrates to be detected by the working electrode 34 as an electrochemical modulation in response to the reaction. In this case, excess amount of the sample passes through the matrix 22 and is absorbed by the absorption means 24.

The absorption means 24 absorbs excess sample passed through the matrix 22 as described above and is prepared for example from a chromatography filter paper or the like cellulose filter paper or a polymer having high water absorption power. In the illustrated assay device, such a material of the absorption means 24 retains an enzyme reaction substrate such as a hydrogen peroxide-urea dried mixture or the like so that it also functions as an enzyme reaction substrate-impregnated portion.

As a preferred mode of the illustrated assay device, a sealing means 24a through which water cannot be passed is formed on the upper central portion of the absorption means 24. Similar to the case of the aforementioned sealing means 16a, more accurate assay can be carried out by the arrangement of the sealing means 24a, because the vertical flow of the sample can be changed to horizontal direction which renders possible prolongation of time of the sample flow that results in the improvement of the efficiency of the specific binding reaction and clear distribution of the labeled body in the matrix. The sealing means 24a can be prepared in the same manner as the case of the aforementioned sealing means 16a.

The illustrated assay device is constructed by superposing these parts on the lower support 26 in the order shown in FIGS. 2 and 3. The lower support 26 is prepared from various resin materials such as acrylic resin similar to the case of the upper cover 10.

In such a type of assay device, each sample is injected through the sample-introducing hole 10a formed on the upper cover 10. The sample thus injected from the sample-introducing hole 10a passes through the filter 12 where undesirable substances and the like are removed and flows into the labeled antibody-impregnated member 14. In the labeled antibody-impregnated member 14, the dried and retained oxidation-reduction enzyme-labeled antibody is eluted by the flowed sample and mixed therewith or starts a specific binding reaction with a substance to be assayed in the sample.

The sample is then transferred into the electron mediator-impregnated member 16. Since an electron mediator is dried and retained in the electron mediator-impregnated member 16 as described in the foregoing, the electron mediator is eluted by the flowed sample and mixed therewith. Since the sealing means 16a is formed on the upper surface of the electron mediator-impregnated member 16 in the illustrated assay device, the vertical sample flow is changed into horizontal direction to ensure sufficient reaction time as described in the foregoing.

The sample thus passed through the electron mediator-impregnated member 16 flows into the matrix 22 via the communication means 18 and the through hole 30 of the electrode portion 20. When the sample flows into the matrix 22, distribution of the oxidation-reduction enzyme-labeled body in the matrix 22 is determined by specific binding reaction of the substance to be assayed in the liquid sample with the insolubilized antibody, and an electron transfer species which is formed by the enzyme reaction of the oxidation-reduction enzyme-labeled body and capable of undergoing electrode reaction reaches the working electrode 34 by diffusion. That is, distribution of the substance to be assayed in the radial direction of the working electrode 34 is detected by the working electrode 34 as an electrochemical modulation in response to the enzyme reaction. Excess amount of the sample passes through the matrix 22 and is absorbed by the absorption means 24.

In consequence, according to the above assay device, result of the specific binding reaction of a substance to be assayed with the insolubilized antibody in the matrix 22 determines distribution in the matrix 22 of the enzyme-labeled body formed by the above specific binding reaction in response to the amount of the substance to be assayed in the sample, electrons are transferred at the working electrode 34 via diffusion migration of the electron transfer species formed by the above enzyme-labeled body, and the electron transfer caused by the electrode reaction is detected as an electrochemical modulation. As the result, the substance to be assayed in the sample is determined by measuring distribution of the specific binding reaction in the radial direction of the matrix 22.

Thus, the electrochemical assay method using MEDIA method and novel p-phenylenediamine compound of the present invention has been described in detail with reference to several examples which, as a matter of course, are not intended to be limiting and can be modified or improved within the gist of the present invention.

EXAMPLES

The following examples are provided to further illustrate the present invention. It is to be understood, however, that the examples are for purpose of illustration only and are not intended as a definition of the limits of the invention.

Synthesis Example 1 (prior art)

Synthesis of N,N,N',N'-tetraethyl-p-phenylenediamine dihydrochloride (TEPD.2HCl)

p-Phenylenediamine (1 g), ethyl iodide (10.7 g) and sodium carbonate (4.4 g) were dissolved in methanol (10 ml) and refluxed over night. After cooling the reaction mixture to room temperature, the solvent was removed under a reduced pressure, and the resulting residue was mixed with acetone to remove insoluble materials by filtration. The solvent was removed from the thus obtained filtrate under a reduced pressure, and the resulting residue was recrystallized from an ethyl acetate-ether mixture solution to obtain 6.8 g of a quaternary ammonium salt.

Next, 6.8 g of the thus obtained quaternary ammonium salt and 12.5 g of sodium thiosulfate pentahydrate were dissolved in 50 ml of dimethylformamide and refluxed overnight. After cooling to room temperature, the reaction mixture was diluted with distilled water and extracted with toluene, the extracted layer was washed with water and dried on anhydrous sodium sulfate, and then the solvent was removed under a reduced pressure to obtain 1.0 g of TEPD. To the thus obtained TEPD was added 10 ml of ethanol, followed by dropwise addition of 5 ml 4N hydrochloric acid/ethyl acetate while cooling in an ice bath and subsequent 1 hour of stirring at 5° C. The thus formed precipitate was collected by filtration and washed with ethanol and ether to obtain 1.3 g of TEPD.2HCl.

Results of the following $^1$H NMR, IR (infrared absorption spectrum) and MS (mass spectrum) analyses confirmed that the thus obtained compound is the TEPD.2HCl of interest.

$^1$H NMR: δ1.2 (12H, t, J=7 Hz), 3.7 (8H, q, J=7 Hz), 7.9 (4H, S)

IR (cm$^{-1}$): 715, 840, 1020, 1276, 1516, 2420

MS: M$^+$−2HCl+1 221

Synthesis Example 2 (present invention)

Synthesis of N,N,N',N'-tetrakiscarboxymethyl-p-phenylenediamine (TCPD)

p-Phenylenediamine (1 g), chloroacetic acid (3.5 g), sodium hydroxide (3.1 g) and potassium iodide (460 mg) were dissolved in distilled water (46 ml) and refluxed for 1 hour. After cooling the reaction mixture to room temperature, 3.7 ml of concentrated hydrochloric acid was added dropwise while cooling in an ice bath. Thereafter, the thus formed precipitate was collected by filtration and recrystallized from a methanol-ethanol mixture solution to obtain 700 mg of TCPD.

Results of the following $^1$H NMR, IR and MS analyses confirmed that the thus obtained compound is the TCPD of interest.

$^1$H NMR: δ3.9 (8H, S), 6.3 (4H, S), 11.2 (4H, S)
IR (cm$^{-1}$): 700, 820, 1030, 1514, 1720, 2700, 3300
MS: M$^+$+1 341

Synthesis Example 3 (present invention)
Synthesis of N,N,N',N'-tetrakis-(2'-hydroxyethyl)-p-phenylenediamine dihydrochloride (THEPD.2HCl)

p-Phenylenediamine (1 g), 2-chloroethanol (3.0 g) and sodium hydroxide (1.5 g) were dissolved in distilled water (6 ml) and refluxed for 2 hours. After cooling the reaction mixture to room temperature, the solvent was removed under a reduced pressure, and the resulting residue was mixed with ethanol to remove insoluble materials by filtration. The solvent was removed from the thus obtained filtrate under a reduced pressure, and the resulting residue was purified by a silica gel column chromatography using a chloroform-methanol mixture as an eluting solution, thereby obtaining 1.5 g of THEPD.

Next, 1.5 g of the thus obtained THEPD was dissolved in 10 ml of ethanol to which was subsequently added dropwise 5 ml 4N hydrochloric acid/ethyl acetate while cooling in an ice bath, followed by 1 hour of stirring at 5° C. The thus formed precipitate was collected by filtration and washed with ethanol to obtain 1.1 g of THEPD.2HCl.

Results of the following $^1$H NMR, IR and MS analyses confirmed that the thus obtained compound is the THEPD.2HCl of interest.

$^1$H NMR: δ3.5 (16H, S), 7.0 (4H, m), 7.1 (4H, S)
IR (cm$^{-1}$): 720, 890, 1020, 1210, 1390, 1500, 2700, 3300
MS: M$^+$−2HCl+1 285

Synthesis Example 4 (present invention)

Synthesis of N,N,N',N'-tetrakis-(2',3'-dihydroxypropyl)-p-phenylenediamine dihydrochloride (TDHPD.2HCl)

p-Phenylenediamine (1 g), 3-chloro-1,2-propanediol (4.6 g) and sodium hydroxide (1.64 g) were dissolved in distilled water (30 ml) and refluxed for 2 hours. After cooling the reaction mixture to room temperature, the solvent was removed under a reduced pressure, and the resulting residue was mixed with ethanol to remove insoluble materials by filtration. The solvent was removed from the thus obtained filtrate under a reduced pressure, and the resulting residue was purified by a silica gel column chromatography using a chloroform-methanol mixture as an eluting solution, thereby obtaining 1.1 g of TDHPD.

Next, 1.1 g of the thus obtained TDHPD was dissolved in 10 ml of ethanol to which was subsequently added dropwise 5 ml 4N hydrochloric acid/ethyl acetate while cooling in an ice bath, followed by 1 hour of stirring at 5° C. The thus formed precipitate was collected by filtration and washed with ethanol to obtain 820 mg of TDHPD.2HCl.

Results of the following $^1$H NMR, IR and MS analyses confirmed that the thus obtained compound is the TDHPD.2HCl of interest.

$^1$H NMR: δ3.7 (20H, m), 7.1 (4H, S)
IR (cm$^{-1}$): 720, 870, 1040, 1260, 1370, 1520, 3300
MS: M$^+$−2HCl+1 405

Synthesis Example 5 (present invention)

Synthesis of N-2'-hydroxyethyl-,N,N',N'-triethyl-p-phenylenediamine dihydrochloride (HTEPD.2HCl)

`A 12.8 g portion of potassium carbonate was added to 100 ml of methanol solution containing 5 g of p-phenylenediamine, and 14.4 g of ethyl iodide was added dropwise to the resulting solution spending 10 minutes at room temperature. The reaction solution was stirred at 50° C. until disappearance of the starting material was confirmed by a thin layer chromatography (chloroform:methanol=10:1) and then concentrated under a reduced pressure.

The thus concentrated residue was dissolved in a n-hexane:ethyl acetate (1:1) mixture, precipitated crystals were filtered off, and the resulting filtrate was concentrated under a reduced pressure. The resulting residue was purified by a silica gel column chromatography (n-hexane:ethyl acetate= 1:1) to obtain 1.5 g of N,N',N'-triethyl-p-phenylenediamine.

Next, 1.5 g of the thus obtained N,N',N'-triethyl-p-phenylenediamine was dissolved in 20 ml of n-butanol to which was subsequently added 2.2 g of sodium hydroxide. To the resulting solution was added dropwise 4.4 g of 2-chloroethanol at room temperature spending 5 minutes, followed by 1 hour of reflux. After confirming disappearance of the starting material by a thin layer chromatography (n-hexane:ethyl acetate=1:1), the reaction solution was cooled to room temperature and filtered off precipitated crystals. The resulting residue was purified by a silica gel column chromatography (n-hexane:ethyl acetate=1:1) to obtain HTEPD.

Thereafter, the thus obtained HTEPD was dissolved in 15 ml of ethanol, 2.4 ml of 4N hydrochloric acid/ethyl acetate was added dropwise to the resulting solution which was cooled in an ice bath, and then the thus formed crystals were washed with ethanol to obtain 1.0 g of HTEPD.2HCl.
Spectral data of HTEPD.2HCl
$^1$H NMR: δ1.1 (9H, t, J=7 Hz), 3.5 (10H, m), 7.4 (4H, m)
IR (cm$^{-1}$): 700, 830, 1060, 1370, 1450, 1500, 2350, 2900, 3350
MS (M$^+$–2HCl+1): 237

Synthesis Example 6 (present invention)

Synthesis of N,N-bis-(2'-hydroxyethyl)-N',N'-diethyl-p-phenylenediamine dihydrochloride (N,N-BHDPD.2HCl)

A 3.7 g portion of sodium hydroxide was added to 30 ml of n-butanol solution containing 5 g of N,N-diethyl-p-phenylenediamine, and 7.3 g of 2-chloroethanol was added dropwise to the resulting solution spending 10 minutes at room temperature. The reaction solution was refluxed for 4 hours. After confirming disappearance of the starting material by a thin layer chromatography (chloroform:methanol= 10:1), the reaction solution was cooled to room temperature. Crystals thus precipitated were filtered off, the resulting filtrate was concentrated under a reduced pressure and then the resulting residue was purified by a silica gel column chromatography (chloroform:methanol=10:1) to obtain N,N-BHDPD.

Thereafter, the thus obtained BHDPD was dissolved in 20 ml of ethanol, 2.74 ml of 4N hydrochloric acid/ethyl acetate was added dropwise to the resulting solution which was cooled in an ice bath, and then the thus formed crystals were washed with ethanol to obtain 1.22 g of BHDPD.2HCl.
Spectral data of BHDPD.2HCl
$^1$H NMR: δ1.0 (6H, t, J=7 Hz), 3.5 (12H, m), 6.7 (2H, d, J=9 Hz), 7.5 (2H, d, J=9 Hz)
IR (cm$^{-1}$): 700, 830, 1050, 1380, 1450, 1500, 2480, 2900, 3300
MS (M$^+$–2HCl+1): 253

Synthesis Example 7 (present invention)

Synthesis of N,N'-bis-(2'-hydroxyethyl)-p-phenylenediamine (N,N'-BHPD)

A 4.4 g portion sodium hydroxide was added to 100 ml of ethanol solution containing 5 g of p-phenylenediamine, and heated to 55° C. Thereafter, 8.9 g of 2-chloroethanol was added dropwise to the resulting solution spending 10 minutes. The reaction solution was refluxed overnight. After confirming disappearance of the starting material by a thin layer chromatography (chloroform:methanol=10:1), the reaction solution was cooled to room temperature.

The precipitated crystals were filtered off, and the resulting filtrate was concentrated under a reduced pressure. The resulting residue was purified by a silica gel column chromatography (chloroform:methanol=10:1) to obtain 5.0 g of purified N,N'-BHPD.

Synthesis Example 8 (present invention)

Synthesis of N,N'-bis-(2'-hydroxyethyl)-N,N'-diethyl-p-phenylenediamine dihydrochloride (N,N'-BHDPD)

A 8.9 g portion potassium carbonate was added to 100 ml of ethanol solution containing 4.5 of BHPD, and 9.5 g of ethyl iodide was added to the resulting solution. The reaction solution was refluxed overnight. After confirming disappearance of the starting material by a thin layer chromatography (chloroform:methanol=5:1), the reaction solution was cooled to room temperature.

The precipitated crystals were filtered off, and the resulting filtrate was concentrated under a reduced pressure. The resulting residue was purified by a silica gel column chromatography (ethyl acetate 100%) to obtain 233 mg of N,N'-BHDPD. Next, the thus obtained N,N'-BHDPD was dissolved in 5 ml of ethanol to which was subsequently added dropwise 10% hydrogen chloride/methanol under ice-cooling to precipitate crystals. The crystals were separated by filtration to obtain 266 mg of N,N'-BHDPD.2HCl.
Spectral data of N,N'-BHDPD.2HCl
$^1$H NMR: δ1.1 (6H, t, J=7 Hz), 3.5 (12H, m), 7.4 (4H, s)
IR (cm$^{-1}$): 670, 830, 1070, 1500, 2500, 2900, 3350
MS (M$^+$–2HCl+1): 253

Synthesis Example 9 (present invention)

Synthesis of p-phenylenediamine derivatives having substituted amino group by reacting p-phenylenediamine with propyleneoxide A 1.3 g portion of sodium hydroxide was further added to 100 ml of methanol solution containing 5 g of p-phenylenediamine, and 1.1 g of propyleneoxide was added dropwise to the resulting solution. The reaction solution was stirred overnight at 30° C. and then concentrated under a reduced pressure. To the concentrate was added chloroform to obtain 7 g of a chloroform-extracted product.

A HPLC separation of the chloroform-extracted product was conducted by use of eluent (acetonitrile:50 mM ammonium acetate=15.6:84.4) and an ODS column (YMC-Pack ODS, 20 mm Φ×250 mm; produce of YMC Co.), in which the flow rate was 15 ml/min and the detecting wavelength was 254 nm.

As the result, p-phenylenediamine derivatives having mono-, di- and tri-substituted amino group(s) were obtained. Each substitution was confirmed by $^1$HNMR and MS analyses. mono-substituted $^1$H NMR: δ1.1 (3H, d, J=6 Hz), 2.8 (2H, m), 3.8 (1H, m), 4.9 (3H, brS), 6.4 (4H, m) [MS 167 (M+1)] di-substituted [MS 225 (M+1)] tri-substituted [MS 283 (M+1)] And p-phenylene diamine drivative having monosubstituted amino group was confirmed as N-2'-hydroxypropyl-phenylenediamine (HPPD) by above data.

Test Example 1

Measurement of vapor pressures of p-phenylenediamine(PPD), N,N,N',N'-tetramethyl-p-phenylenediamine (TMPD), TEPD, TCPD, THEPD and TDHPD The PPD(manufactured by Wakoh Junyaku K.K), TMPD (manufactured by Tokyo Kasei K.K), further, TEPD, TCPD, THEPD and TDHPO obtained in the course of the procedures of Synthesis Examples 1 to 4 were checked for their vapor pressures.

Vapor densities (amount of evaporation/volume) of the solid samples (PPD, TMPD, TEPD, TCPD, THEPD and TDHPD) were measured by contacting each sample heated to a predetermined temperature with a stream of carrier gas (nitrogen) and saturating the sample with vapor, and vapor pressures of TEPD and THEPD were calculated from the data on an assumption that the vapor follows the law of ideal gas (gas flow method). The vapor density was calculated by measuring evaporation rate (loss rate) of each sample using an electric balance, and the carrier gas flow rate using a flow meter.

The vapor pressure was calculated from the vapor density based on the following formula.

$$P = (k/v)V\pi/M$$

In the above formula, P represents vapor pressure (mmHg), k represents evaporation rate (mg/min), v represents carrier gas flow rate (ml/min), k/v represents vapor density (mg/ml), M represents molecular weight of each sample, $\pi$ represents pressure of the system (mmHg) and V represents molar volume of carrier gas (l/mol).

Figure 5:
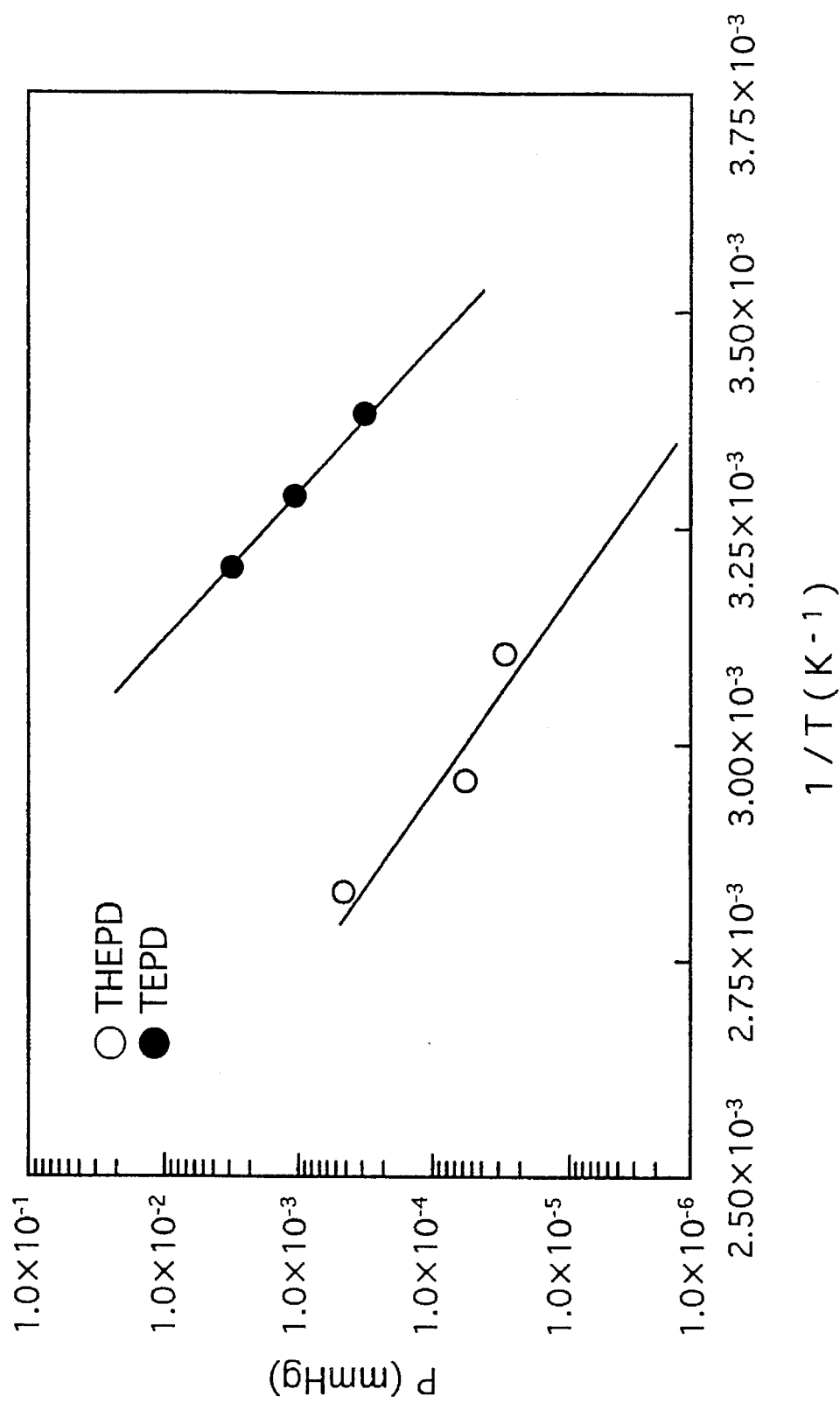
FIG. 5 is a graph showing vapor pressures of TEPD and THEPD.

Vapor pressure profiles of TEPD and THEPD at each temperature are shown in FIG. 5.

Figure 24:
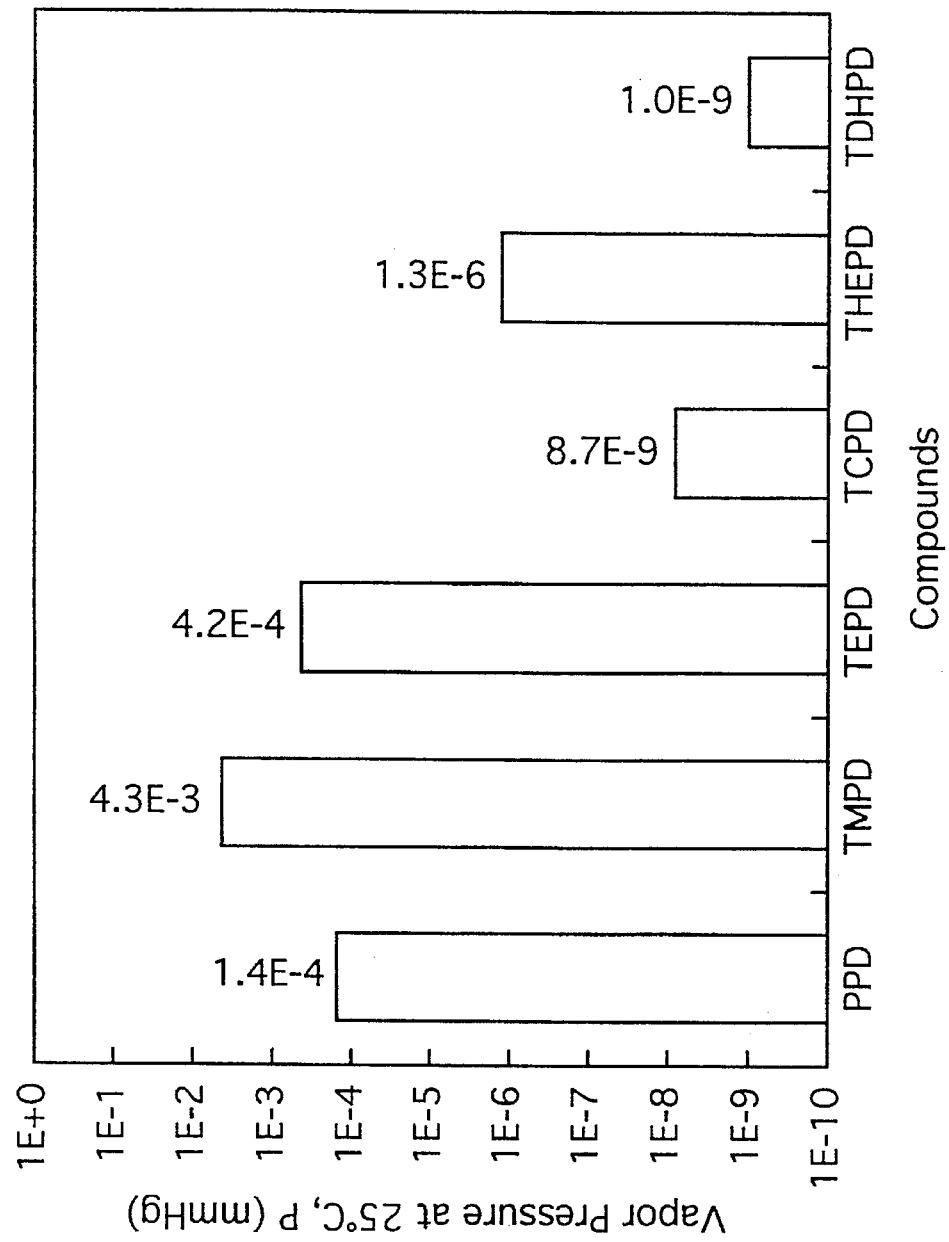
FIG. 24 is a graph showing vapor pressures of PPD, TMPD TEPD, TCPD, THEPD and TDHPD at 25° C.

Vapor pressure curves of the compounds at 25° C. are shown in FIG. 24.

As is evident from FIGS. 5 and 24, the vapor pressures of TEPD, TCPD, THEPD and TDHPD at 25° C. are $4.2 \times 10^{-4}$ mmHg, $8.7 \times 10^{-9}$ mmHg, $1.3 \times 10^{-6}$ mmHg and $1.0 \times 10^{-9}$ mmHg, respectively, showing that the vapor pressures of TCPD, THEPD and TDHPD is about 50,000 times, about 300 times, and about 420,000 times lower than that of TEPD, respectively. These results show that the property in drying (freeze-drying, vacuum drying, air-drying or the like) and stability of dried states of TCPD, THEPD and TDHPD are superior to those of PPD, TMPD and TEPD.

Test Example 2

Measurement of cyclic voltammetry (CV) of TEPD.2HCl, TCPD, THEPD.2HCl, TDHPD.2HCl, HTEPD.2HCl, N,N-BHDPD.2HCl, N,N'-BHDPD.2HCl, and p-phenylenediamine derivatives having substituted amino group by reacting p-phenylenediamine with propyleneoxide ("2HCl" is omitted in the following)

Each of TEPD, TCPD, THEPD, TDHPD, HTEPD, N,N-BHDPD, N,N'-BHDPD, and p-phenylenediamine derivatives having substituted amino group by reacting p-phenylenediamine with propyleneoxide obtained in Synthesis Examples 1 to 9 was dissolved in 0.1M phosphate buffer (pH 6.0) containing 0.1M NaCl, and CV of the thus prepared $5.0 \times 10^{-4}$M solutions were measured. A glassy carbon electrode (MF2012 manufactured by BIOANALYTICAL SYSTEMS) used as a working electrode, an Ag/AgCl electrode (MF2020 manufactured by BIOANALYTICAL SYSTEMS) used as a reference electrode and a platinum wire (manufactured by BIOANALYTICAL SYSTEMS) used as a counter electrode were connected to a potentiostat HA-150 (manufactured by Hokuto Denko) to which were further connected a function generator HB-104 (manufactured by Hokuto Denko) for use in the setting of electrode potential and a recorder. The recorder was connected to a computer via a GPIB line to carry out measurement recording and data processing. Measurement of the CV was carried out by setting the initial potential to −500 mV (vs Ag/AgCl, the same shall apply hereinafter) and the reverse potential to +800 mV, or the initial potential to −200 mV and the reverse potential to +300 mV, and by effecting potentional sweep at a rate of 50 mV/sec.

Figure 6:
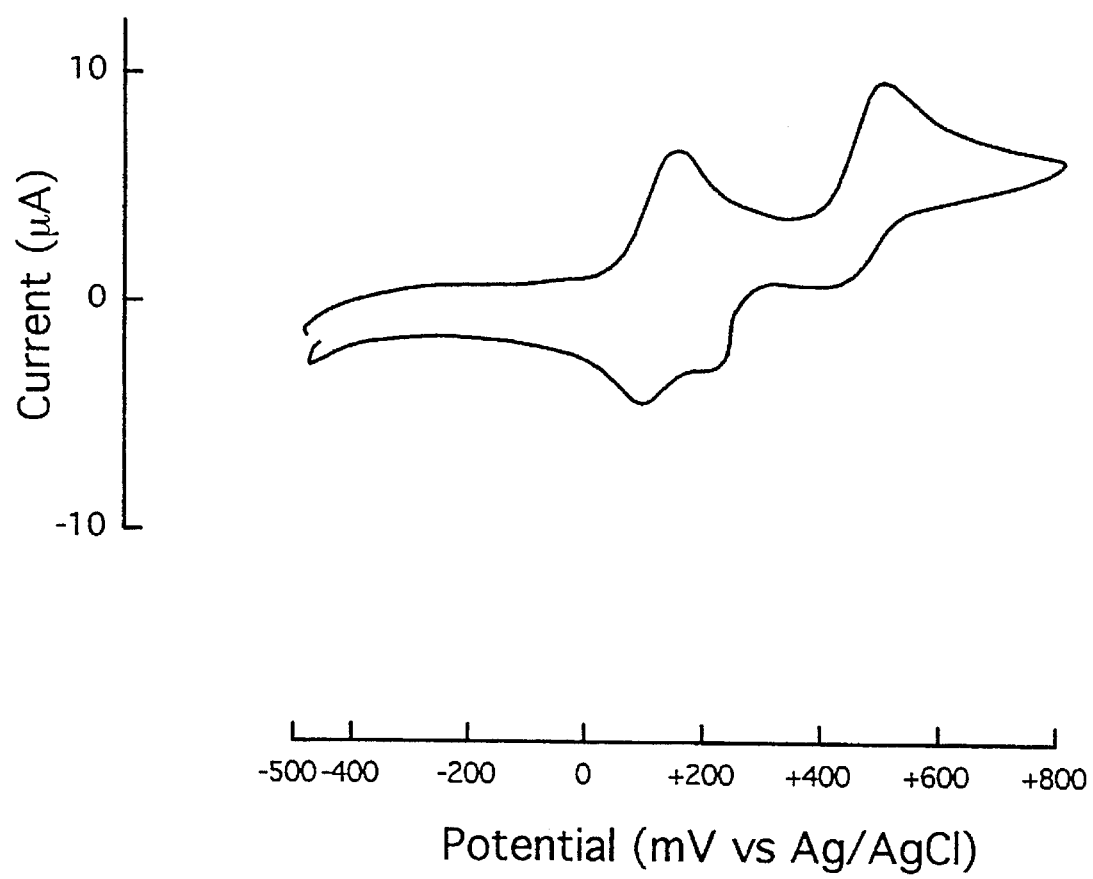
FIG. 6 is a graph showing cyclic voltammetry (potential scanning range, −500 mV to +800 mV) of TEPD.
Figure 7:
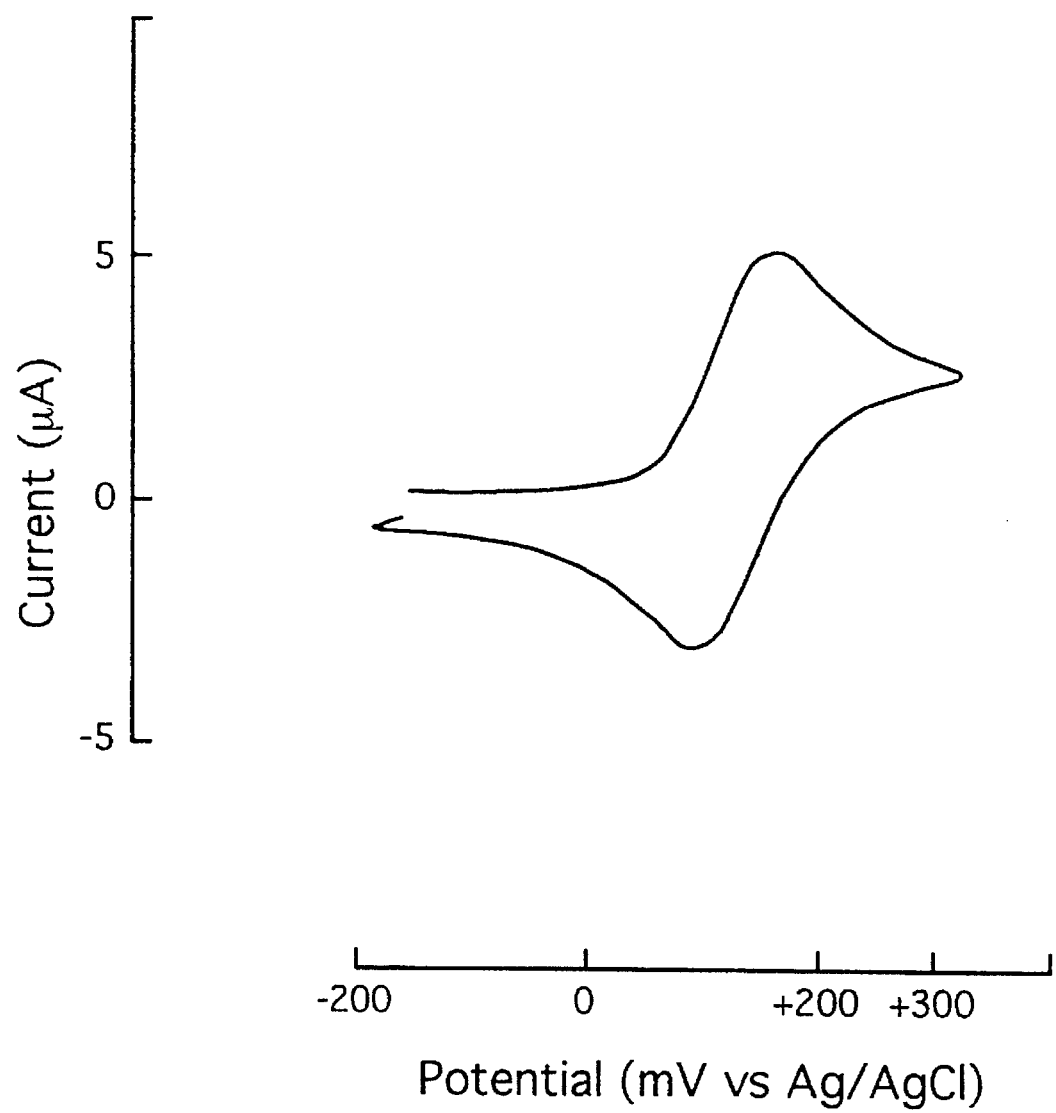
FIG. 7 is a graph showing cyclic voltammetry (potential scanning range, −200 mV to +300 mV) of TEPD.
Figure 8:
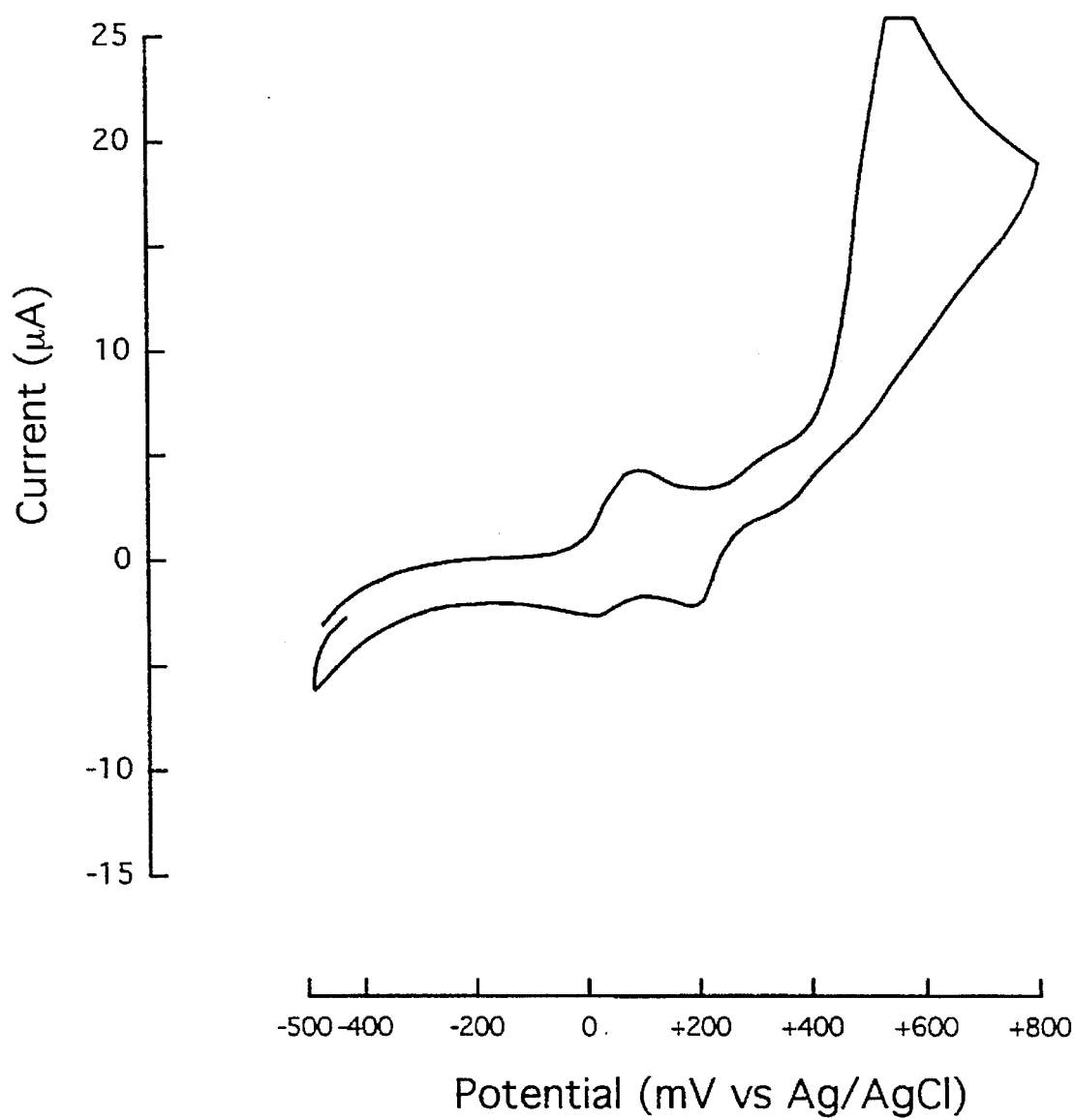
FIG. 8 is a graph showing cyclic voltammetry (potential scanning range, −500 mV to +800 mV) of TCPD.
Figure 9:
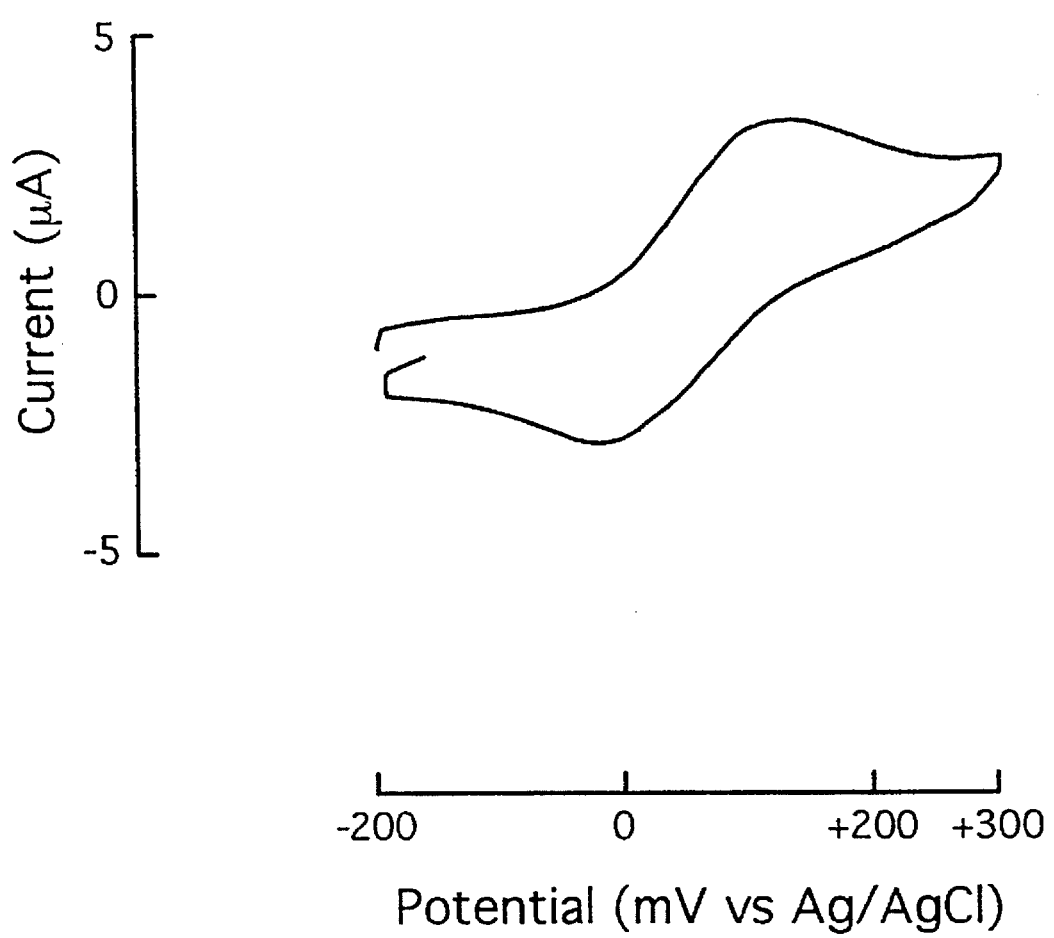
FIG. 9 is a graph showing cyclic voltammetry (potential scanning range, −200 mV to +300 mV) of TCPD.
Figure 10:
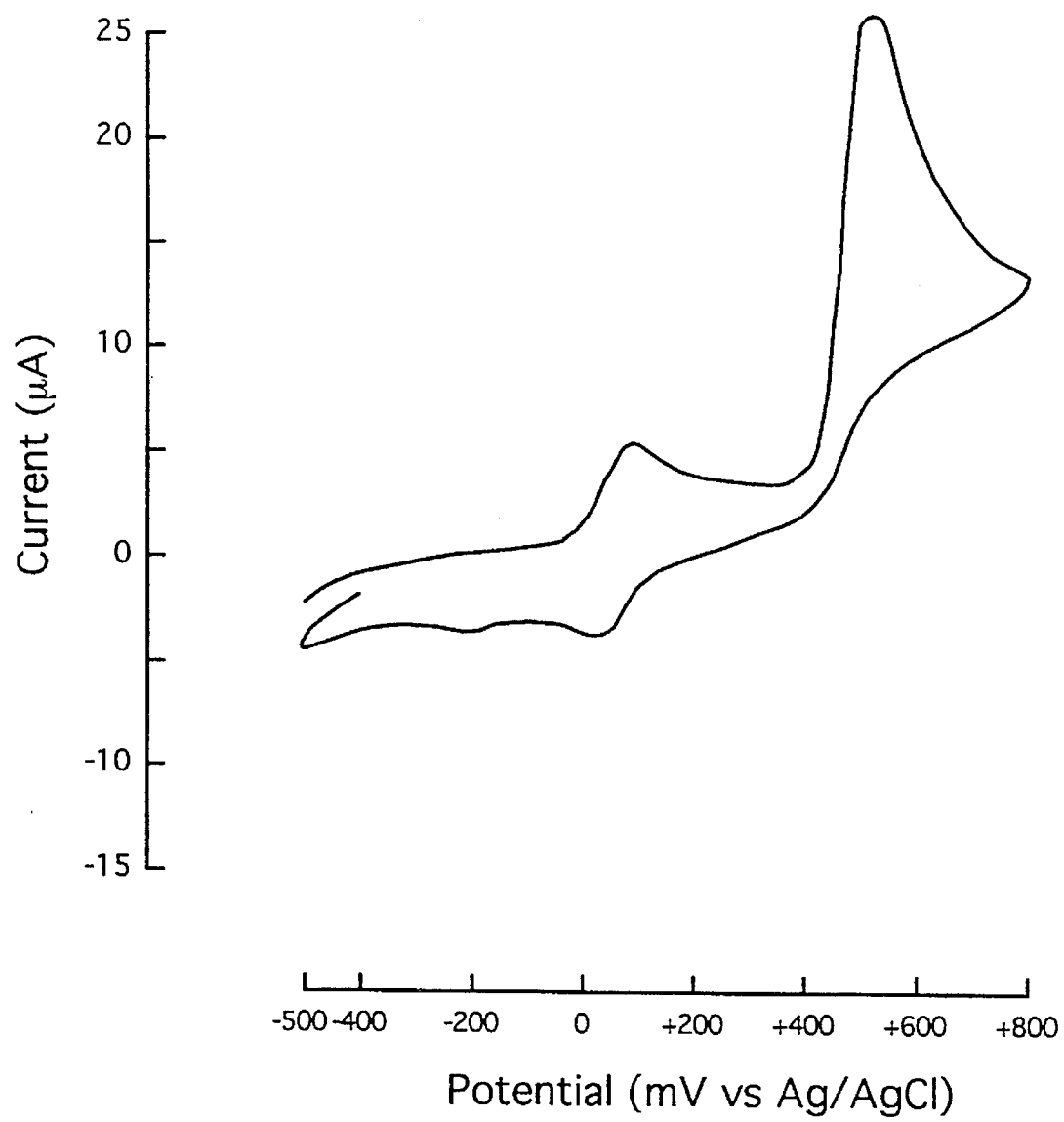
FIG. 10 is a graph showing cyclic voltammetry (potential scanning range, −500 mV to +800 mV) of THEPD.
Figure 11:
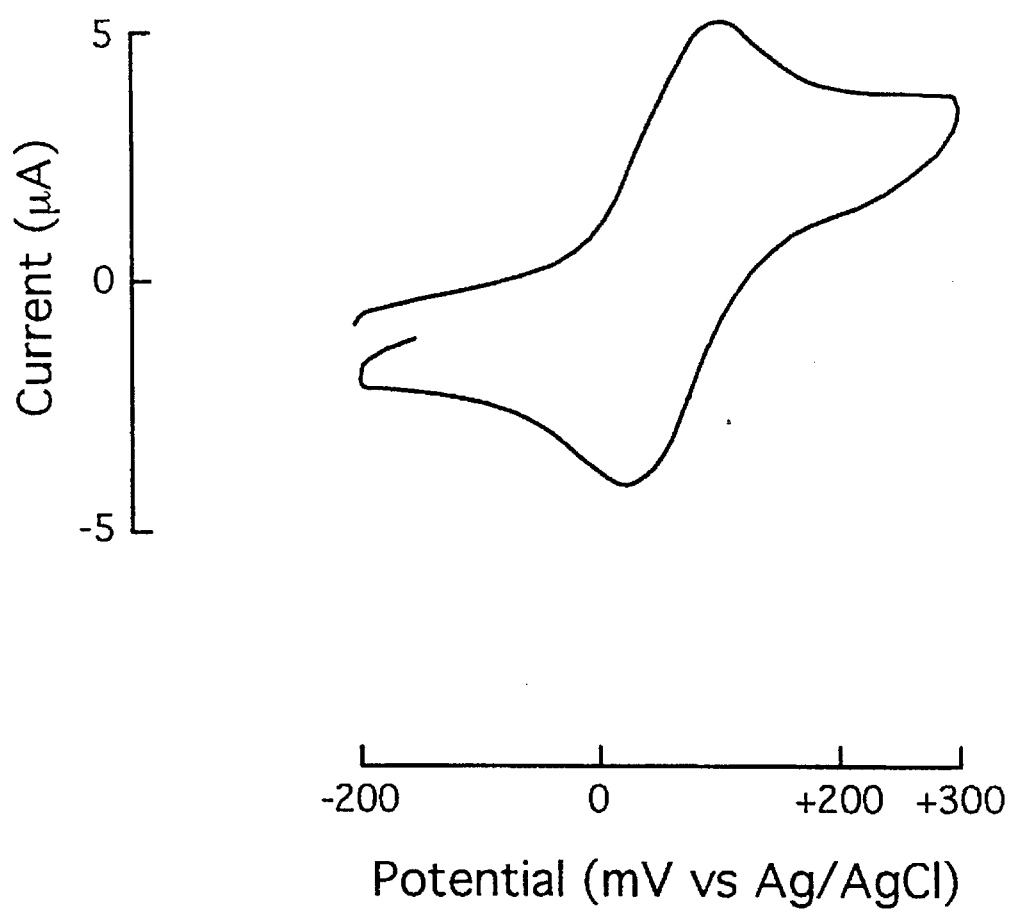
FIG. 11 is a graph showing cyclic voltammetry (potential scanning range, −200 mV to +300 mV) of THEPD.
Figure 12:
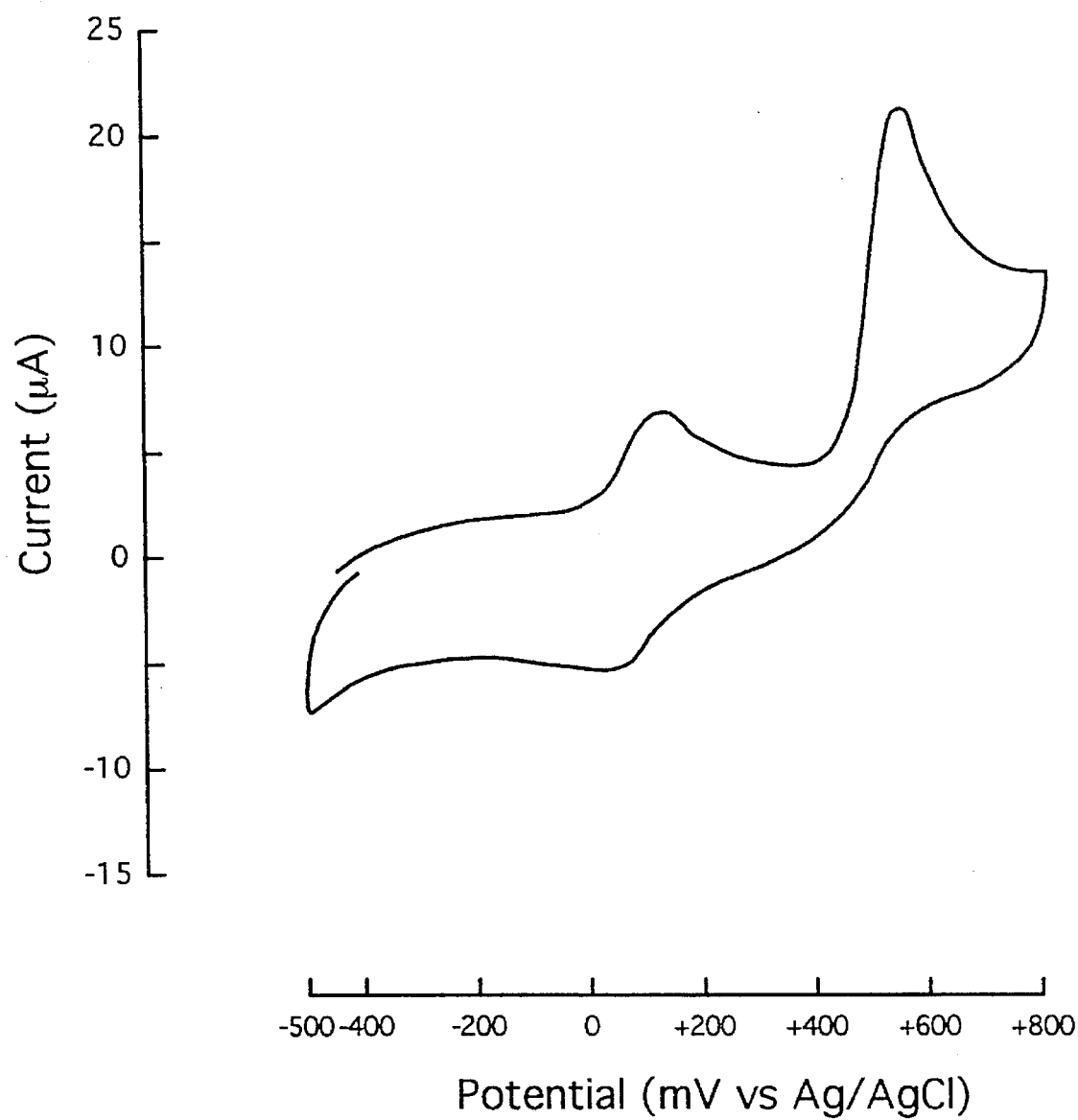
FIG. 12 is a graph showing cyclic voltammetry (potential scanning range, −500 mV to +800 mV) of TDHPD.
Figure 13:
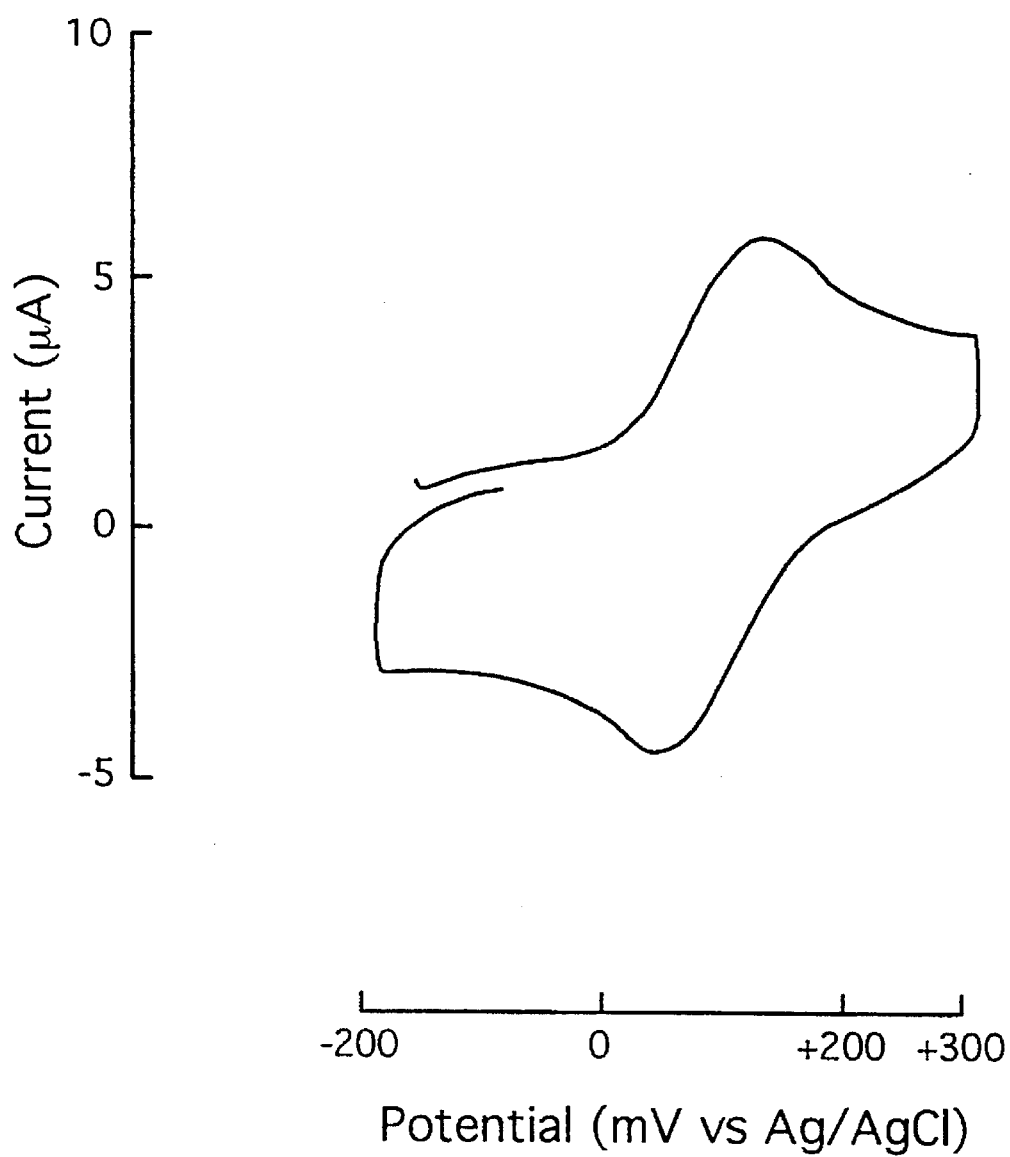
FIG. 13 is a graph showing cyclic voltammetry (potential scanning range, −200 mV to +300 mV) of TDHPD.
Figure 25:
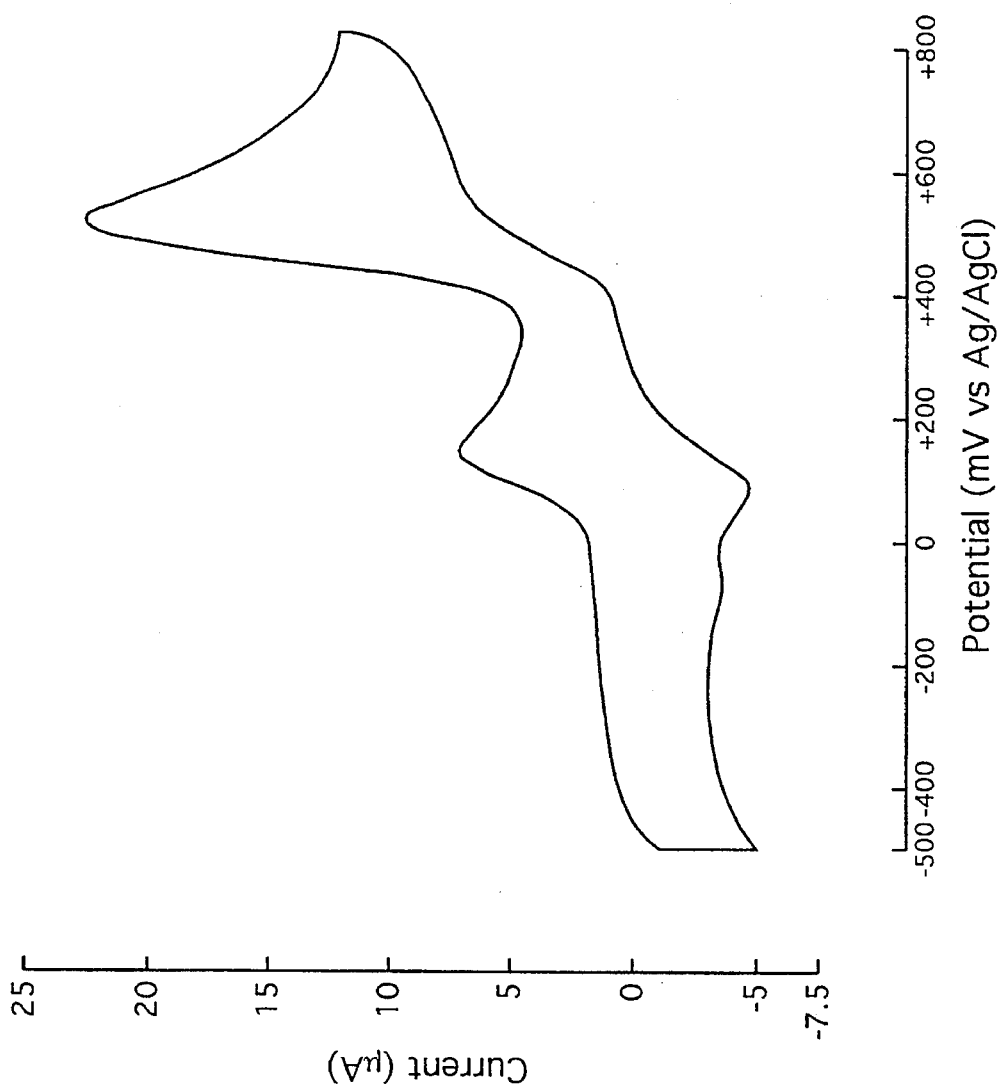
FIG. 25 is a graph showing cyclic volutammetry (potential scanning range, −500 mV to +800 mV) of HTEPD.
Figure 26:
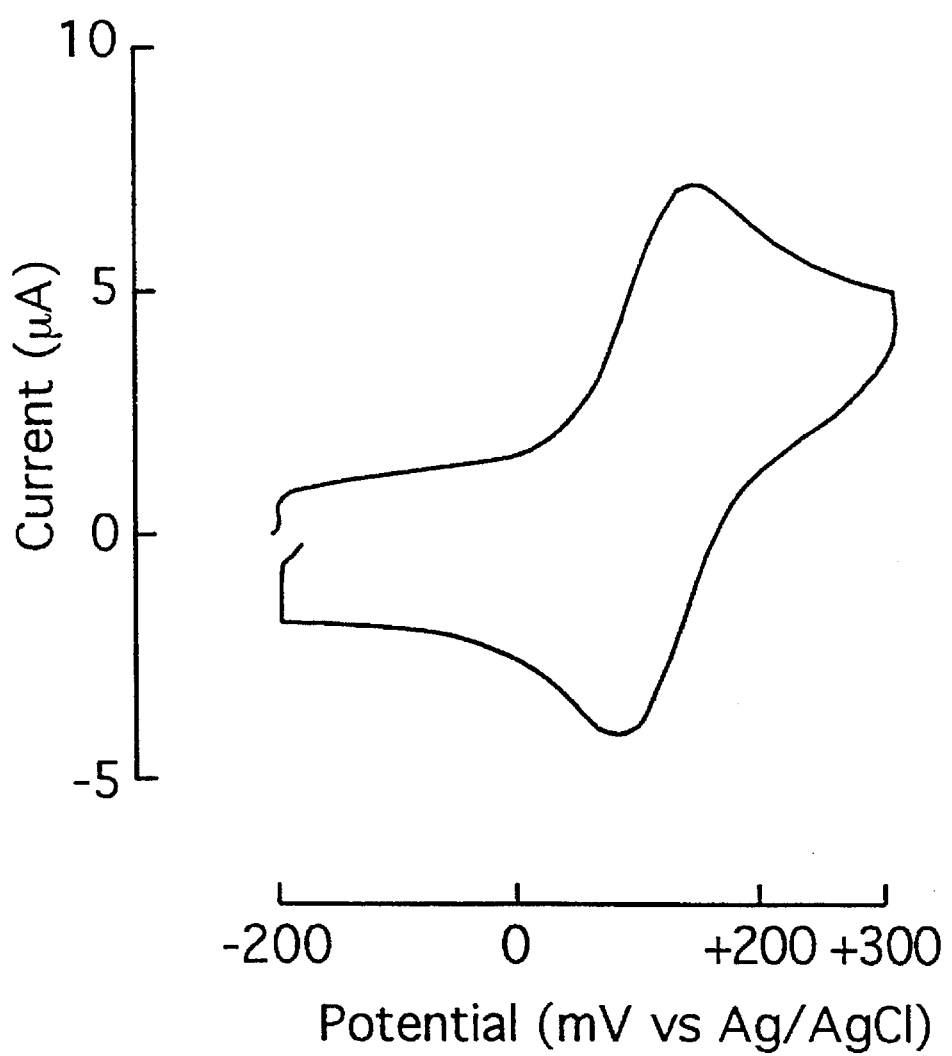
FIG. 26 as a graph showing cyclic volutammetry (potential scanning range, −200 mV to +300 mV) of HTEPD.
Figure 27:
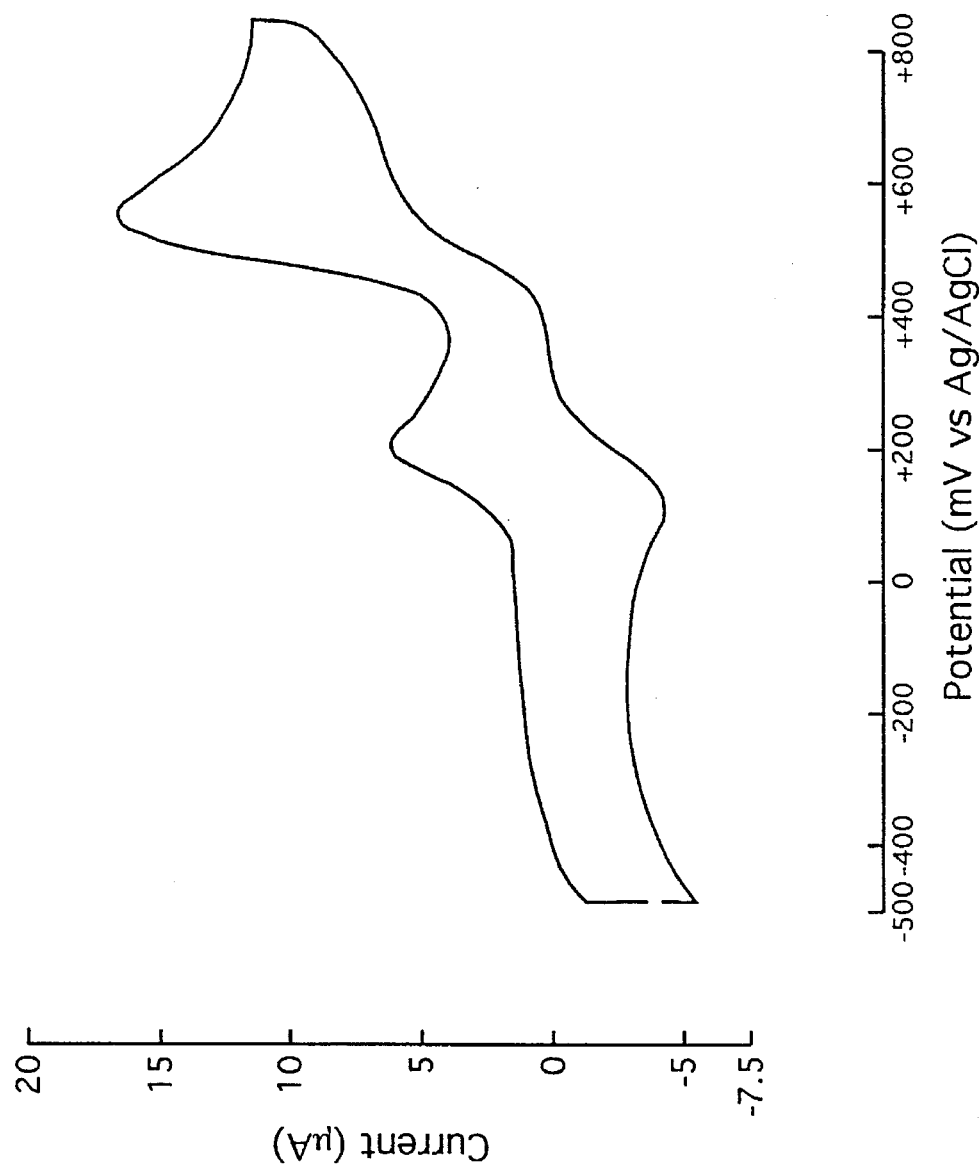
FIG. 27 as a graph showing cyclic volutammetry (potential scanning range, −500 mV to +800 mV) of N,N-BHDPD.
Figure 28:
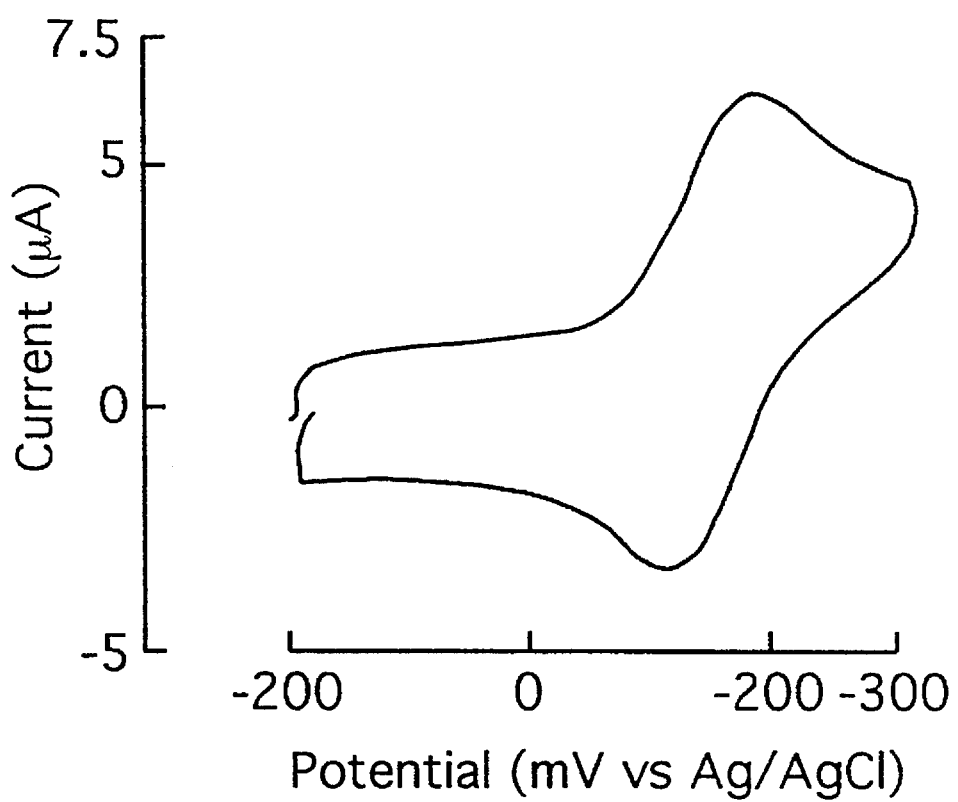
FIG. 28 is a graph showing cyclic volutammetry (potential scanning range, −200 mV to +300 mV) of N,N-BHDPD.
Figure 29:
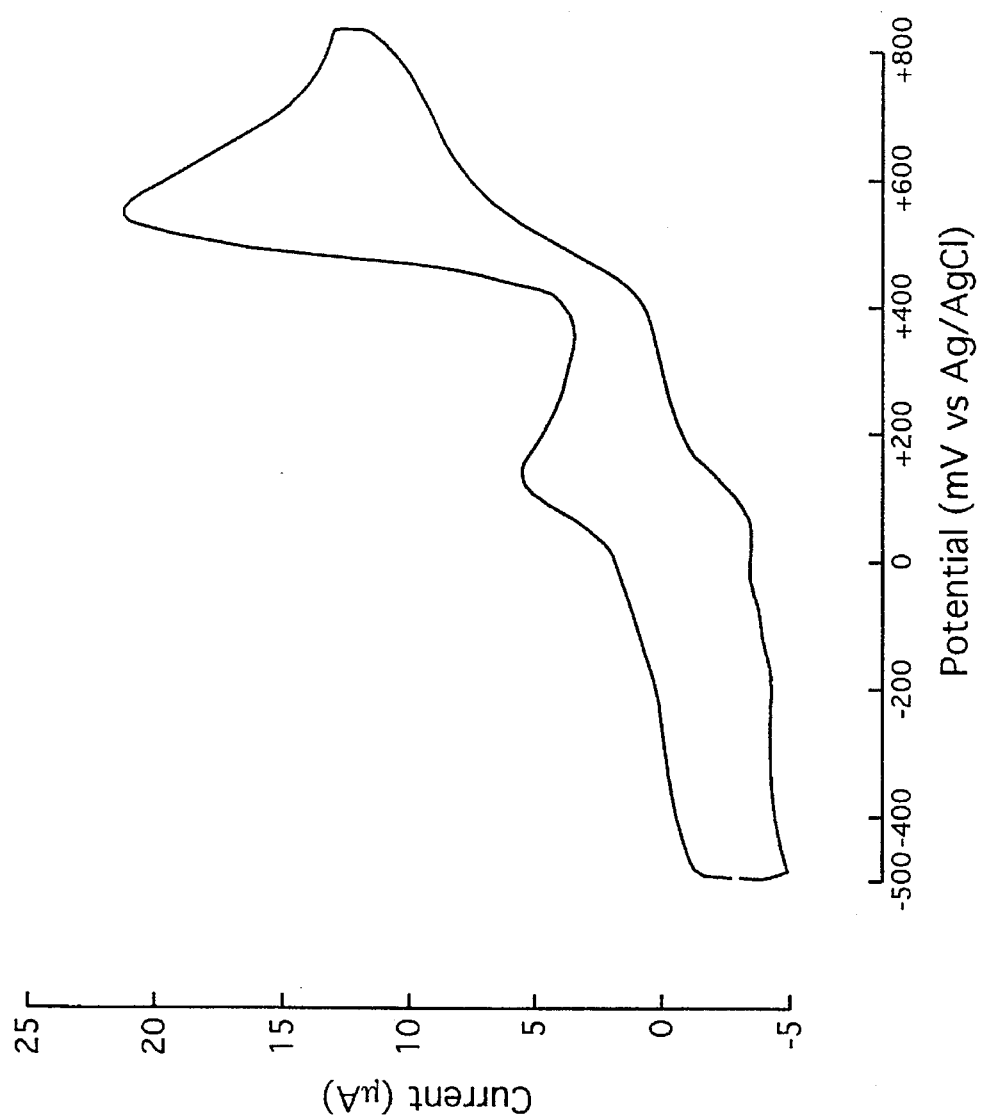
FIG. 29 is a graph showing cyclic volutammetry (potential scanning range, −500 mV to +800 mV) of N,N'-BHDPD.
Figure 30:
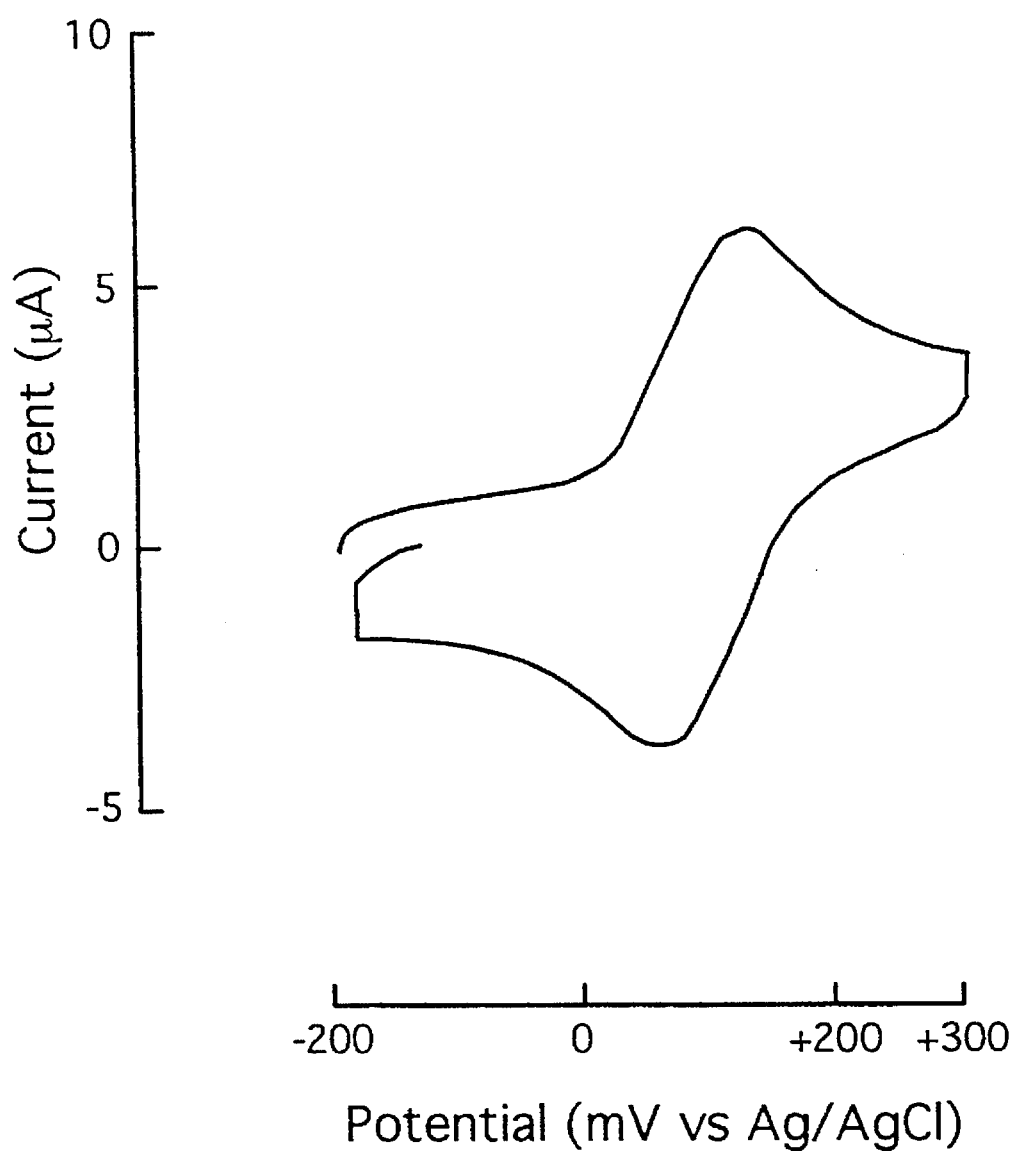
FIG. 30 is a graph showing cyclic volutammetry (potential scanning range, −200 mV to +300 mV) of N,N'-BHDPD.
Figure 31:
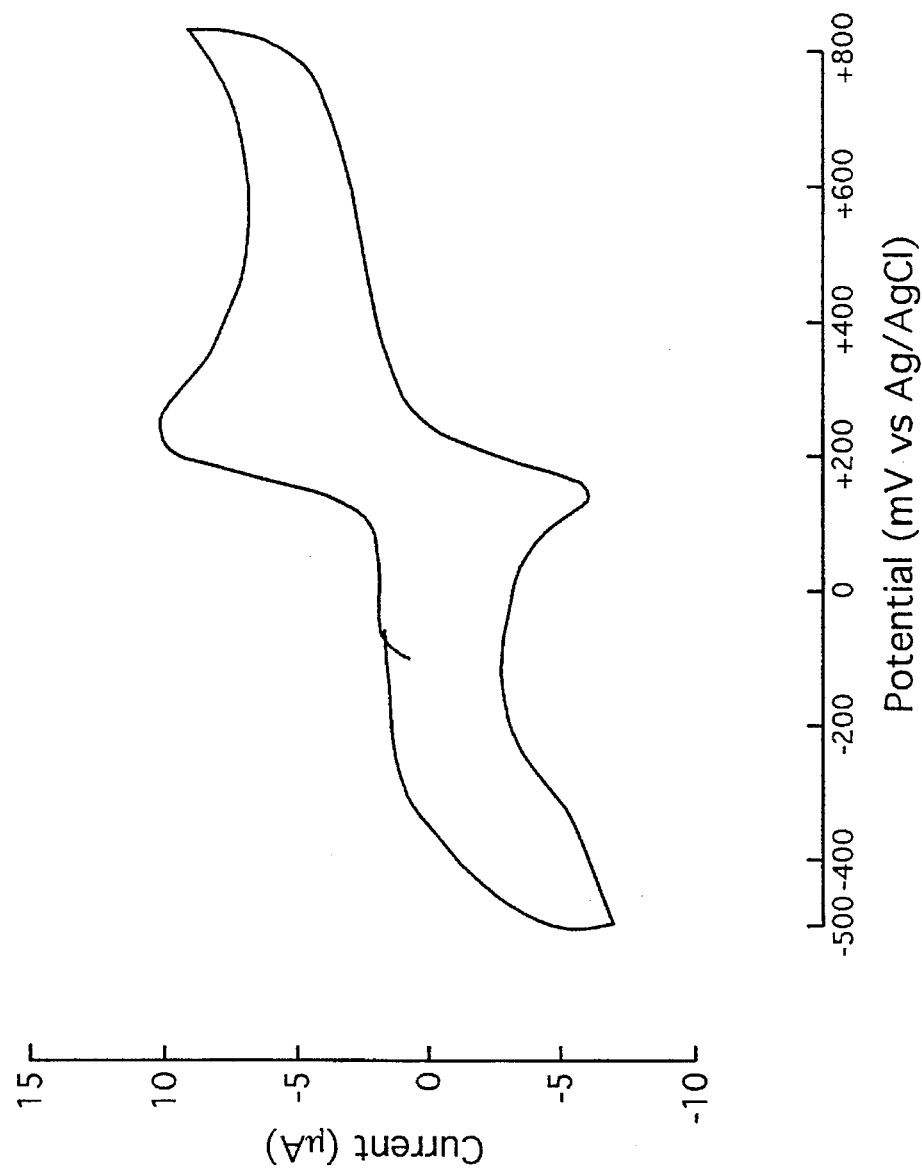
FIG. 31 is a graph showing cyclic volutammetry (potential scanning range, −500 mV to +800 mV) of p-phenylenediamine derivative having mono-substituted an amino group obtained from the reaction of p-phenylenediamine with propyleneoxide (HPPD).
Figure 32:
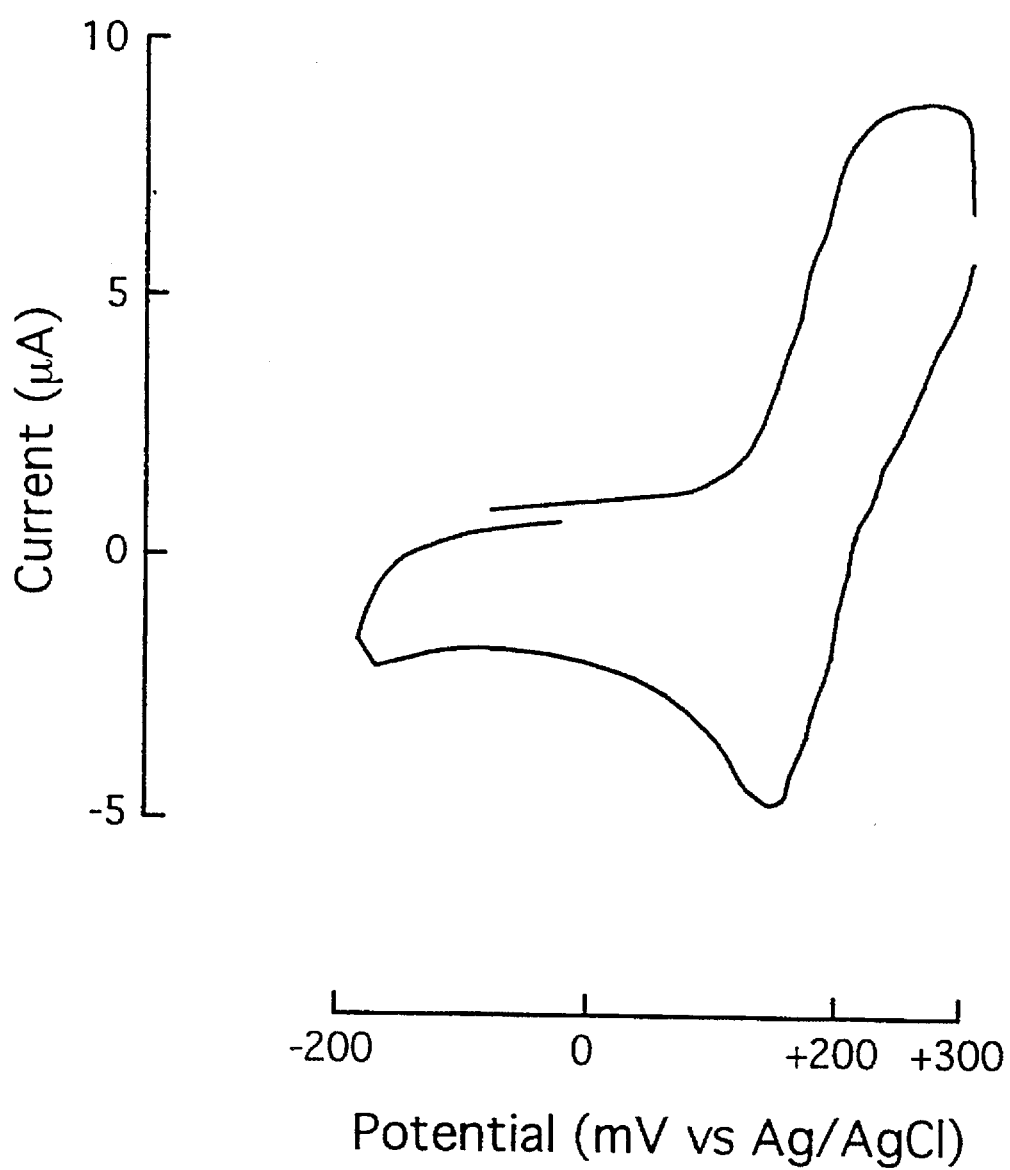
FIG. 32 is a graph showing cyclic volutammetry (potential scanning range, −200 mV to +300 mV) of p-phenylenediamine derivative having mono-substituted an amino group obtained from the reaction of p-phenylenediamine with propyleneoxide (HPPD).
Figure 33:
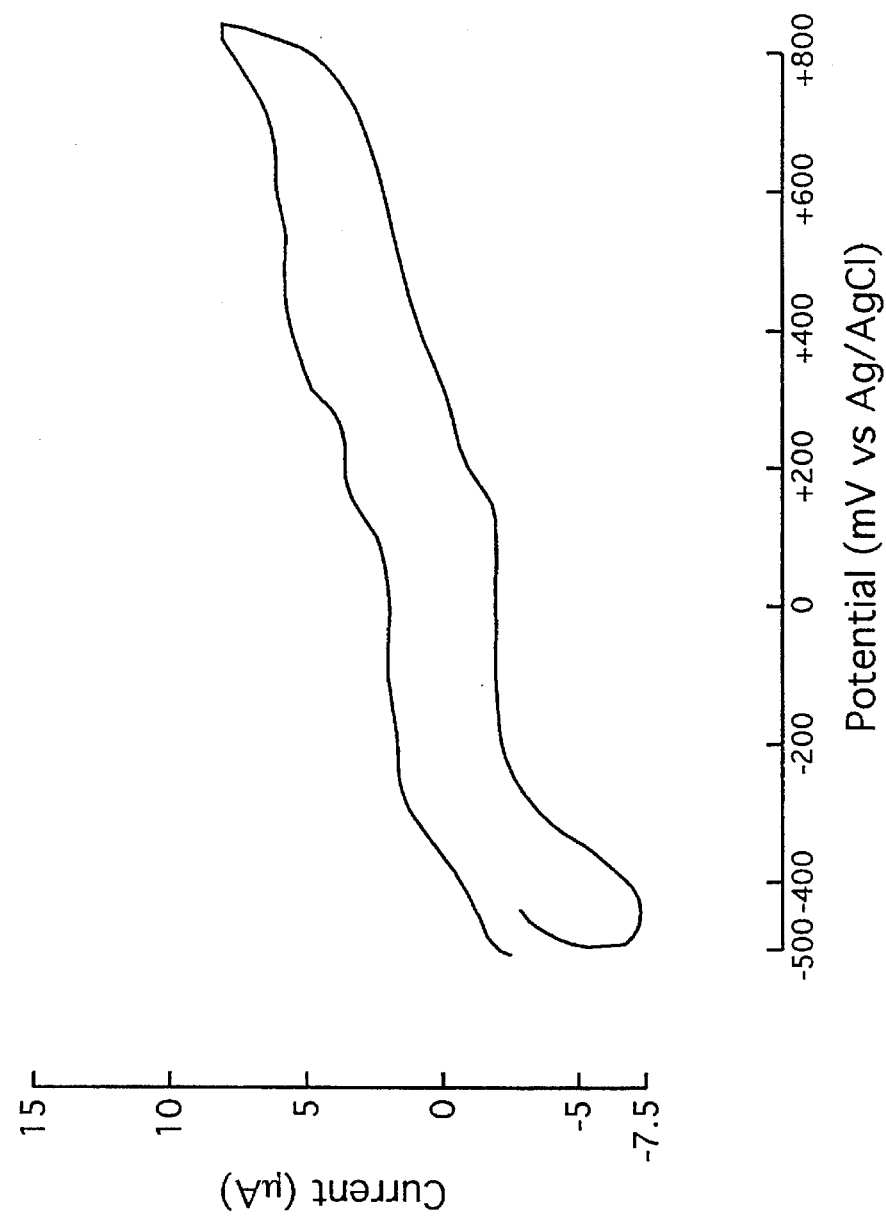
FIG. 33 is a graph showing cyclic volutammetry (potential scanning range, −500 mV to +800 mV) of p-phenylenediamine derivative having di-substituted an amino group or two amino groups obtained from the reaction of p-phenylenediamine with propyleneoxide.
Figure 34:
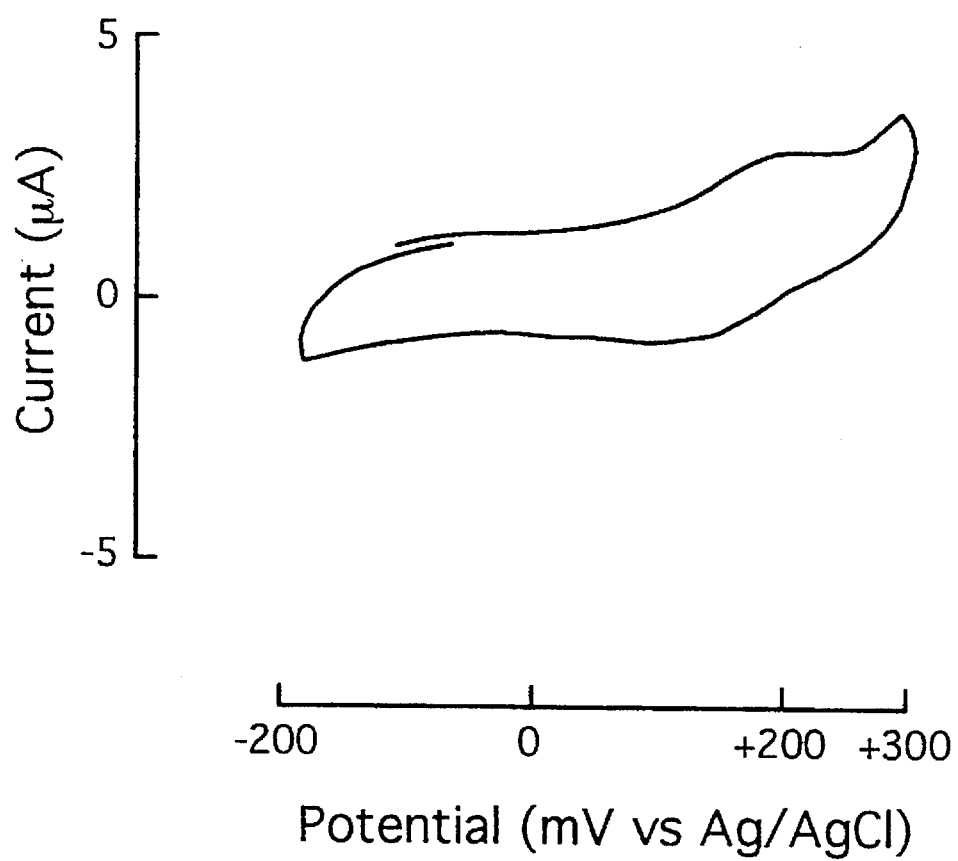
FIG. 34 is a graph showing cyclic volutammetry (potential scanning range, −200 mV to +300 mV) of p-phenylenediamine derivative having di-substituted an amino group or two amino groups obtained from the reaction of p-phenylenediamine with propyleneoxide.
Figure 35:
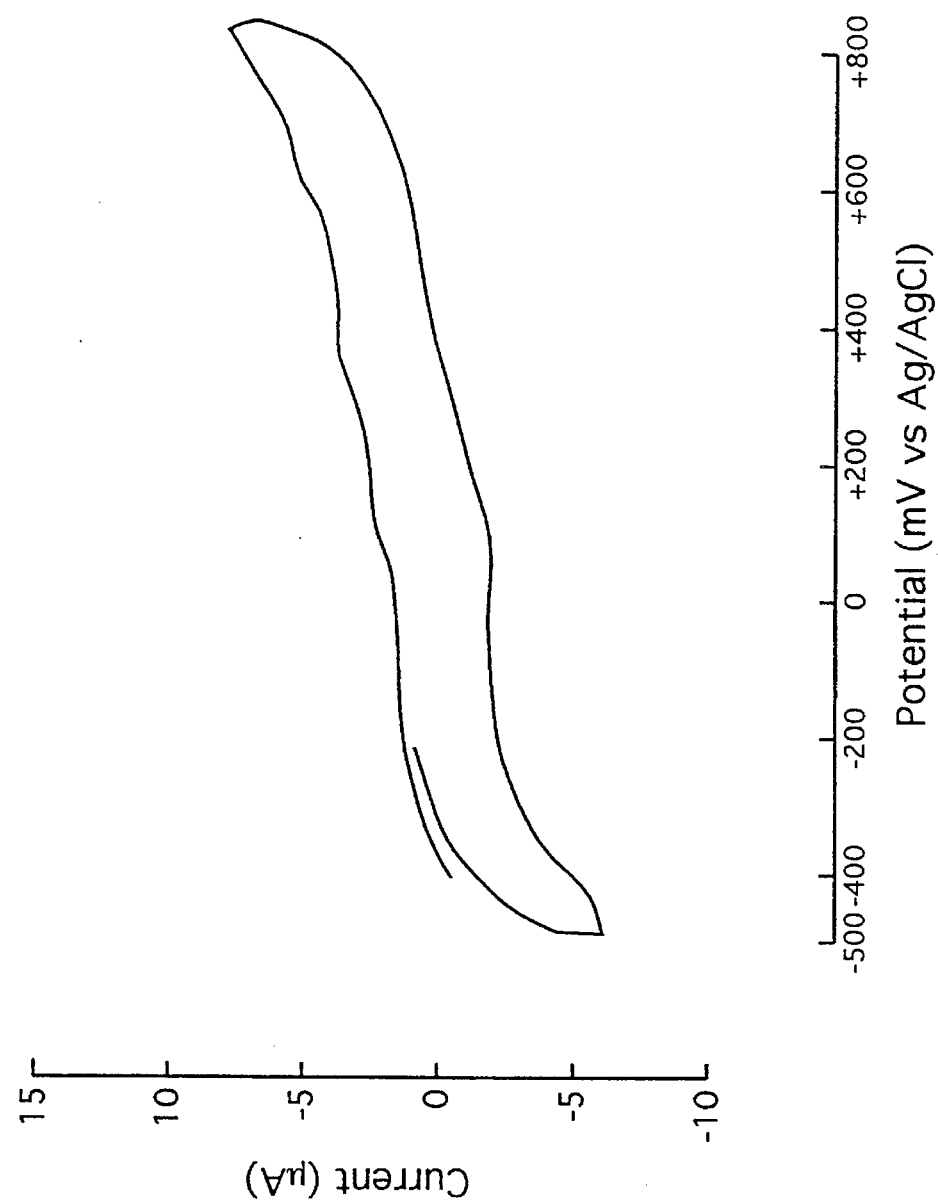
FIG. 35 is a graph showing cyclic volutammetry (potential scanning range, −500 mV to +800 mV) of p-phenylenediamine derivative having tri-substituted amino groups obtained from the reaction of p-phenylenediamine with propyleneoxide.
Figure 36:
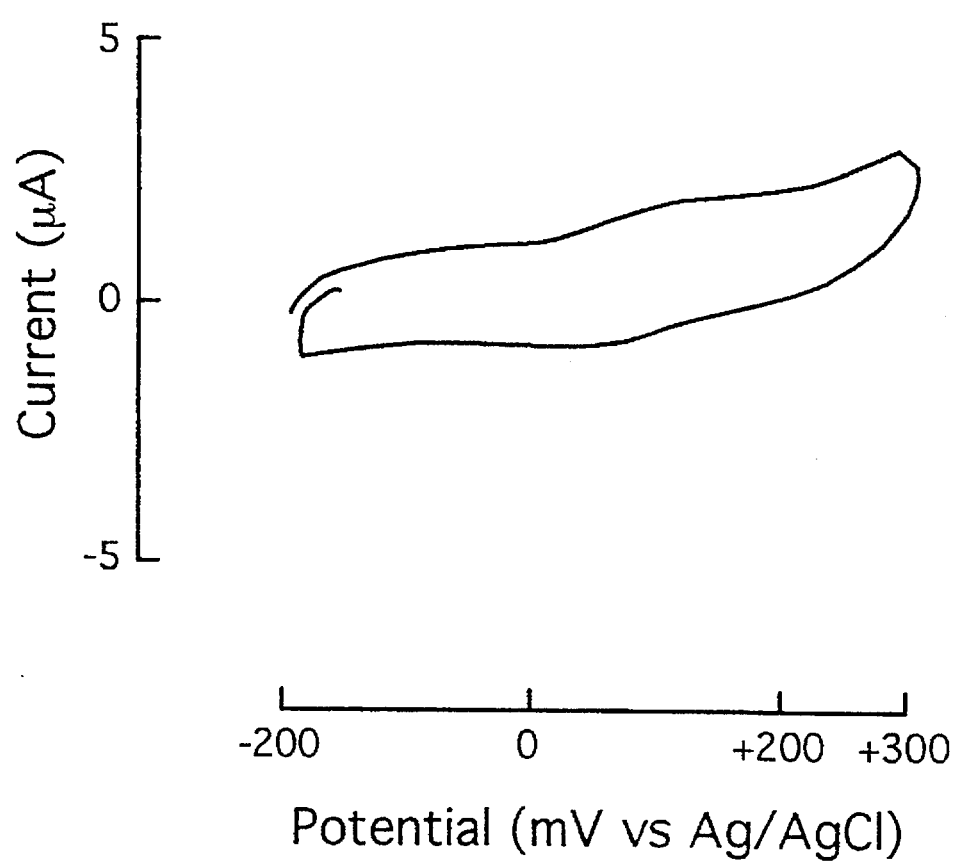
FIG. 36 is a graph showing cyclic volutammetry (potential scanning range, −200 mV to +300 mV) of p-phenylenediamine derivative having tri-substituted amino groups obtained from the reaction of p-phenylenediamine with propyleneoxide.

Results of −500 mV to +800 mV and −200 mV to +300 mV of TEPD are shown in FIGS. 6 and 7, respectively. In the same manner, results of TCPD are shown in FIGS. 8 and 9, and those of THEPD in FIGS. 10 and 11 and those of TDHPD in FIGS. 12 and 13. The results of HTEPD are shown in FIGS. 25 and 26, and those of N,N-BHDPD in FIGS. 27 and 28 and those of N,N'-BHDPD in FIGS. 29 and 30, and those of p-phenylenediamine derivatives having mono-substituted an amino group by reacting p-phenylenediamine with propyleneoxide (HPPD) in FIGS. 31 and 32 and those of p-phenylenediamine derivatives having di-substituted amino group or groups by reacting p-phenylenediamine with propyleneoxide in FIGS. 33 and 34 and p-phenylenediamine derivatives having tri-substituted amino groups by reacting p-phenylenediamine with propyleneoxide in FIGS. 35 and 36.

As is evident from the CV data shown in FIGS. 8 to 13 and FIGS. 25 to 36 similar to the case of the aforementioned TEPD (FIGS. 6 and 7), each of TCPD, THEPD, TDHPD, HTEPD, N,N-BHDPD, N,N'-BHDPD, and p-phenylenediamine derivatives having substituted amino group by reacting p-phenylenediamine with propyleneoxide is also a compound capable of undergoing oxidation-reduction reaction on an electrode and can be used suitably as an electron mediator in electrochemical measurements. In addition, as shown in FIGS. 9, 11, 13, 26, 28, 30, 32, 34 and 36 reversible oxidation-reduction reaction can be effected by these compound within a potential range of −200 mV to +300 mV.

Test Example 3

Measurement of electron transfer activities of TEPD, TCPD, THEPD, TDHPD, HTEPD, N,N'-BHPD, N,N-BHDPD, N,N'-BHDPD, and p-phenylenediamine derivatives having substituted amino group by reacting p-phenylenediamine with propyleneoxide—1

Glucose oxidase (GOD, manufactured by Boehringer-Mannheim) was dissolved in 0.1M phosphate buffer (pH 6.0) containing 0.1M NaCl to prepare 0M and $4.0 \times 10^{-4}$M GOD solutions. Also, glucose (manufactured by Junsei Kagaku) was dissolved in the same buffer to prepare a 1.5M solution. In the same manner, each of the TEPD, TCPD, THEPD, TDHPD, HTEPD, N,N-BHDPD, N,N'-BHPD, N,N'-BHDPD, and p-phenylenediamine derivatives having substituted amino group by reacting p-phenylenediamine with propyleneoxide obtained in Synthesis Examples 1 to 9 was dissolved in the same buffer to prepare a $5.0 \times 10^{-3}$M solution.

Each of these solutions was mixed in 0.1M phosphate buffer (pH 6.0) containing 0.1M NaCl in the following mixing ratio just before the measurement to prepare solutions of the following compositions A and B, and current was measured continuously in the presence (composition A) or absence (composition B) of GOD.

| Composition A | | |
|---|---|---|
| GOD | $4.0 \times 10^{-4}$M | 100 µl |
| glucose | 1.5M | 1.0 ml |
| compound solution | $5.0 \times 10^{-3}$M | 1.0 ml |

| buffer* | | 7.9 ml |
|---|---|---|
| Composition B | | |
| GOD | 0M | 100 µl |
| glucose | 1.5M | 1.0 ml |
| compound solution | $5.0 \times 10^{-3}$M | 1.0 ml |
| buffer* | | 7.9 ml |

*0.1M phosphate buffer (pH 6.0) containing 0.1M NaCl

Using the same apparatus of Test Example 2, electric current was measured in the presence (composition A) or absence (composition B) of GOD for 10 minutes under application of potential of +300 mV (vs Ag/AgCl) to the working electrode.

Figure 14:
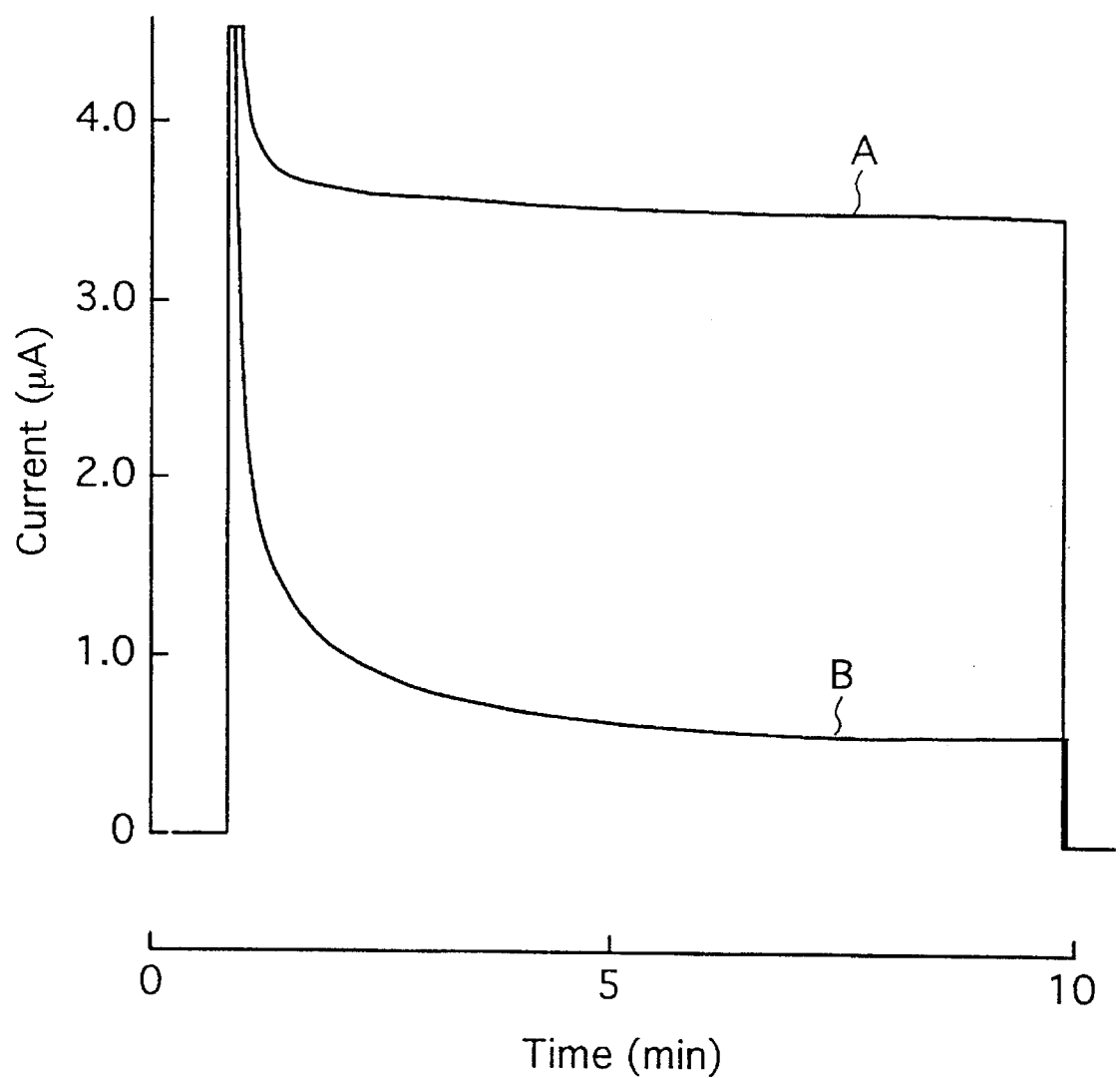
FIG. 14 is a graph showing the electron transfer activity of TEPD.
Figure 15:
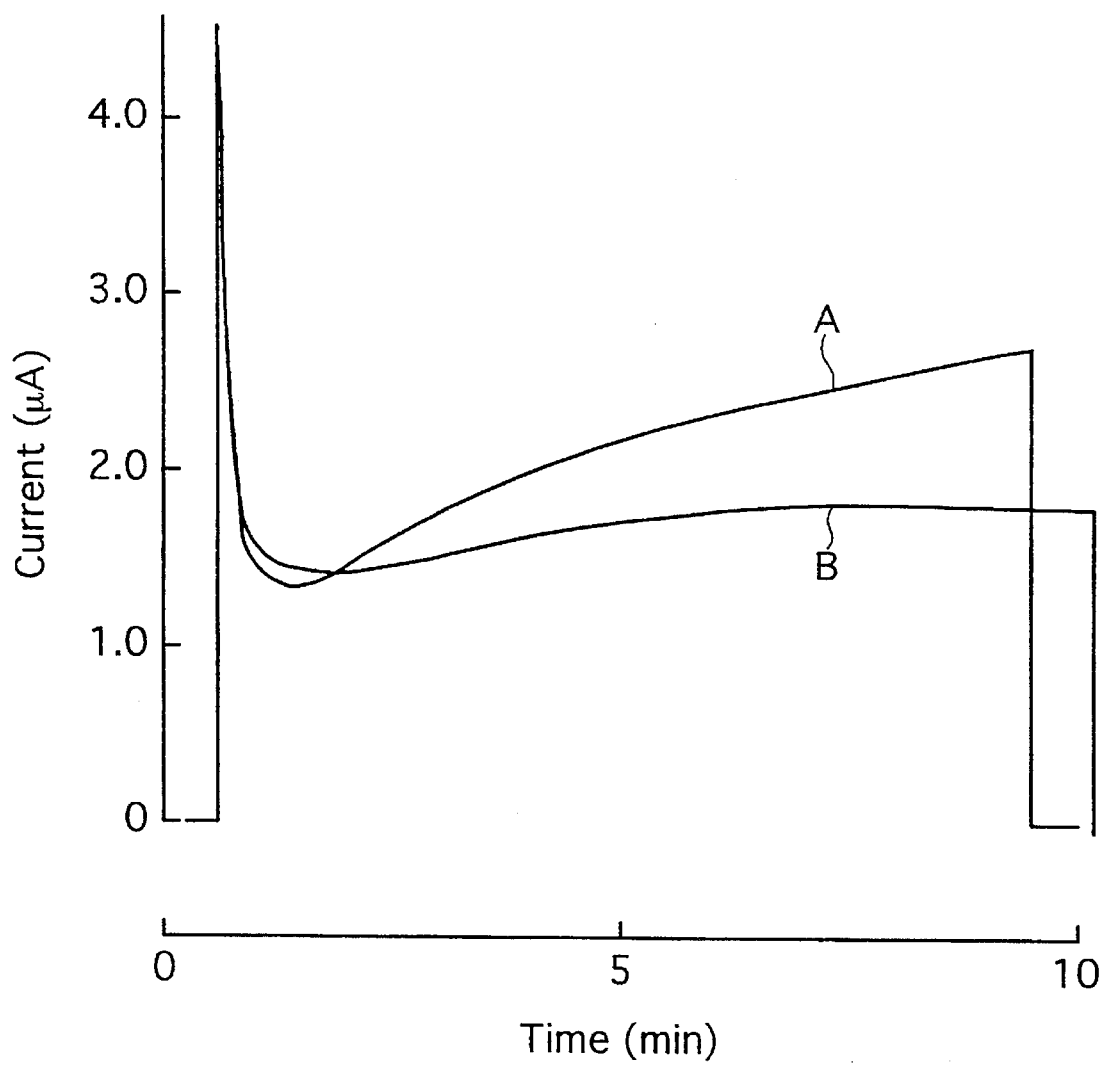
FIG. 15 is a graph showing the electron transfer activity of TCPD.
Figure 16:
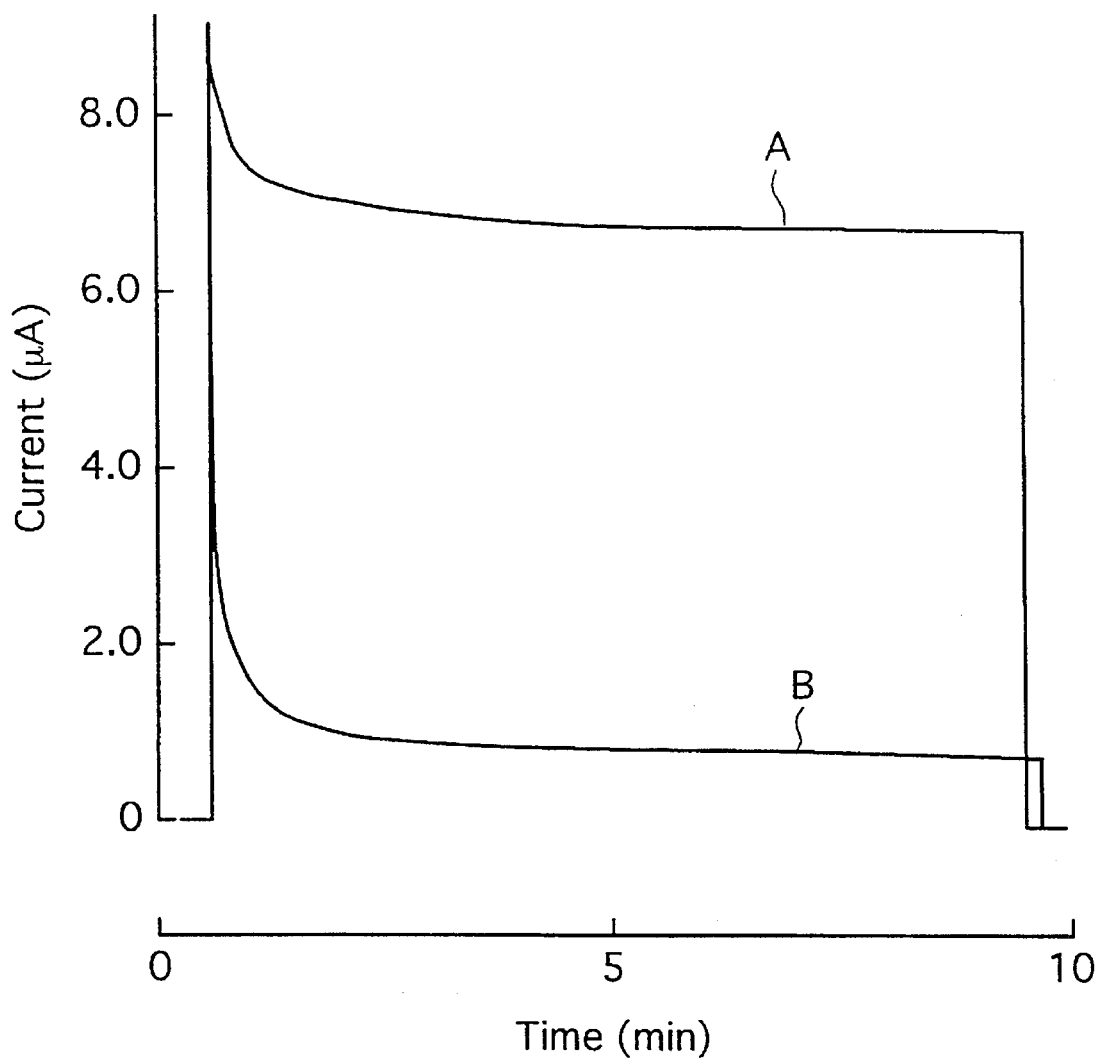
FIG. 16 is a graph showing the electron transfer activity of THEPD.
Figure 17:
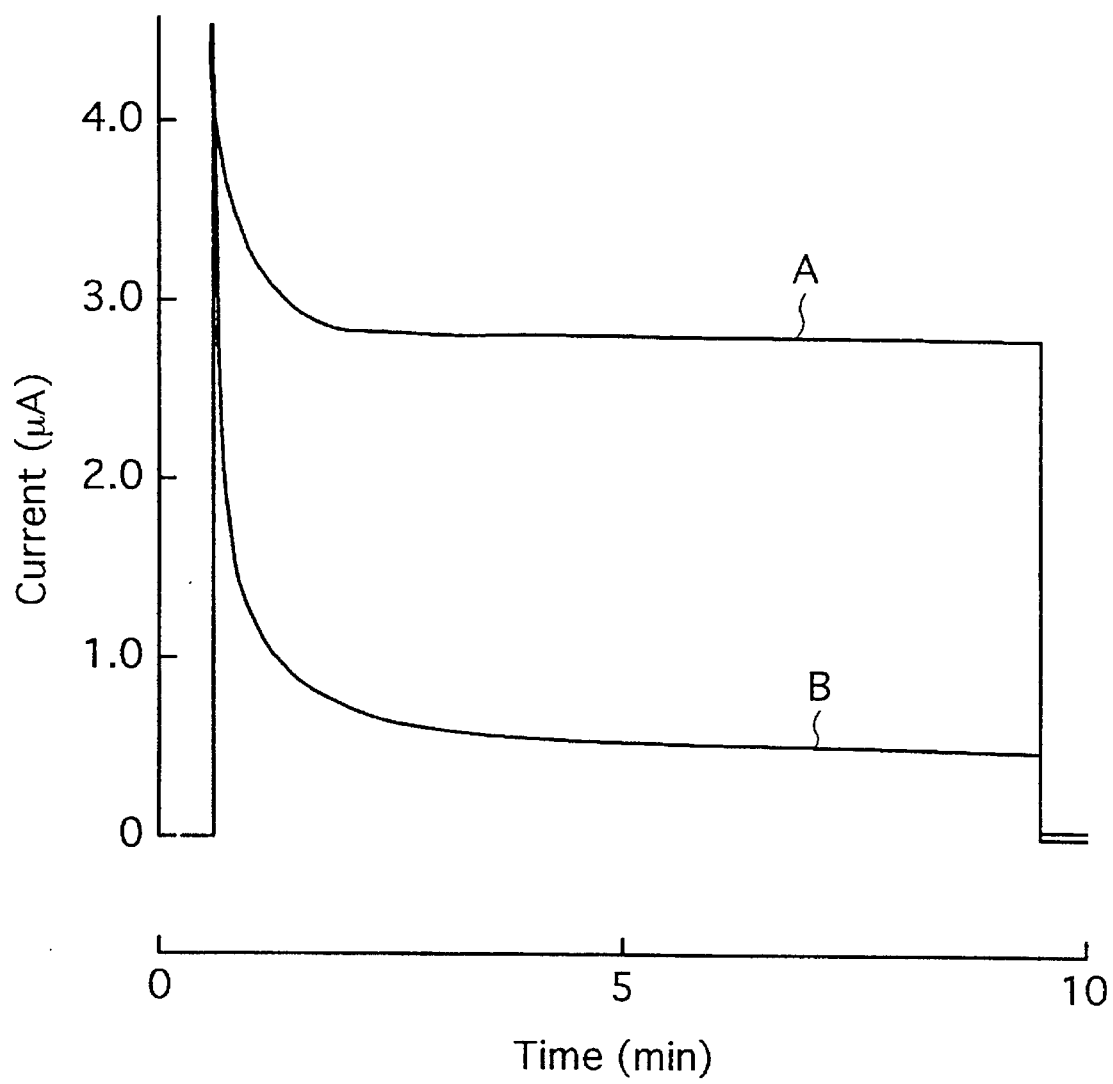
FIG. 17 is a graph showing the electron transfer activity of TDHPD.

Results of the measurement of TEPD (GOD-glucose-TEPD) are shown in FIG. 14, and those of TCPD (GOD-glucose-TCPD) in FIG. 15, THEPD (GOD-glucose-THEPD) in FIG. 16 and TDHPD (GOD-glucose-TDHPD) in FIG. 17.

Figure 37:
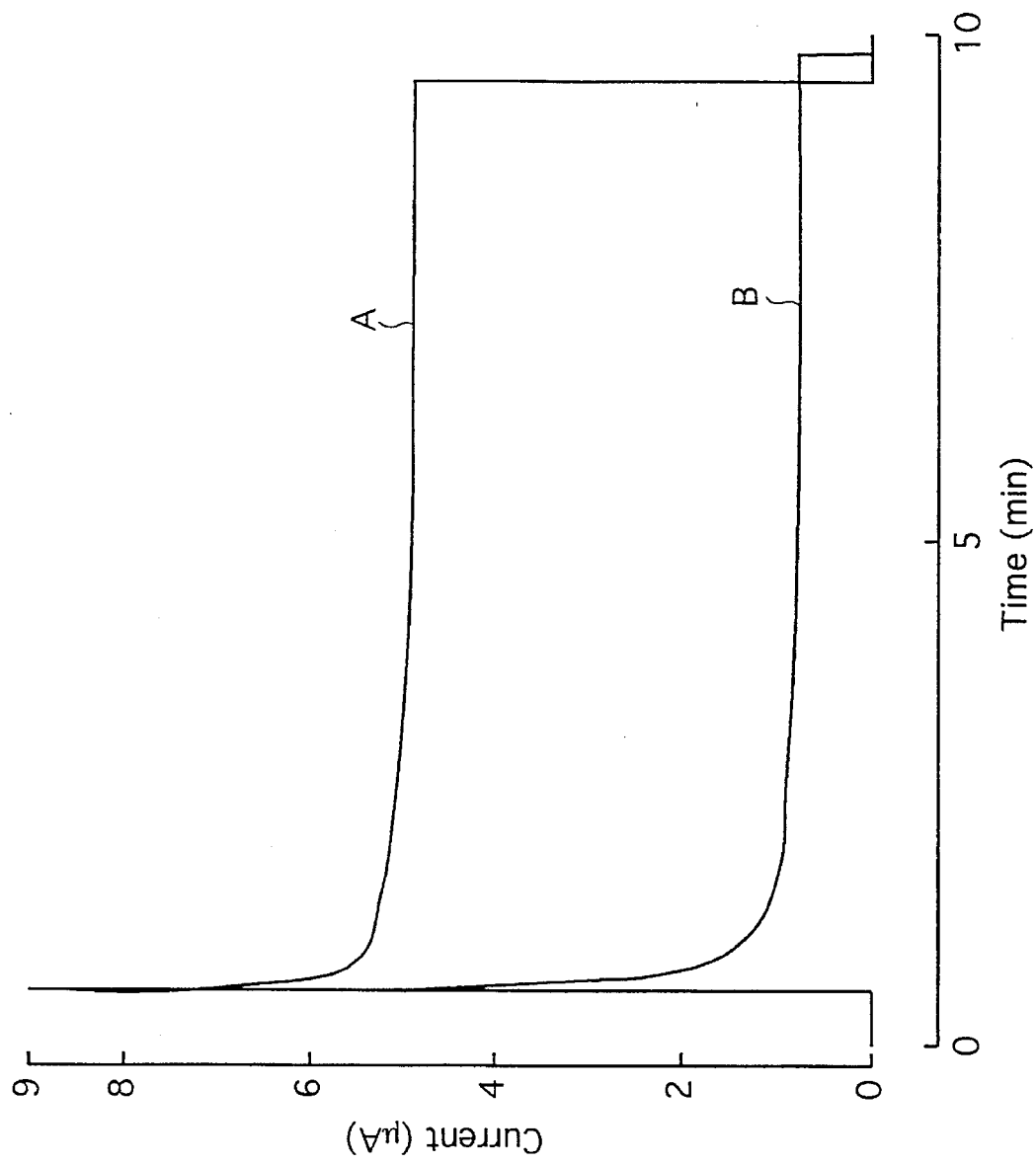
FIG. 37 is a graph showing the electron transfer activity of HTEPD.
Figure 38:
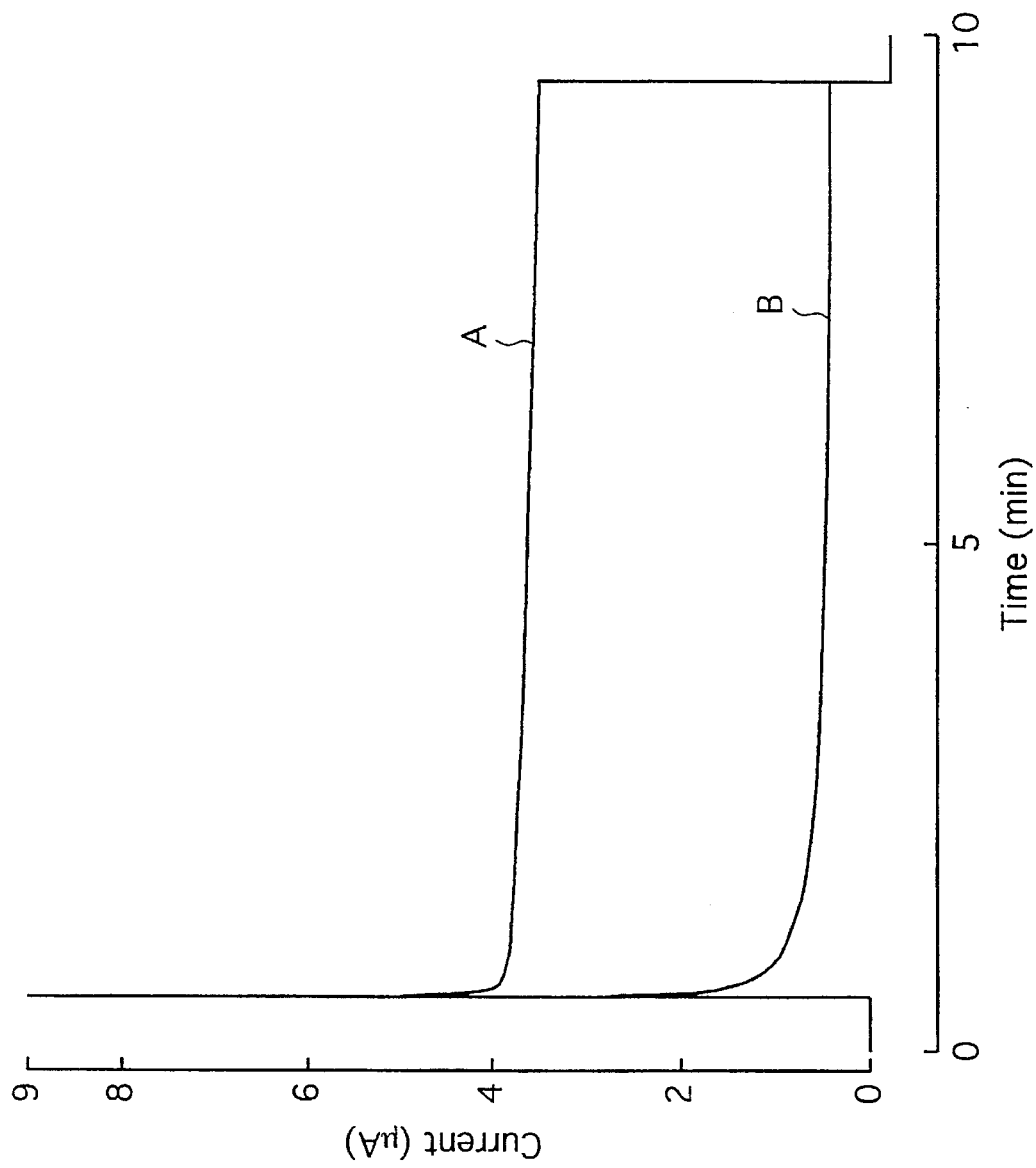
FIG. 38 is a graph showing the electron transfer activity of N,N-BHDPD.
Figure 39:
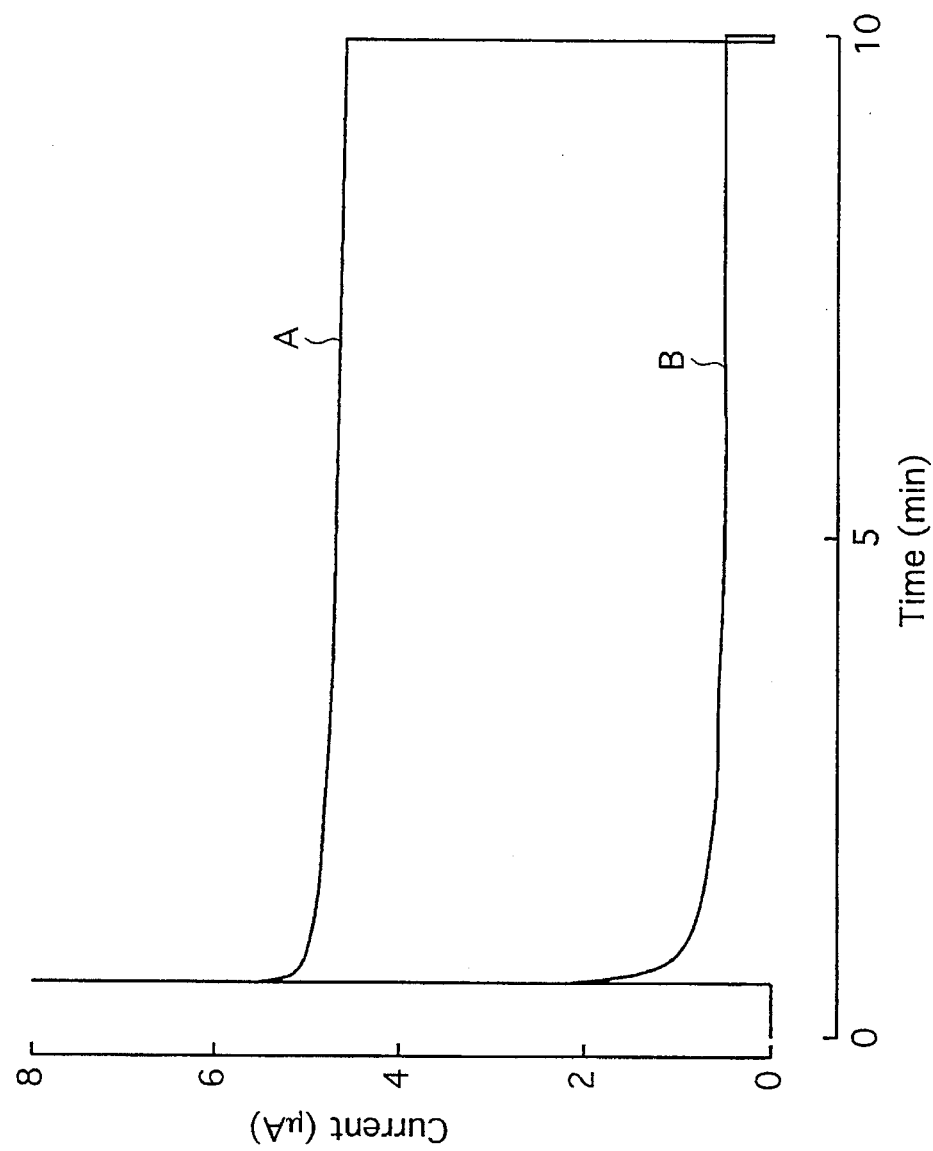
FIG. 39 is a graph showing the electron transfer activity of N-N'-BHDPD.

Results of the measurement of HTEPD (GOD-glucose-HTEPD) are shown in FIG. 37, and those of N,N-BHDPD (GOD-glucose-N,N-BHDPD) in FIG. 38, N,N'-BHDPD (GOD-glucose-N,N'-BHDPD) in FIG. 39.

Figure 40:
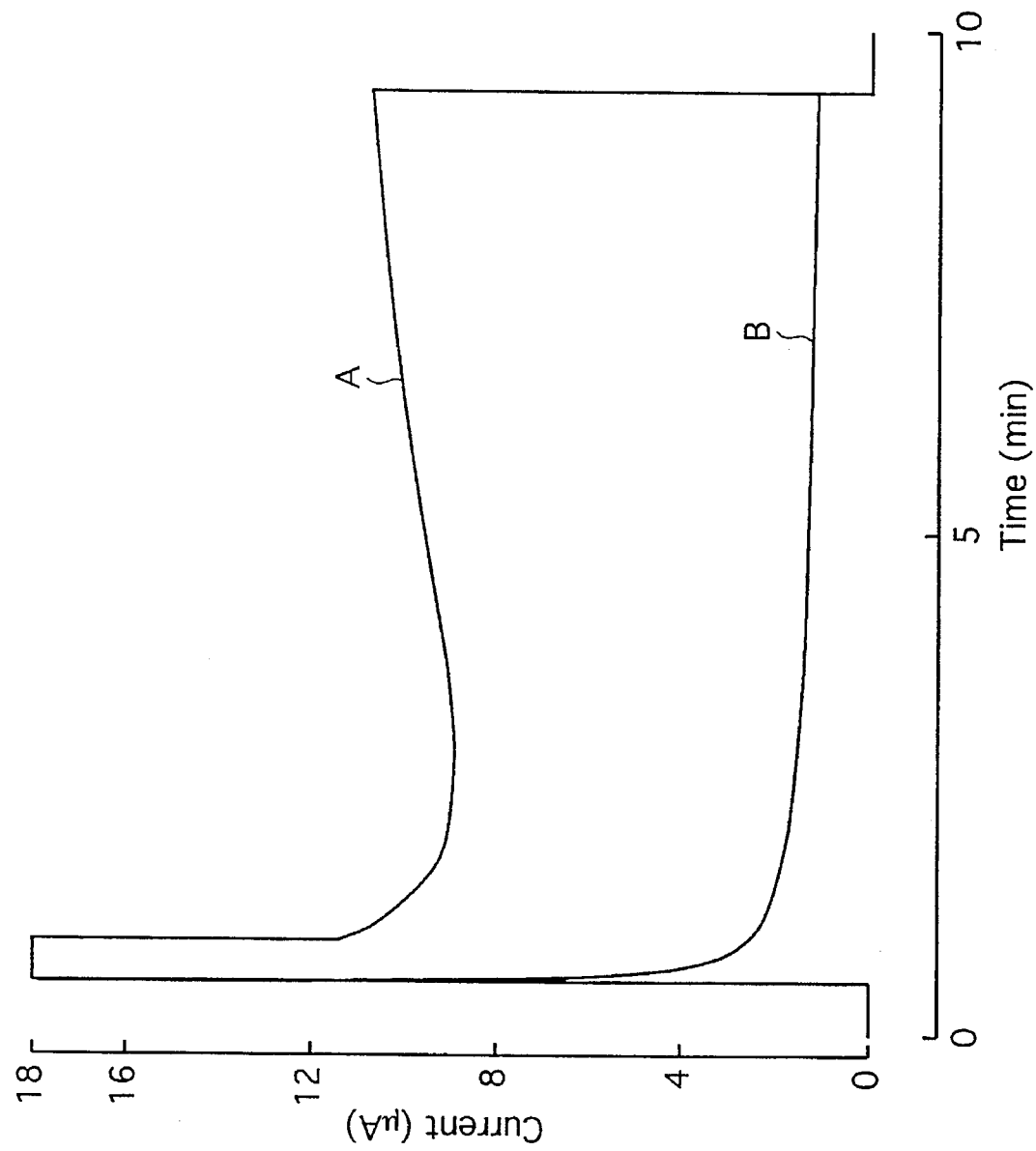
FIG. 40 is a graph showing the electron transfer activity of p-phenylenediamine derivative having mono-substituted an amino group obtained from the reaction of p-phenylenediamine with propyleneoxide (HPPD).
Figure 41:
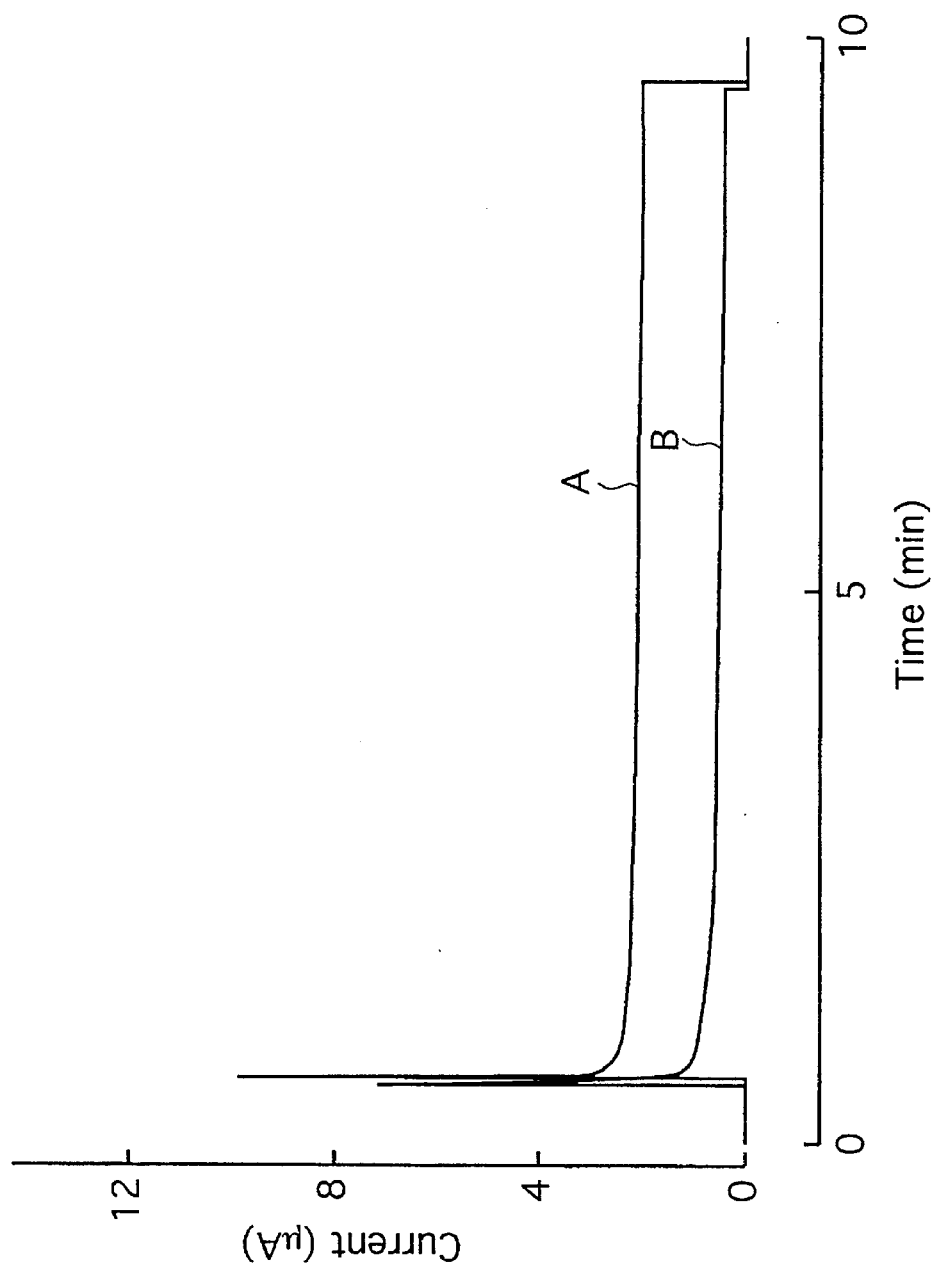
FIG. 41 is a graph showing the electron transfer activity of p-phenylenediamine derivative having di-substituted an amino group or two amino groups obtained from the reaction of p-phenylenediamine with propyleneoxide.
Figure 42:
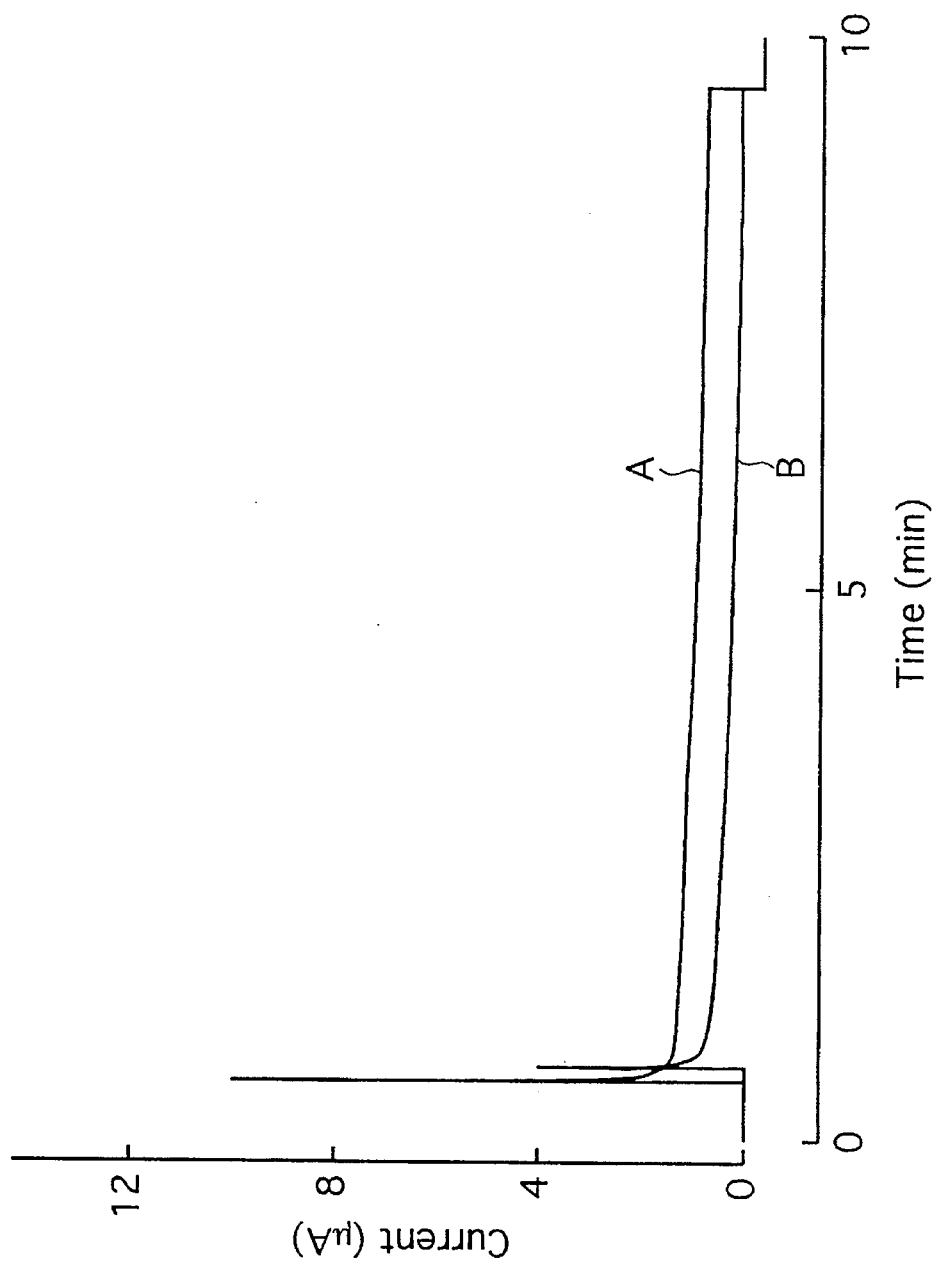
FIG. 42 is a graph showing the electron transfer activity of p-phenylenediamine derivative having tri-substituted amino groups obtained from the reaction of p-phenylenediamine with propyleneoxide.

Results of the measurement of p-phenylenediamine derivatives having mono-substituted an amino group by reacting p-phenylenediamine with propyleneoxide (HPPD) are shown in FIG. 40 and those of p-phenylenediamine derivatives having di-substituted amino group or groups by reacting p-phenylenediamine with propyleneoxide in FIG. 41 and p-phenylenediamine derivatives having tri-substituted amino groups by reacting p-phenylenediamine with propyleneoxide in FIG. 42.

As shown in FIGS. 14 to 17 and FIGS. 37 to 42, the oxidation current increases by the measurement of any one of the compounds when GOD is present in the system (composition A) in comparison with the case of its absence (composition B). In consequence, it is apparent that, similar to the case of the prior art TEPD, each of the TCPD, THEPD, TDHPD, HTEPD, N,N-BHDPD, N,N'-BHDPD, and p-phenylenediamine derivatives having substituted amino group by reacting p-phenylenediamine with propyleneoxide of the present invention is possessed of a function as a reversible electron mediator between GOD and the electrode. And similar to the case of those compounds, N,N'-BHPD of the present invention is possessed of a function as a reversible electron mediator between GOD and the electrode.

Test Example 4

Measurement of electron transfer activities of TCPD, THEPD, TDHPD, HTEPD, N,N-BHDPD, N,N'-BHPD, N,N'-BHDPD, and p-phenylenediamine derivatives having substituted amino group by reacting p-phenylenediamine with propyleneoxide—2

Horseradish peroxidase (HRPO, manufactured by TOYOBO) was dissolved in 0.1M phosphate buffer (pH 6.0) containing 0.1M NaCl to prepare 0M and $5.0 \times 10^{-7}$M HRPO solutions. Also, hydrogen peroxide (manufactured by Wako Pure Chemical Industries) was dissolved in the same buffer to prepare a $1.0 \times 10^{-1}$M solution. In the same manner, each of the TCPD, THEPD, TDHPD, HTEPD, N,N-BHDPD, N,N'-BHPD, N,N'-BHDPD, and p-phenylenediamine derivatives having substituted amino group by reacting p-phenylenediamine with propyleneoxide obtained in Synthesis Examples 1 to 9 was dissolved in the same buffer to prepare a $5.0 \times 10^{-3}$M solution.

Each of these solutions was mixed in 0.1M phosphate buffer (pH 6.0) containing 0.1M NaCl in the following mixing ratio just before the measurement to prepare solutions of the following compositions A and B, and electric current was measured continuously in the presence (composition A) or absence (composition B) of HRPO.

| Composition A | | |
|---|---|---|
| HRPO | $5.0 \times 10^{-7}$M | 100 µl |
| hydrogen peroxide | $1.0 \times 10^{-1}$M | 100 µl |
| compound solution | $5.0 \times 10^{-3}$M | 1.0 ml |
| buffer* | | 8.8 ml |
| Composition B | | |
| HRPO | 0M | 100 µl |
| hydrogen peroxide | $1.0 \times 10^{-1}$M | 100 µl |
| compound solution | $5.0 \times 10^{-3}$M | 1.0 ml |
| buffer* | | 8.8 ml |

*0.1M phosphate buffer (pH 6.0) containing 0.1M NaCl

Using the same apparatus of Test Example 2, electric current was measured in the presence (composition A) or absence (composition B) of HRPO for 5 or 10 minutes after application of potential of −80 mV (vs Ag/AgCl, the same shall apply hereinafter) in the case of TEPD, THEPD, and TDHPD, or −150 mV in the case of TCPD, HTEPD, N,N-BHDPD, N,N'-BHPD, N,N'-BHDPD, and p-phenylenediamine derivatives having substituted amino group by reacting p-phenylenediamine with propyleneoxide.

Figure 18:
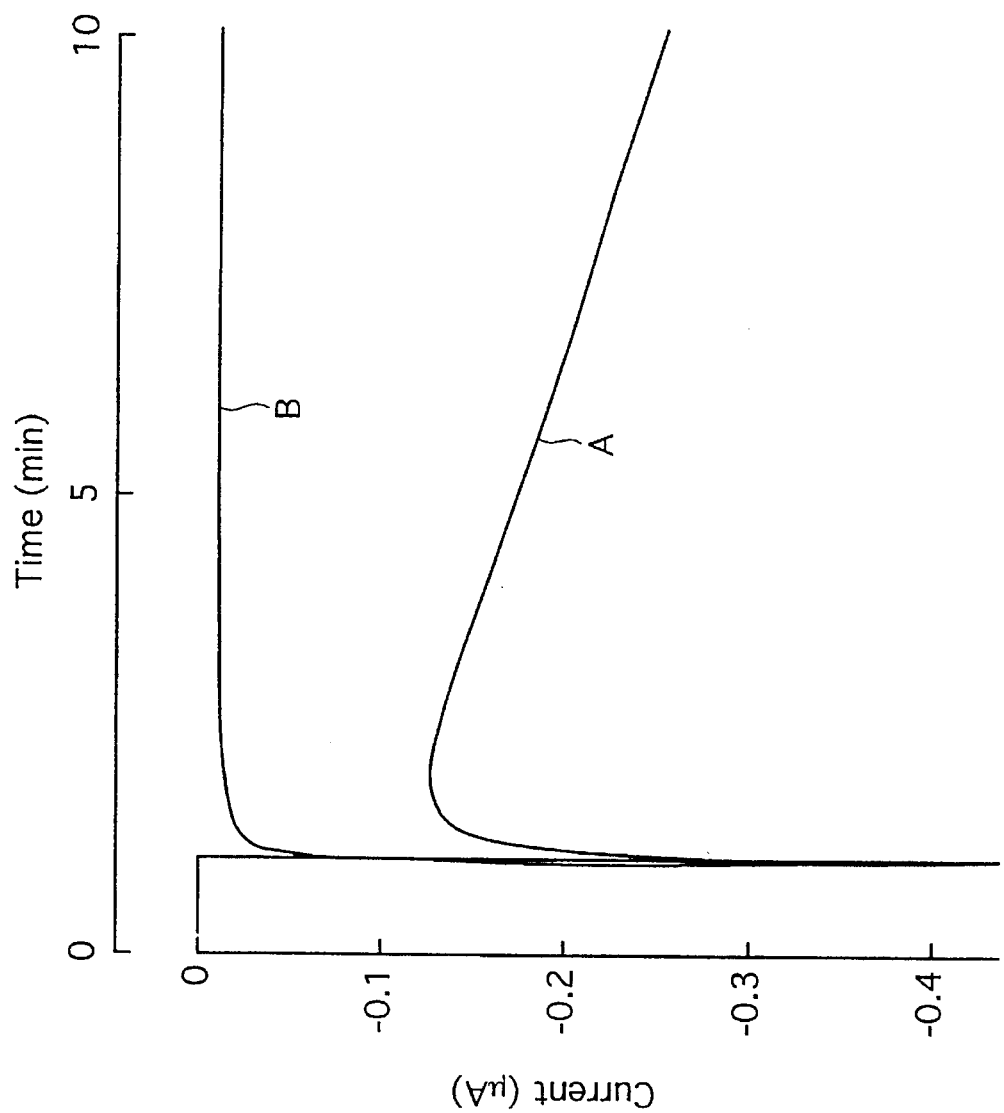
FIG. 18 is a graph showing another example of the electron transfer activity of TEPD.
Figure 19:
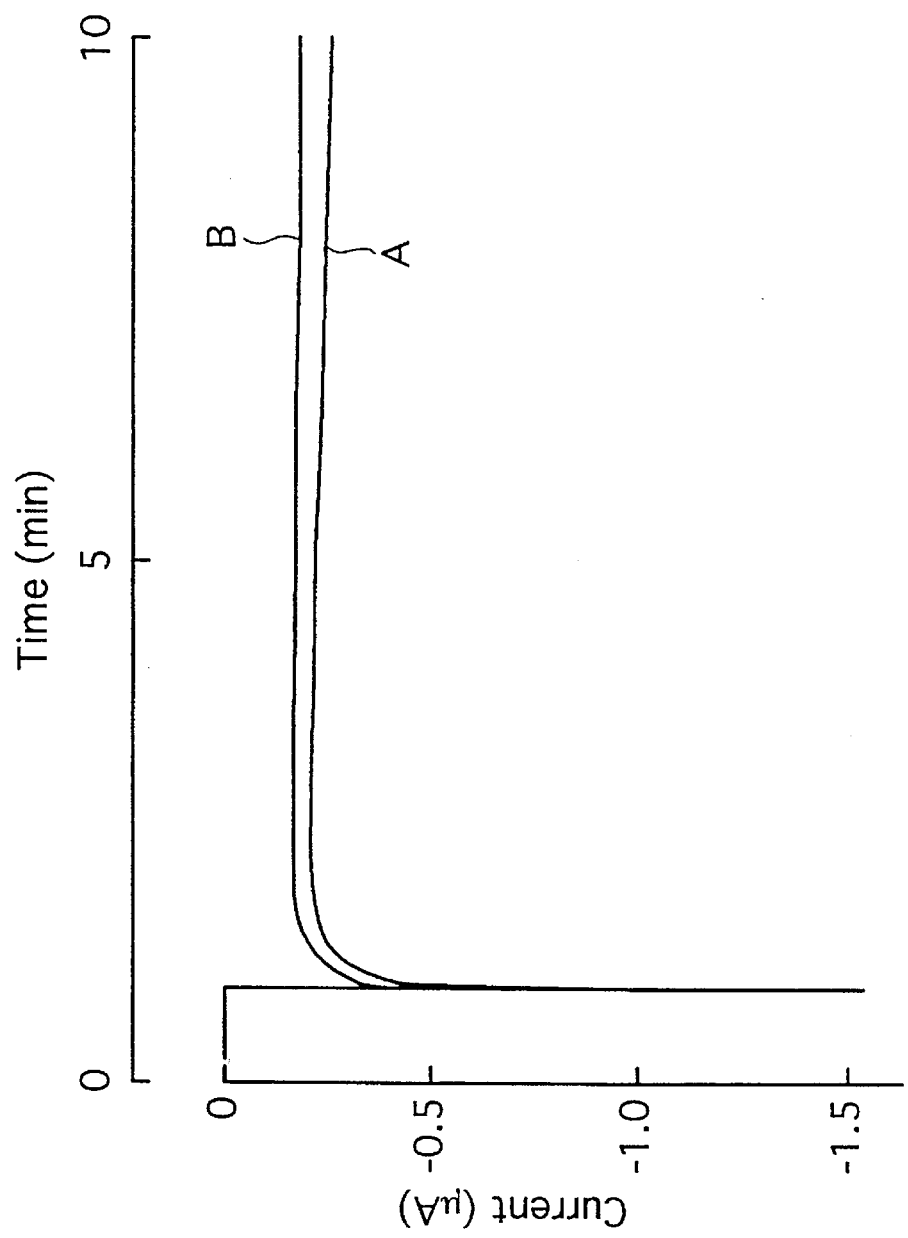
FIG. 19 is a graph showing another example of the electron transfer activity of TCPD.
Figure 20:
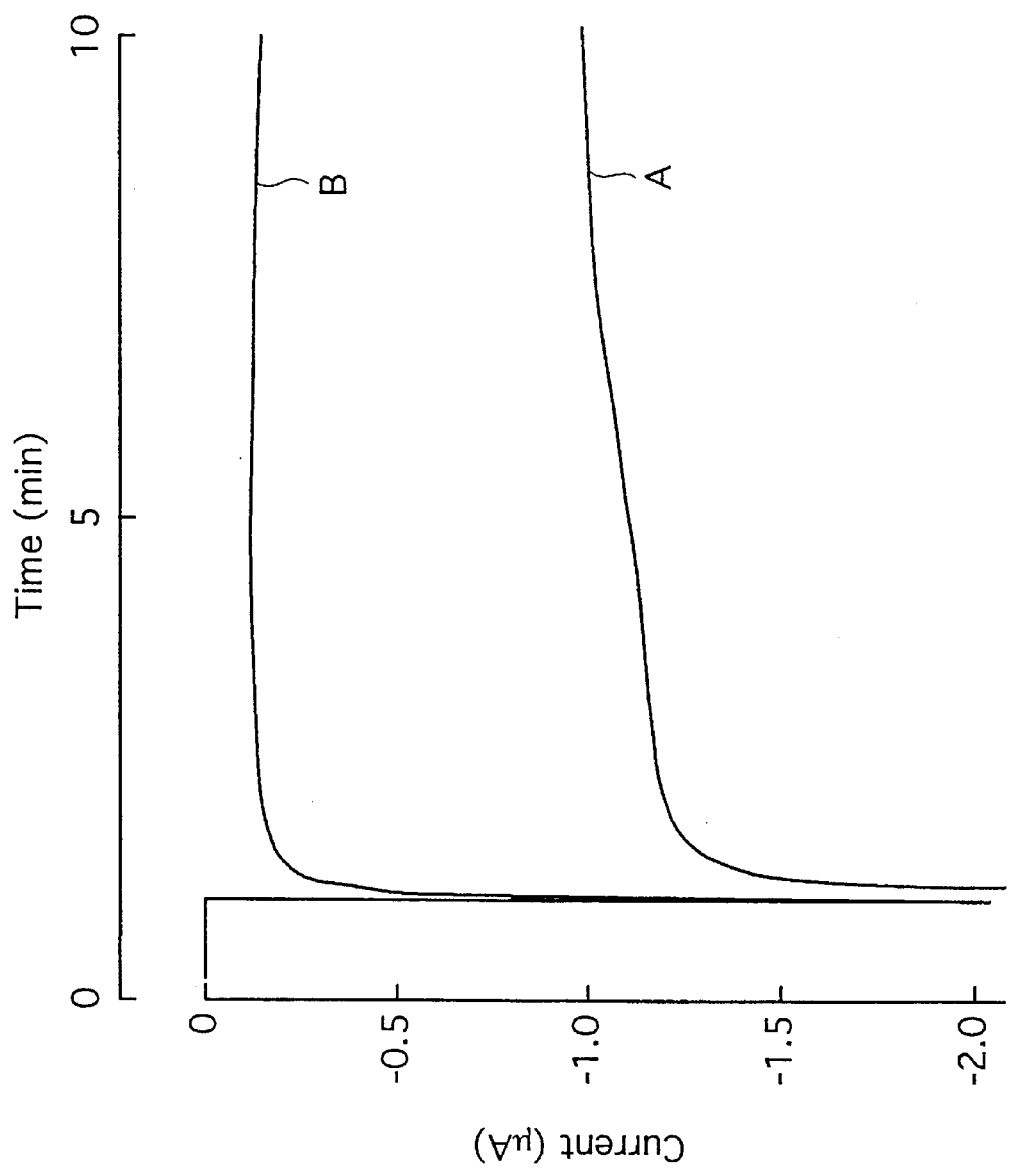
FIG. 20 is a graph showing another example of the electron transfer activity of THEPD.
Figure 21:
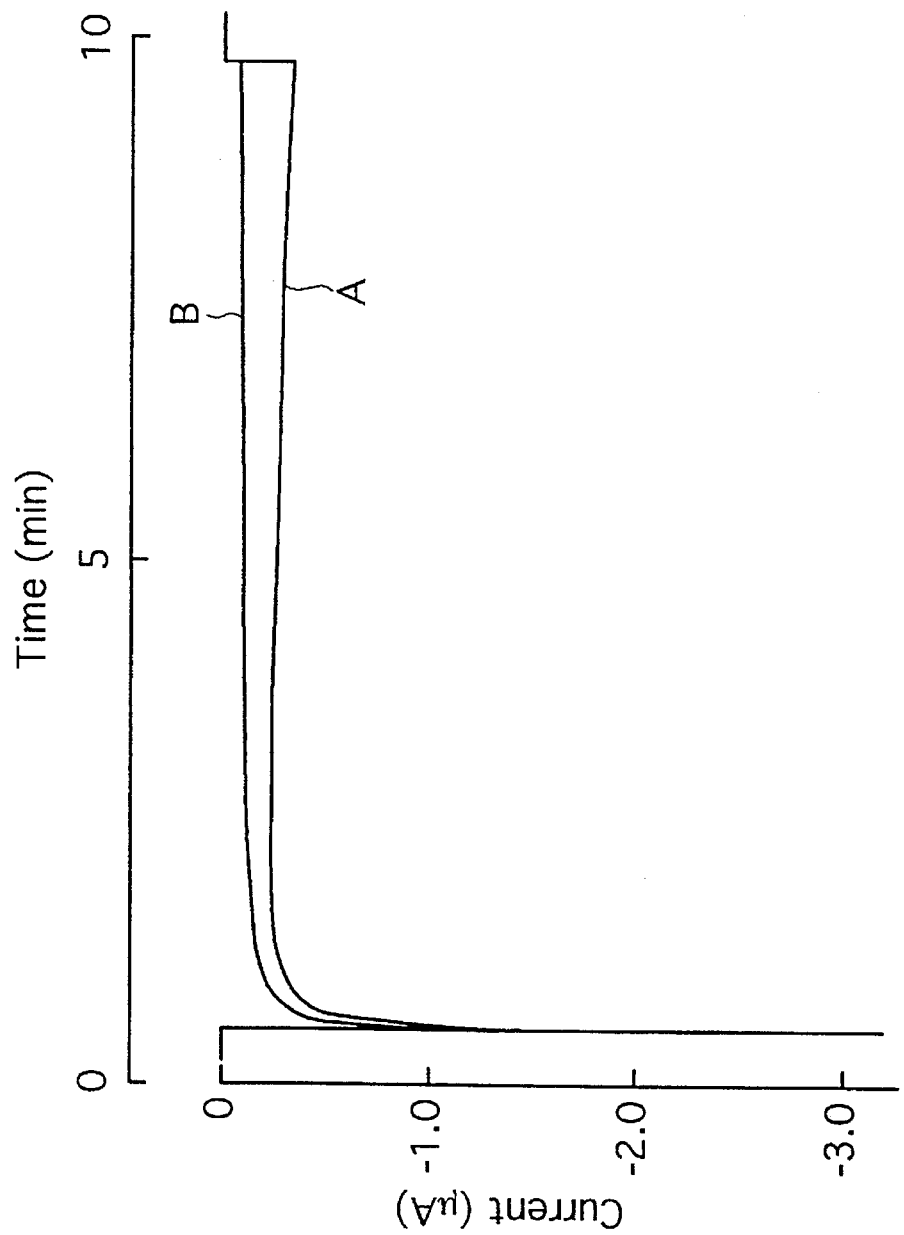
FIG. 21 is a graph showing another example of the electron transfer activity of TDHPD.

Results of the measurement of TEPD (HRPO-hydrogen peroxide-TEPD) are shown in FIG. 18, and those of TCPD (HRPO-hydrogen peroxide-TCPD) in FIG. 19, THEPD (HRPO-hydrogen peroxide-THEPD) in FIG. 20 and TDHPD (HRPO-hydrogen peroxide-TDHPD) in FIG. 21.

Figure 43:
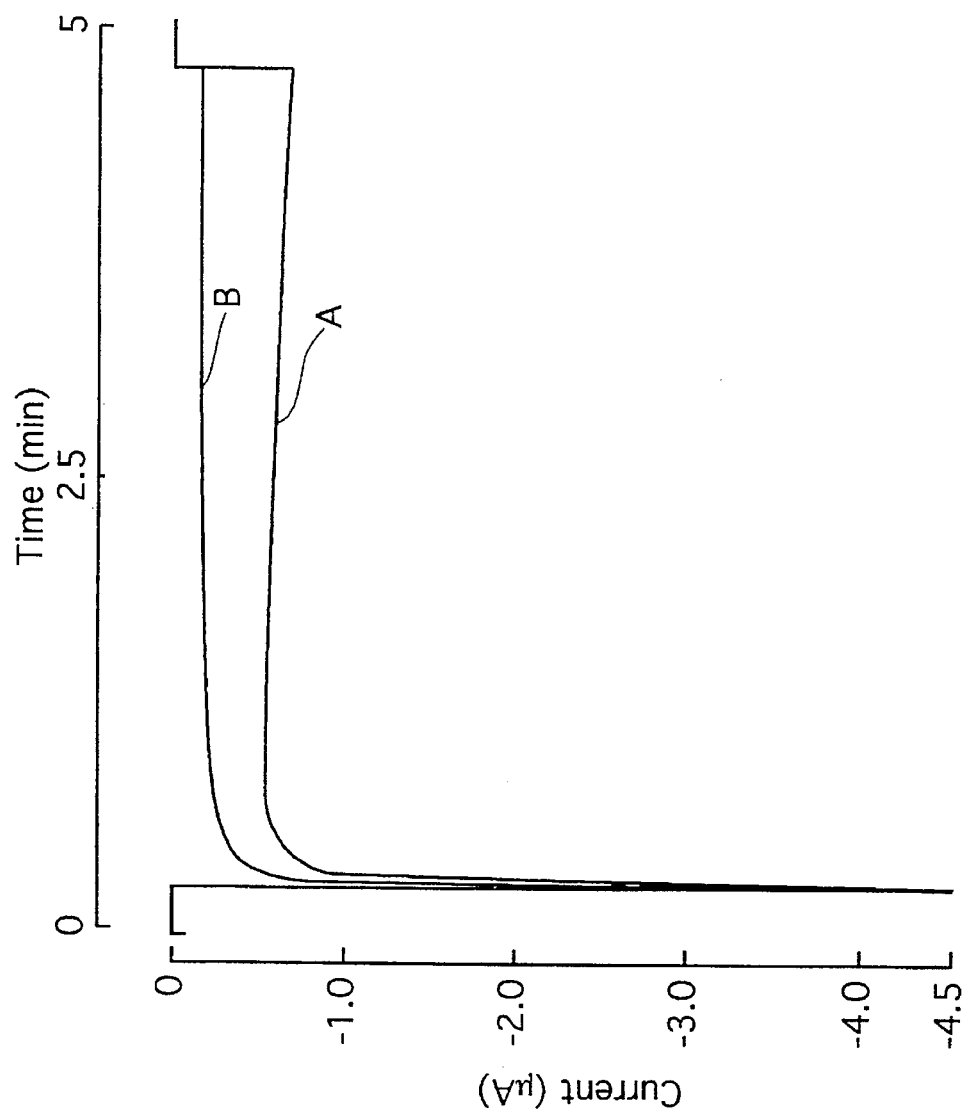
FIG. 43 is a graph showing another example of the electron transfer activity of HTEPD.
Figure 44:
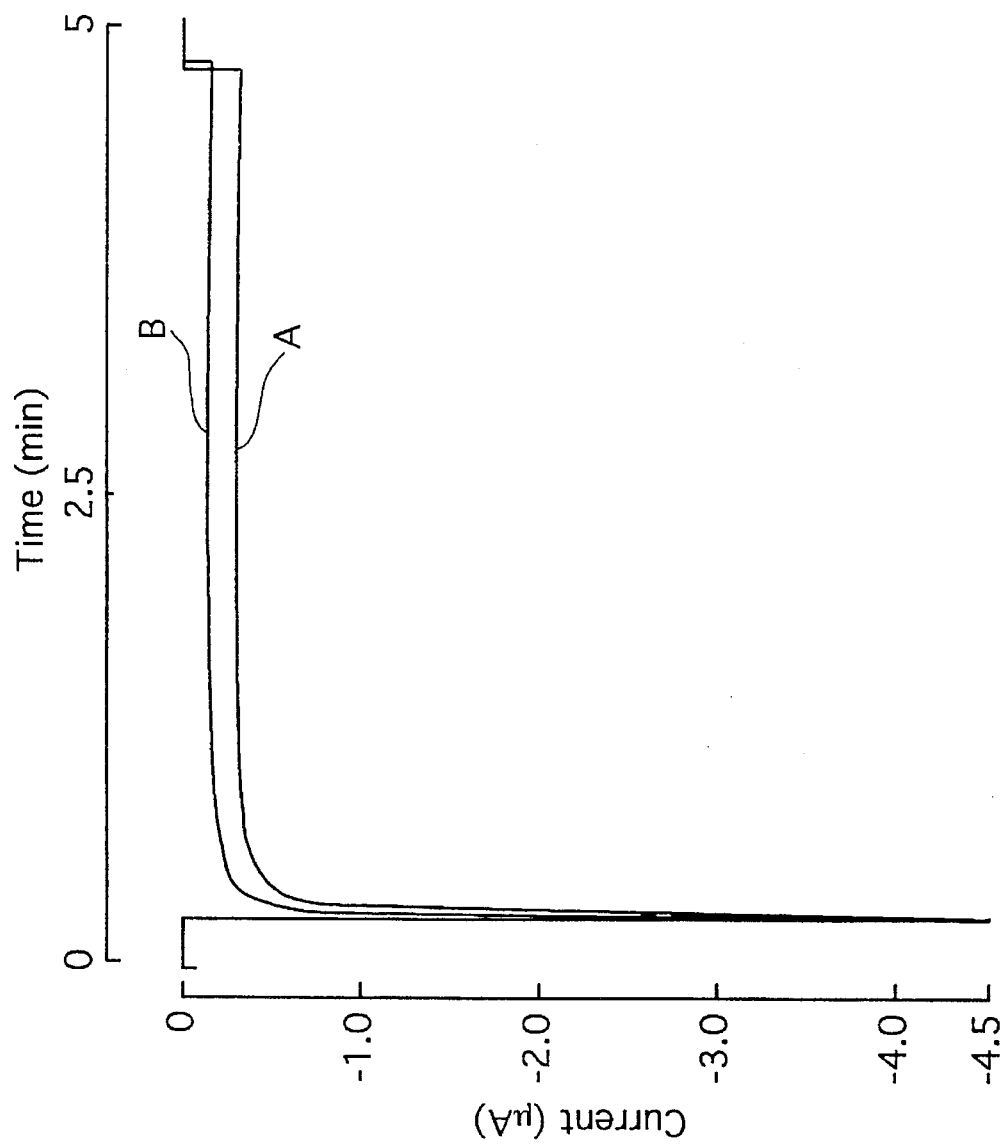
FIG. 44 is a graph showing another example of the electron transfer activity of N,N-BHDPD.
Figure 45:
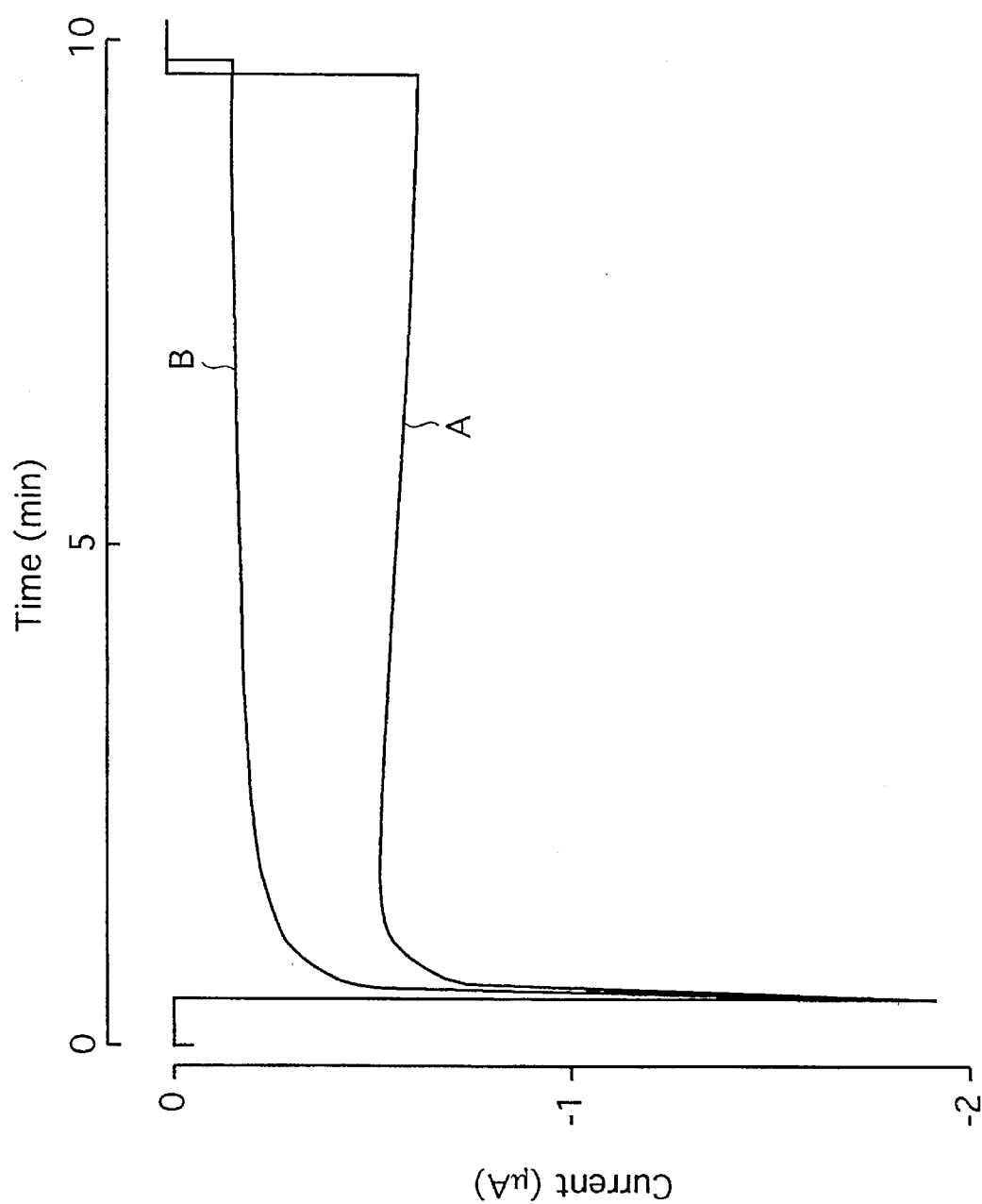
FIG. 45 is a graph showing another example of the electron transfer activity of N,N'-BHDPD.

Results of the measurement of HTEPD (GOD-glucose-HTEPD) are shown in FIG. 43, and those of N,N-BHDPD (GOD-glucose-N,N-BHDPD) in FIG. 44, N,N'-BHDPD (GOD-glucose-N,N'-BHDPD) in FIG. 45.

Figure 46:
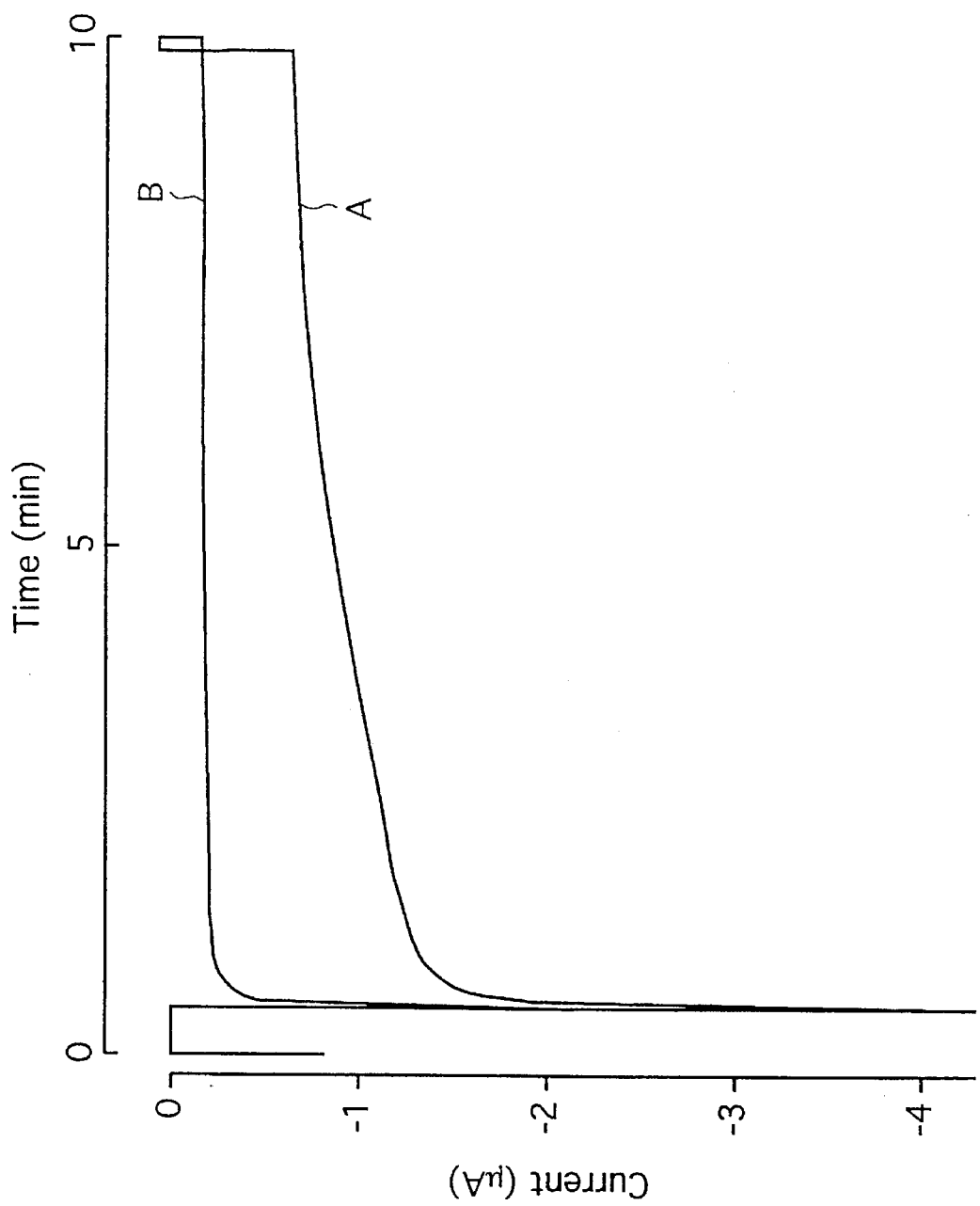
FIG. 46 is a graph showing another example of the electron transfer activity of p-phenylenediamine derivative having mono-substituted an amino group obtained from the reaction of p-phenylenediamine with propyleneoxide (HPPD).
Figure 47:
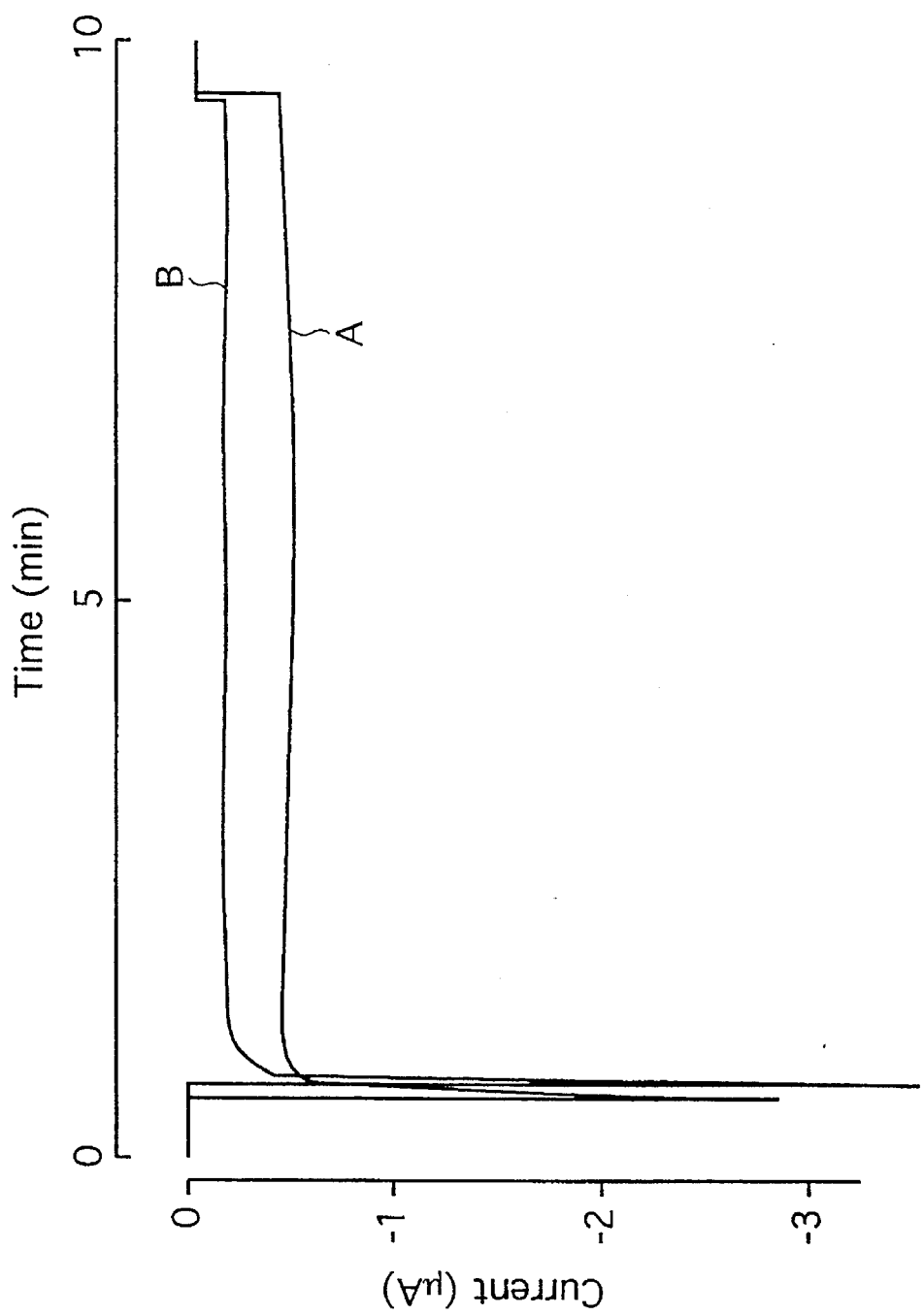
FIG. 47 is a graph showing another example of the electron transfer activity of p-phenylenediamine derivative having di-substituted an amino group or two amino groups obtained from the reaction of p-phenylenediamine with propyleneoxide.

Results of the measurement of p-phenylenediamine derivatives having mono-substituted an amino group by reacting p-phenylenediamine with propyleneoxide (HPPD) are shown in FIG. 46 and those of p-phenylenediamine derivatives having di-substituted amino group or groups by reacting p-phenylenediamine with propyleneoxide in FIG. 47 and p-phenylenediamine derivatives having tri-substituted amino groups by reacting p-phenylenediamine with propyleneoxide in FIG. 48.

As shown in FIGS. 18 to 21 and FIGS. 43 to 48, the reduction current increases by the measurement of any one of the compounds when HRPO is present in the system (composition A) in comparison with the case of its absence (composition B). In consequence, it is apparent that, similar to the case of the prior art TEPD, each of the TCPD, THEPD, TDHPD, HTEPD, N,N-BHDPD, N,N'-BHDPD, and p-phenylenediamine derivatives having substituted amino group by reacting p-phenylenediamine with propyleneoxide of the present invention is possessed of a function as a reversible electron mediator between HRPO and the electrode. And similar to the case of those compounds, N,N'-BHPD of the present invention is possessed of a function as a reversible electron mediator between HRPO and the electrode.

Inventive Example

The specific binding assay device shown in FIGS. 2 and 3 was constructed, and concentration of hCG in samples was measured using the device.

Firstly, the following members were prepared for use in the construction of the specific binding assay device.

(1) Preparation of a conjugate of anti-hCG antibody and horseradish peroxidase (labeled antibody)

A mouse monoclonal anti-hCG antibody HM81 (prepared by Mochida Pharmaceutical) was dissolved in a 100 mM sodium chloride/1 mM EDTA/60 mM triethanolamine buffer solution (pH 8.0, TEA buffer) to a final concentration of 8.3 mg/ml, and the resulting solution was thoroughly dialyzed against TEA buffer which has been purged with nitrogen gas. A 61 μl portion of 50 mM 2-iminothiolane hydrochloride (manufactured by Pierce Chemical Company) solution was added to 1.1 ml of the thus prepared antibody solution, and the mixture was stirred and then allowed to stand still for 1.5 hours at 4° C. in an atmosphere of nitrogen gas. Thereafter, the resulting solution was thoroughly dialyzed against a 100 mM phosphate buffer solution (pH 7.0) containing 100 mM sodium chloride and 1 mM EDTA (EDTA-PB) which has been purged with nitrogen. In this way, SH group-introduced anti-hCG antibody HM81 was obtained.

On the other hand, horseradish peroxidase (HRPO, manufactured by TOYOBO) was dissolved in 100 mM phosphate buffer (pH 7.0) to a final concentration of 20 mg/ml. With stirring at 30° C., 500 μl of the thus prepared enzyme solution was mixed with 500 μl of 50 mM sulfo-SMCC (manufactured by Pierce Chemical Company). After 20 minutes of reaction at 30° C., the resulting reaction mixture was passed through a column (2.6ø×15 cm) packed with Sephadex G-25 (manufactured by Pharmacia) which has been equilibrated in advance with nitrogen-purged EDTA-PB, thereby removing unreacted sulfo-SMCC, and then the resulting solution was concentrated using a concentrator (CENTRIPREP-10, manufactured by Amicon Corp.) to obtain maleimidated HRPO. Concentration of the maleimidated HRPO was determined based on the absorbance at 403 nm.

A solution of the maleimidated HRPO ($1.25 \times 10^{-8}$ mole or $1.56 \times 10^{-8}$ mole) was mixed with a solution of the SH group-introduced anti-hCG antibody HM81 (3 times or ⅓ times in molar ratio), and the mixture was incubated at 4° C. for 12 hours in an atmosphere of nitrogen gas. After the reaction, 50 μl of 50 mM cysteamine solution was added to each of the reaction mixture, and the reaction was continued at 4° C. for 60 minutes in an atmosphere of nitrogen gas. Thereafter, the resulting reaction mixture was subjected to gel filtration chromatography using an ULTROGEL AcA34 (manufactured by IBF Biotechniques) column which have been equilibrated in advance with nitrogen-purged EDTA-PB.

Each of the eluted fractions were checked for its absorbances at 280 nm and 403 nm, in order to collect and concentrate fractions containing the HM81/HRPO conjugated product but not containing free enzyme molecules. After confirming molecular weight of the thus concentrated conjugate (to be referred to as "HRPO-HM81" hereinafter) by a Phast system electrophoresis (Pharmacia), amounts of the antibody and enzyme contained in the conjugate were determined based on the absorbance and enzyme activity. The thus prepared HRPO-HM81 was used as an oxidation-reduction enzyme-labeled antibody in measurement experiments.

(2) Preparation of a freeze-dry member impregnated with horseradish peroxidase-labeled anti-hCG antibody (HRPO-HM81)

The HRPO-HM81 obtained in the above step (1) was diluted with a phosphate buffer (pH 6.0) containing 5% normal rabbit serum (NRS), 10% saccharose and 0.1M NaCl to prepare a solution having a peroxidase activity of 0.63 U/ml. Next, 140 μl of the solution was spotted on a circular filter paper piece of 12 mm in diameter punched out from glass fiber filter paper (GA100, manufactured by Advantech Toyo) and then freeze-dried to obtain an HRPO-HM81 freeze-dry member to be used as the labeled antibody-impregnated member 14.

(3) Preparation of a freeze-dry member impregnated with THEPD (an inventive example)

The THEPD obtained in Synthesis Example 3 was dissolved in a phosphate buffer (pH 6.0) containing 0.1M NaCl to prepare a 5.0 mM solution. Next, 140 μl of the solution was spotted on a circular filter paper piece of 12 mm in diameter punched out from glass fiber filter paper (GA100, manufactured by Advantech Toyo) and then freeze-dried to obtain a THEPD freeze-dry member to be used as the electron mediator-impregnated member 16 of the present invention.

(4) Preparation of a freeze-dry member impregnated with TEPD (a comparative example)

The TEPD obtained in Synthesis Example 1 was dissolved in a phosphate buffer (pH 6.0) containing 1M NaCl to prepare a 5.0 mM solution. Next, 140 μl of the solution was spotted on a circular filter paper piece of 12 mm in diameter punched out from glass fiber filter paper (GA100, manufactured by Advantech Toyo) and then freeze-dried to obtain a TEPD freeze-dry member to be used as a comparative electron mediator-impregnated member 16.

(5) Preparation of a freeze-dry member impregnated with hydrogen peroxide

Hydrogen peroxide (Wako Pure Chemical Industries) and urea (Wako Pure Chemical Industries) were dissolved in distilled water to prepare a solution containing 0.5M hydrogen peroxide and 0.5M urea. Next, 120 μl of the solution was spotted on a circular filter paper piece of 12 nun in diameter punched out from chromatography filter paper (17 Chr, manufactured by Whatman) and then freeze-dried to obtain a hydrogen peroxide-urea freeze-dry member to be used as the absorption means 24.

(6) Preparation of anti-hCG antibody-immobilized porous cellulose ester film

A total of 200 circular pieces (13 mm in diameter) of a cellulose acetate/cellulose nitrate mixture ester porous membrane having a pore size of 8.0 μm (Cat. No. SCWP01300, manufactured by Nippon Millipore Kogyo) were put in a beaker filled with 200 ml of a PBS solution containing 1.0% (w/v) of bovine γ globulin (Cat. No. G7516, manufactured by Sigma Chemical) and heated at 60° C. for 2 hours with gentle stirring.

After removing the supernatant and further removing the remaining liquid by suction, the thus treated circular pieces were washed by stirring them in a sufficient volume of 0.076M phosphate-buffered saline (pH 6.4, to be referred to as "PBS" hereinafter) and then removing the used PBS. The washing step with PBS was further repeated twice, and the washed pieces were again washed with distilled water 7 times. After completion of the washing steps, the circular pieces were put in 200 ml of 1.0% glutaraldehyde aqueous solution and incubated at 25° C. for 3 hours with gentle stirring. After the reaction, the thus treated circular pieces of porous membranes were washed with distilled water 10 times and then arranged on a glass plate one by one to dry them.

On the other hand, mouse monoclonal anti-hCG antibody HM21 (manufactured by Mochida Pharmaceutical) was dissolved in a solution consisting of 0.05M sodium bicarbonate and 0.05M sodium chloride to a final concentration of 1.0 mg/ml. Each piece (13 mm in diameter) of the porous membrane dried on a glass plate was impregnated with 25 µl of the just prepared antibody solution from the central portion of the circular piece. After 1 hour of reaction at room temperature, the circular pieces of the porous membrane were put in 200 ml of a 0.2% bovine serum albumin (BSA)/PBS solution and shaken at 4° C. for 2 days to effect blocking. Thereafter, the thus treated pieces were washed three times with a 0.1% Tween 20/PBS solution and then seven times with PBS and then dried to obtain anti-hCG antibody (HM21)-immobilized porous cellulose mixture ester membrane to be used as the matrix 22.

(7) Preparation of detection means (electrode) 20

A pattern as shown in FIG. 4 was printed by means of screen printing on each of the face side and back side of a transparent PET film (50 mm in length, 20 mm in width and 0.25 mm in thickness) using a conductive carbon ink (400-CT, manufactured by Asahi Kaken). Also, the reference electrode 32 was printed by screen printing on the circular area of the central portion of the face side using a conductive silver ink (LS411N, manufactured by Asahi Kaken). In addition, the insulating layer 36 was printed on the face side and back side of the electrode by means of screen printing using an insulating ink (XB-101G, manufactured by Fujikura Kasei). Thereafter, a hole having a diameter of 3 mm was made on the center of the circular area using a punch for the purpose of using it as the through hole 30, in such a manner that ring-shaped electrodes remained on both face side and back side of the through hole 30. After the punching, it was confirmed that the face side and back side electrodes were electrically independent from each other.

Thereafter, the conductive silver ink-superposed portion was subjected to 10 minutes of electrolysis in 0.1M sodium chloride aqueous solution (+1.0 V vs Ag/AgCl) to form a silver chloride layer on the surface. Of the exposed ring zones, the side laminated with a silver/silver chloride layer was used as the reference electrode 32 (and counter electrode), and the other side of only conductive carbon was used as the working electrode 34 for detection use. [Preparation of assay device for inventive example use]

Using each of the thus prepared members, the assay device shown in FIGS. 2 and 3 of MEDIA method was constructed for use in the practice of the assay method of the present invention in the following manner.

Firstly, the absorption means 24 prepared in the above step (5) was put on the lower support 26 made of an acrylic resin. To the central part of the surface of the absorption means was applied a seal having a diameter of 6 mm which has been prepared by punching a mending tape (manufactured by Sumitomo 3M) to be used as the sealing means 24a. On the upper surface of this was superposed the matrix 22 prepared in the above step (6) in such a manner that its central point coincided with that of the sealing means 24a of the absorption means 24. Next, the electrode portion 20 prepared in the above step (7), with its reference electrode 32 being the upper side, was superposed on the matrix 22 in such a manner that the central point of the through hole 30 coincided with that of the matrix 22. A circular piece having a diameter of 3 mm was punched out from a glass fiber filter paper (GA55, manufactured by Advantech Toyo) and inserted in the through hole 30 to form the communication means 18. On the electrode portion 20 was further superposed the freeze-dried electron mediator(THEPD)-impregnated member 16 prepared in the above step (3) in such a manner that its central point coincided with that of the through hole 30 of the electrode portion 20. On the upper central portion of the electron mediator-impregnated member 16 was applied a seal of 6 mm in diameter prepared by punching a mending tape and used as the sealing means 16a. On this was superposed the labeled antibody-impregnated member 14 prepared in the above step (2) on which was further superposed a circular piece of 12 mm in diameter to be used as the filter 12, which has been prepared by punching a Tween 20-treated ERUTAS (Cat. No. A05070, manufactured by Asahi Chemical Industry). On this was finally superposed the upper cover 10 made of an acrylic plate of 5 mm in thickness having a sample-introducing hole 10a (6 mm in diameter) in such a manner that the central point of the sample-introducing hole 10a coincided with that of the filter 12. In this way, a specific binding assay device for use in the measurement of hCG concentration was constructed. In this instance, the distance between the lower surface of the upper plate and the upper surface of the lower support was adjusted to 3,400 µm.

[Preparation of assay device for comparative example use]

A specific binding assay device for use in the measurement of hCG concentration was constructed in the same manner as the case of the above inventive assay device except that the electron mediator-impregnated member 16 prepared by impregnating and freeze-drying THEPD in the above step (3) was replaced by another electron mediator-impregnated member 16 prepared by impregnating and freeze-drying TEPD in the above step (4).

[Measurement of hCG in whole blood]

Each of the thus constructed inventive and comparative specific binding assay devices for use in the hCG concentration measurement was connected with necessary measuring equipments such as a potentiostat and the like as described in Test Example 2. On the other hand, hCG was added to heparinized whole blood of healthy male volunteers to prepare solutions (A) (hCG 0 IU/l whole blood) an (B) (1,000 IU/l whole blood). A 260 µl portion of each of the solutions (A) and (B) was introduced into (spotted on) the sample-introducing means 38 through the sample-introducing hole 10a of the upper cover 10 of each of the inventive and comparative specific binding assay devices. After 30 seconds of the sample spotting, a potential of −150 mV was applied to the working electrode based on the counter/reference electrode to record electric current. Results of the measurement by the inventive and comparative assay devices are shown in FIGS. 22 and 23, respectively.

Figure 22:
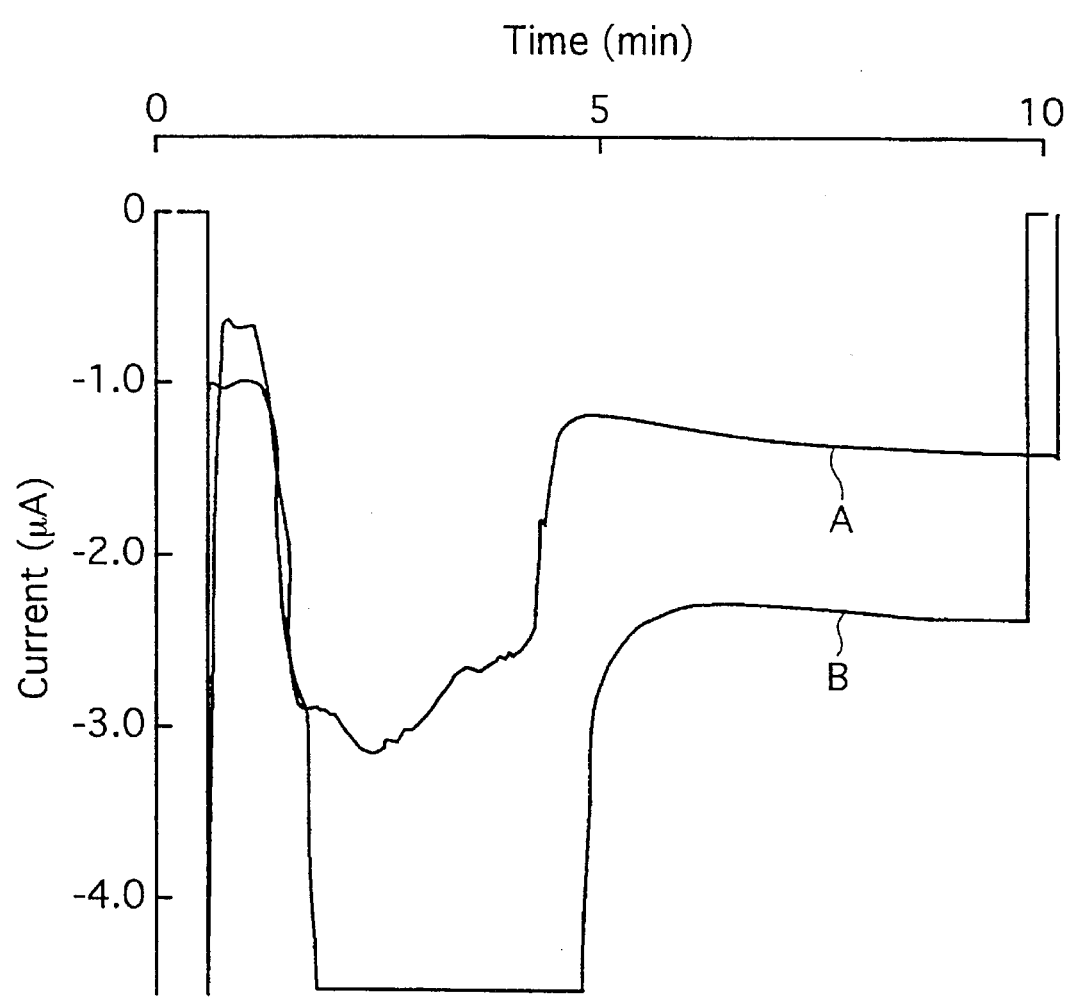
FIG. 22 is a graph showing an assay result of an inventive example carried out using the electron mediator of the present invention.
Figure 23:
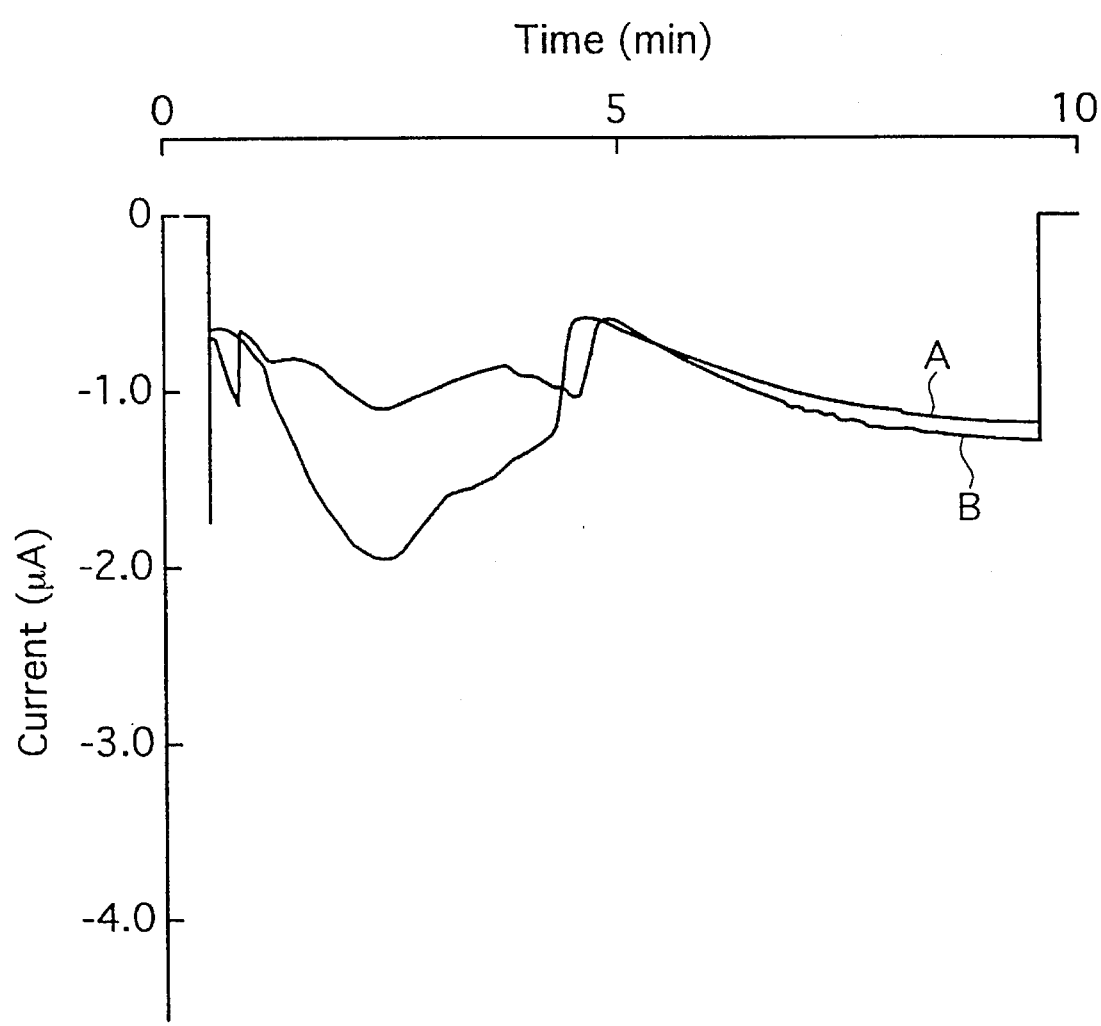
FIG. 23 is a graph showing an assay result of a comparative example carried out using a conventional electron mediator.

As shown in FIG. 22, the reduction current became high in response to the concentration of hCG in the case of the inventive specific binding assay device in which the freeze-dried THEPD member was used as the electron mediator-impregnated member 16. On the contrary, as shown in FIG. 23, the electric current did not increase in response to the concentration of hCG in the case of the comparative specific binding assay device in which the freeze-dried TEPD member was used as the electron mediator-impregnated member 16. These results, as well as the results of Test Example 1, indicate that TEPD cannot act as an appropriate electron mediator at the time of measurement in such a mode of assay method because of its poor drying property and stability in dried state, its aptness to undergo influence of interfering substances in samples and its poor stability in samples.

On the basis of these results, it was confirmed that quantitative determination of the concentration of hCG in a test sample can be made easily and quickly by the use of the assay device in which the electron mediator of the present invention is used.

Thus, as has been described in detail in the foregoing, according to the electrochemical assay method and novel p-phenylenediamine compound of the present invention, measurement of substances to be assayed by means of enzyme electrode method, specific binding assay methods such as MEDIA method and the like can be carried out always stably with high detection sensitivity (responsibility) and good reproducibility even in the case of blood, urine and the like samples that contain interfering substances, and the assay method can also be applied suitably to disposable use.

What is claimed is:

1. A method of measuring a substance in a liquid biological sample which comprises contacting with a sample containing said substance at least one oxidation-reduction enzyme and an electron mediator wherein said electron mediator is a compound represented by the following formula (I) or a salt thereof:

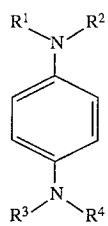

(I)

wherein $R^1$, $R^2$, $R^3$ and $R^4$ may be the same or different from one another and each represents a straight- or branched-chain alkyl group having 1 to 4 carbon atoms with the proviso that at least one of $R^1$, $R^2$, $R^3$ and $R^4$ has at least one group selected from the group consisting of hydroxyl, mercapto, carboxyl, phosphonooxy and sulfo; and measuring said substance with an electrode capable of performing electron transfer with said electron mediator.

2. The electrochemical assay method according to claim 1 wherein said at least one group of $R^1$, $R^2$, $R^3$ or $R^4$ is selected from the group consisting of a hydroxyl group and a carboxyl group.

3. The electrochemical assay method according to claim 1 wherein said compound represented by the formula (I) is selected from the group consisting of;

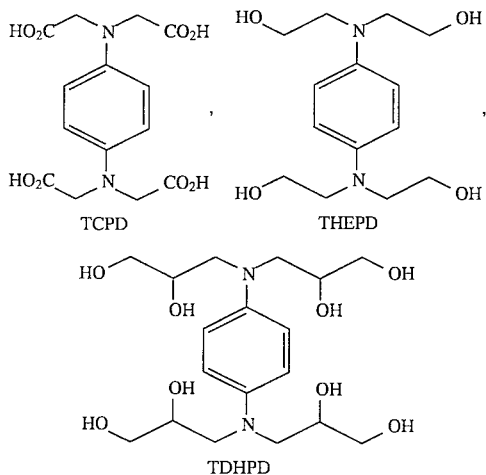

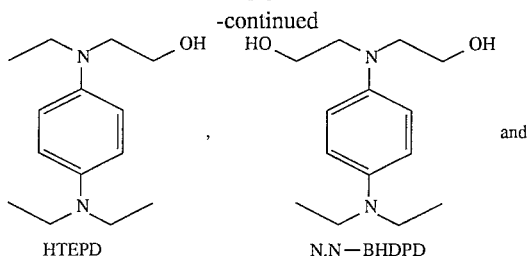

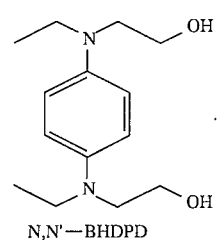

N,N'—BHDPD

4. The electrochemical assay method according to claim 1 wherein said substance is selected from the group consisting of a substrate, an inhibitor, a cofactor and an activator of said oxidation-reduction enzyme, and said measuring of said substance is through a modulation of an enzyme reaction generated in response to the amount of said substrate, inhibitor, cofactor or activator of said oxidation-reduction enzyme which is detected as a modulation of electrochemical signals at said electrode.

5. The electrochemical assay method according to claim 1 wherein said substance specifically reacts with at least one specific binding substance specific for said substance and said oxidation-reduction enzyme acts as a label.

6. The electrochemical assay method according to claim 5 further comprising, introducing the sample containing said substance into a matrix through a sample-introducing means;

reacting said substance in said matrix with a first specific binding substance and a second specific binding substance which is labeled with an oxidation-reduction enzyme capable of forming an electron transfer species that generates a signal at the electrode, or reacting said sample in an area outside said matrix with a first specific binding substance and a second specific binding substance which is labeled with an oxidation-reduction enzyme capable of forming an electron transfer species that generates a signal at the electrode and introducing said sample into said matrix; and detecting changes in the distribution of at least one molecular species among a complex of said oxidation-reduction enzyme-labeled second specific binding substance and said substance, a complex of said oxidation-reduction enzyme-labeled second specific binding substance, said substance and the first specific binding substance and a free form of the oxidation-reduction enzyme-labeled second specific binding substance which occur in response to the amount of said substance by measuring a signal modulation at the electrode, wherein said signal modulation is limited by the mass transfer of the electron transfer species generated by the oxidation-reduction enzyme.

7. The electrochemical assay method according to claim 5 further comprising introducing the sample containing said substance into a matrix through a sample-introducing means;

competitively reacting said substance with a specific binding substance or a substance which competes with said substance to be assayed for said specific binding substance, or introducing said sample into said matrix after competitively reacting said substance with a specific binding substance or a substance which competes with said substance to be assayed for the specific binding substance; and detecting changes in the distribution of at least one oxidation-reduction enzyme-labeled molecular species among a complex of said specific binding substance and said substance to be assayed, a complex of said specific binding substance and the substance which competes with said substance for said specific binding substance, a free form of said specific binding substance and a free form of said substance which competes with said substance for said specific binding substance, which occur in response to the amount of said substance by measuring a signal modulation at the electrode, wherein said signal modulation is limited by the mass transfer of the electron transfer species generated by the oxidation-reduction enzyme.

8. A method of measuring a substance in a liquid sample comprising contacting with a sample containing said substance, at least one oxidation-reduction enzyme, and an electron mediator wherein said electron mediator is a compound represented by the following formula (II) or a salt thereof:

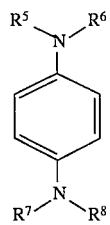

(II)

wherein $R^5$, $R^6$, $R^7$ and $R^8$ may be the same or different from one another and each represents a hydrogen, a straight- or branched-chain alkyl group having 1 to 4 carbon atoms with the proviso that at least one of $R^5$, $R^6$, $R^7$ and $R^8$ is an alkyl group which has at least one group selected from the group consisting of hydroxyl, mercapto, carboxyl, phosphonooxy and sulfo, and at least one of $R^5$, $R^6$, $R^7$ and $R^8$ is hydrogen; and measuring said substance with an electrode capable of performing electron transfer with an electron mediator.

9. The electrochemical assay method according to claim 8 wherein said at least one group of $R^5$, $R^6$, $R^7$ and $R^8$ has a hydroxyl group.

10. The electrochemical assay method according to claim 8 wherein said substance is selected from the group consisting of a substrate, an inhibitor, a cofactor and an activator of said oxidation-reduction enzyme, and said measuring of said substance is through a modulation of an enzyme reaction generated in response to the amount of said substrate, inhibitor, cofactor or activator of said oxidation-reduction enzyme which is detected as a modulation of electrochemical signals at said electrode.

11. The electrochemical assay method according to claim 8 wherein said substance to be assayed specifically reacted with at least one specific binding substance specific for the substance to be assayed and said oxidation-reduction enzyme acts as a label.

12. The electrochemical assay method according to claim 11 further comprising introducing the sample containing said substance into a matrix through a sample-introducing means;

reacting said substance in said matrix with a first specific binding substance and a second specific binding substance which is labeled with an oxidation-reduction enzyme capable of forming an electron transfer species that generates a signal at the electrode, or reacting said sample in an area outside said matrix with a first specific binding substance and a second specific binding substance which is labeled with an oxidation-reduction enzyme capable of forming an electron transfer species that generates a signal at the electrode and introducing said sample into said matrix; and detecting changes in the distribution of at least one molecular species among a complex of said oxidation-reduction enzyme-labeled second specific binding substance and said substance, a complex of said oxidation-reduction enzyme-labeled second specific binding substance, said substance and the first specific binding substance and a free form of the oxidation-reduction enzyme-labeled second specific binding substance which occur in response to the amount of said substance by measuring a signal modulation at the electrode, wherein said signal modulation is limited by the mass transfer of the electron transfer species generated by the oxidation-reduction enzyme.

13. The electrochemical assay method according to claim 11 further comprising introducing the sample containing said substance into a matrix through a sample-introducing means;

competitively reacting said substance with a specific binding substance or a substance which competes with said substance to be assayed for said specific binding substance, or introducing said sample into said matrix after competitively reacting said substance with a specific binding substance or a substance which competes with said substance to be assayed for the specific binding substance; and detecting changes in the distribution of at least one oxidation-reduction enzyme-labeled molecular species among a complex of said specific binding substance and said substance to be assayed, a complex of said specific binding substance and the substance which competes with said substance for said specific binding substance, a free form of said specific binding substance and a free form of said substance which competes with said substance for said specific binding substance which occur in response to the amount of said substance by measuring a signal modulation at the electrode, wherein said signal modulation is rate-limited by the mass transfer of the electron transfer species generated by the oxidation-reduction enzyme.

* * * * *